United States Patent
Mace et al.

(10) Patent No.: US 10,732,167 B2
(45) Date of Patent: Aug. 4, 2020

(54) MULTIPHASE SYSTEMS AND USES THEREOF

(71) Applicant: President and Fellows of Harvard College, Cambridge, MA (US)

(72) Inventors: Charles R. Mace, Auburn, NY (US); Ozge Akbulut Halatci, Allston, MA (US); Ashok A. Kumar, Medford, MA (US); Nathan D. Shapiro, Cambridge, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 17 days.

(21) Appl. No.: 15/657,951

(22) Filed: Jul. 24, 2017

(65) Prior Publication Data

US 2017/0322196 A1    Nov. 9, 2017

Related U.S. Application Data

(62) Division of application No. 13/817,976, filed as application No. PCT/US2011/048673 on Aug. 22, 2011, now Pat. No. 9,714,934.
(Continued)

(51) Int. Cl.
*G01N 33/00* (2006.01)
*G01N 33/49* (2006.01)
(Continued)

(52) U.S. Cl.
CPC ............ *G01N 33/491* (2013.01); *B03B 5/28* (2013.01); *B03B 5/442* (2013.01); *B03D 3/00* (2013.01);
(Continued)

(58) Field of Classification Search
CPC .................................................. G01N 33/491
(Continued)

(56) References Cited

U.S. PATENT DOCUMENTS

| 2,825,698 A | 3/1958 | Taylor et al. |
| 4,740,304 A | 4/1988 | Tjerneld et al. |

(Continued)

FOREIGN PATENT DOCUMENTS

| CA | 2358326 | 4/2003 |
| EP | 0954524 B1 | 4/2003 |

(Continued)

OTHER PUBLICATIONS

Fedotov, "Untraditional Applications of Countercurrent Chromatography," Journal of Liquid Chromatography and Related Technologies, Feb. 2002, vol. 25, Nos. 13-15, pp. 2065-2078.
(Continued)

*Primary Examiner* — Christopher Adam Hixson
*Assistant Examiner* — Emily R. Berkeley
(74) *Attorney, Agent, or Firm* — Wilmer Cutler Pickering Hale and Dorr LLP

(57) ABSTRACT

A multi-phase system includes a phase-separated solution comprising at least two phases, each phase having a phase component selected from the group consisting of a polymer, a surfactant and combinations thereof, wherein at least one phase comprises a polymer, wherein the phases, taken together, represent a density gradient. Novel two-phase, three-phase, four-phase, five-phase, or six-phase systems are disclosed. Using the disclosed multi-phase polymer systems, particles, or other analyte of interest can be separated based on their different densities or affinities.

29 Claims, 14 Drawing Sheets

Related U.S. Application Data

(60) Provisional application No. 61/375,532, filed on Aug. 20, 2010.

(51) Int. Cl.
   *B03B 5/28*   (2006.01)
   *B03B 5/44*   (2006.01)
   *B03D 3/00*   (2006.01)
   *G01N 33/537* (2006.01)
   *G01N 33/574* (2006.01)
   *G01N 33/18*  (2006.01)

(52) U.S. Cl.
   CPC ......... *G01N 33/18* (2013.01); *G01N 33/5375* (2013.01); *G01N 33/57492* (2013.01)

(58) Field of Classification Search
   USPC ........................................................ 436/177
   See application file for complete search history.

(56) References Cited

U.S. PATENT DOCUMENTS

| | | |
|---|---|---|
| 5,078,886 A | 1/1992 | Hsu |
| 5,316,540 A | 5/1994 | McMannis et al. |
| 5,432,054 A | 7/1995 | Saunders et al. |
| 5,772,888 A | 6/1998 | Liu et al. |
| 5,840,502 A | 11/1998 | Van Vlasselaer |
| 5,962,237 A | 10/1999 | Ts'o et al. |
| 6,048,715 A | 4/2000 | Haynes et al. |
| 6,210,889 B1 | 4/2001 | Drouin et al. |
| 6,454,950 B1 | 9/2002 | Tjerneld et al. |
| 6,677,439 B1 | 1/2004 | Blanco et al. |
| 9,176,105 B2 | 11/2015 | Mace et al. |
| 9,857,353 B2 | 1/2018 | Mace et al. |
| 2007/0036722 A1 | 2/2007 | Rongved et al. |
| 2007/0067463 A1 | 3/2007 | Ishibashi et al. |
| 2007/0125716 A1 | 6/2007 | Procter et al. |
| 2007/0249502 A1 | 10/2007 | Procter et al. |
| 2009/0325218 A1 | 12/2009 | Melis |
| 2010/0041014 A1 | 2/2010 | Hyde et al. |
| 2010/0120085 A1 | 5/2010 | Hyman et al. |
| 2010/0129857 A1 | 5/2010 | Walsh et al. |
| 2010/0195916 A1 | 8/2010 | Blondiaux et al. |
| 2013/0280693 A1 | 10/2013 | Mace et al. |
| 2013/0313483 A1 | 11/2013 | Mace et al. |

FOREIGN PATENT DOCUMENTS

| | | |
|---|---|---|
| EP | 1159290 | 5/2004 |
| GB | 2239197 | 6/1991 |
| IL | 106488 | 8/1996 |
| JP | 5229951 | 9/1993 |
| WO | WO-87/05393 | 9/1987 |
| WO | WO-91/04318 A1 | 4/1991 |
| WO | WO-96/04556 | 2/1996 |
| WO | WO-2004/018066 A2 | 3/2004 |
| WO | WO-2006/003134 A1 | 1/2006 |
| WO | WO-2007/067463 A1 | 6/2007 |
| WO | WO-2007/067728 A1 | 6/2007 |
| WO | WO-2008049083 A2 | 4/2008 |
| WO | WO-2008/156409 A1 | 12/2008 |
| WO | WO-2008/156410 A1 | 12/2008 |
| WO | WO-2012/024688 | 2/2012 |
| WO | WO-2012/024693 A1 | 2/2012 |
| WO | WO-2012024690 A1 | 2/2012 |
| WO | WO-2012024691 A1 | 2/2012 |

OTHER PUBLICATIONS

Silvestre et al., "Exploitation of a single interface flow system for on-line aqueous biphasic extraction," Talanta, vol. 81, pp. 1847-1851, published online Mar. 31, 2010.

Albertsson, Per-ake et al. "Affinity Separation of Proteins in Aqueous Three-Phase Systems." Analytical Biochemistry. 175, No Month Listed 1988. pp. 154-161.

Albertsson, Per-Ake. "Application of the Phase Partition Method to a Hydrophobic Membrane Protein, Phospholipase A1 from *Eschrichia coli*." Biochemistry. vol. 12, No. 13, No Month Listed 1973. pp. 2525-2530.

Asenjo, J.A. et al. "Phase Separation Rates of Aqueous Two-Phase Systems: Correlation with System Properties." Biotechnology and Bioengineering, vol. 79, No. 2, Jul. 20, 2002. pp. 217-223.

Grover, William H. et al. "Measuring Single-Cell Density." PNAS. vol. 108, No. 27, Jul. 5, 2011. pp. 10992-10996.

International Search Report and Written Opinion for International Application No. PCT/US2011/048673 dated Jan. 20, 2012. 20 pages.

International Search Report and Written Opinion for International Application No. PCT/US2011/048675 dated Nov. 2, 2011.

International Search Report and Written Opinion for International Application No. PCT/US2011/048676 dated Nov. 2, 2011.

International Search Report and Written Opinion for International Application No. PCT/US2011/048678 dated Nov. 2, 2011. 10 pages.

Ruan, Ke et al. "Interfacial Tension of Aqueous Three-Phase Systems Formed by Triton X-100/PEG/Dextran." Journal of Dispersion Science and Technology, 27, No Month Listed 2006. pp. 927-930.

Wong et al., "Egg Beater as Centrifuge: Isolating Human Blood Plasma from Whole Blood in Resource-poor Setting," Lab Chip, 2008, 8, pp. 2032-2037.

Chiu, Thomas T. et al. "Poly(2-ethyl-2-oxazoline): A New Water- and Organic-Soluble Adhesive." Advances in Chemistry. American Chemical Society, Washington, DC. vol. 213, Chapter 23, No Month Listed 1986. pp. 425-433.

Sivars, Ulf et al. "Mechanisms of Phase Behaviour and Protein Partitioning in Detergent/Polymer Aqueous Two-phase Systems for Purification of Integral Membrane Proteins." Biochimica et Biophysica Acta 1474. Elsevier Science B.V. No Month Listed 2000. pp. 133-146.

Liu, T. and Shan, G., "Mechanism of the Droplet Formation and Stabilization in the Aqueous Two-Phase Polymerization of Acrylamide," Journal of Applied Polymer Science, vol. 112, pp. 2859-2867 (Feb. 24, 2009).

Yankov et al., "Influence of pH and acid solutes on the phase behavior of aqueous solutions containing poly(ethylene glycol) and poly(ethyleneimine)", Biochemical Engineering Journal, vol. 48, pp. 104-110, (2009).

Guorong et al., "A New Polymerization Method and Kinetics for Acrylamide: Aqueous two-phase Polymerization", Journal of Applied Polymer Science, vol. 111, pp. 1409-1416, (2009).

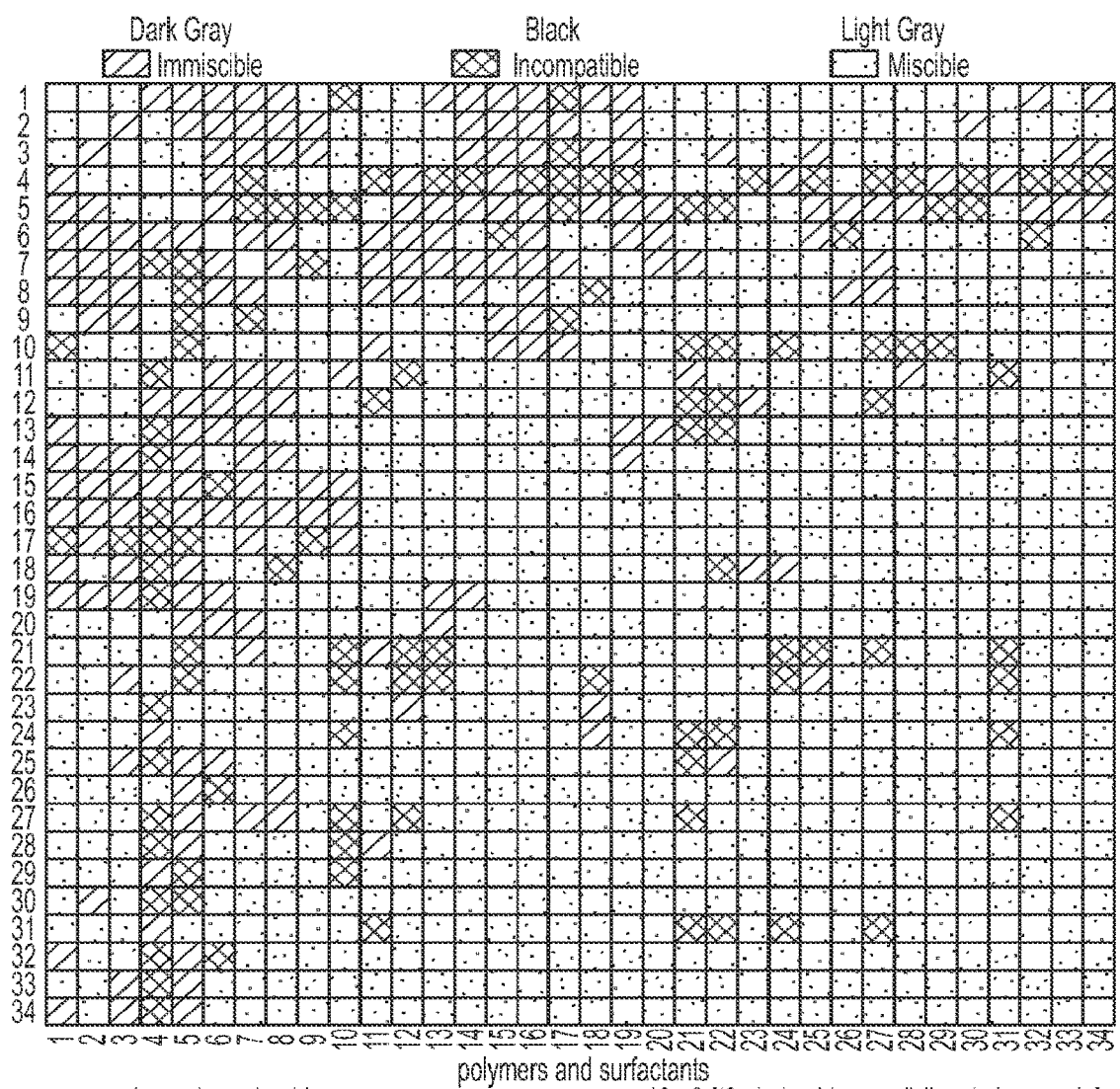

FIG. 1 polymers and surfactants 1 polyacrylamide
2 Ficoll
3 dextran
4 poly(acrylic acid)
5 poly(methacrylic acid)
6 poly(ethylene glycol)
7 poly(2-ethyl-2-oxazoline)
8 poly(vinyl alcohol)
9 hydroxyethyl cellulose
10 polyallylamine
11 dextran sulfate
12 poly(diallyldimethyl ammonium chloride)
13 polyethyleneimine
14 Pluronic F68
15 Triton X-100
16 Tween 20
17 Brij 35
18 poly(propylene glycol)
19 3-[(3-cholamidopropyl)dimethylammonio]-1-propanesulfonate
20 1-O-octyl-β-D-glucopyranoside
21 poly(styrene sulfonic acid)
22 poly(2-acrylamido-2-methyl-1-propanesulfonic acid)
23 (hydroxypropyl)methyl cellulose
24 alginic acid
25 polyvinylpyrrolidone
26 carboxy-polyacrylamide
27 chondroitin sulfate A
28 sodium chloate
29 sodium dodecylsulfate
30 methyl cellulose
31 diethylammoethyl-dextran
32 N,N-dimethyldedecylamine N-oxide
33 nonylphenol polyoxyethylene 20
34 Zonyl

FIG. 5

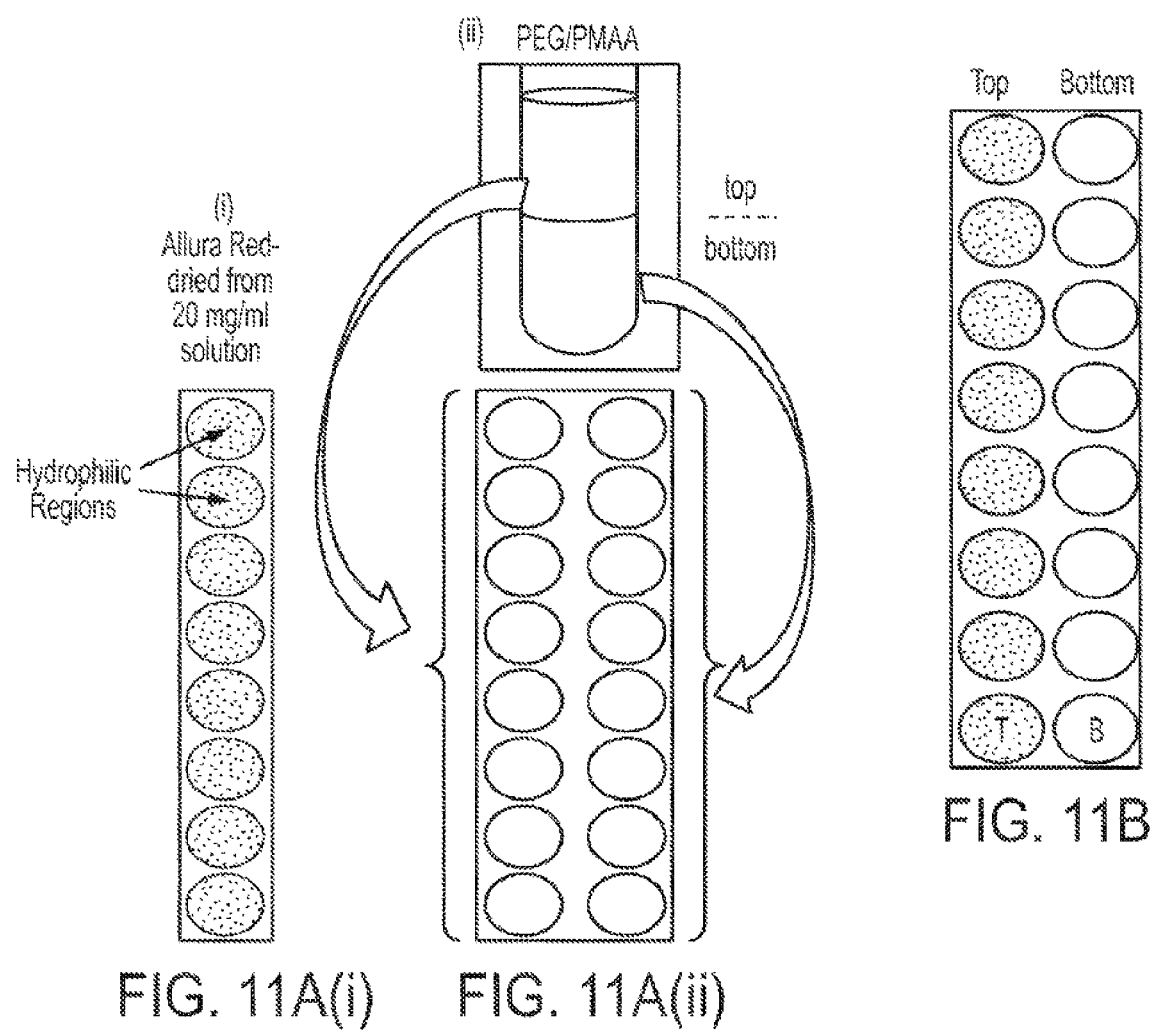
FIG. 11A(i)   FIG. 11A(ii)   FIG. 11B

MULTIPHASE SYSTEMS AND USES THEREOF

RELATED APPLICATIONS

This application is a divisional application of U.S. patent Ser. No. 13/817,976, filed Aug. 14, 2013, which is a National Stage Entry of PCT/US2011/48673, filed Aug. 22, 2011, which claims priority to U.S. Provisional Patent Application No. 61/375,532, filed on Aug. 20, 2010, the contents of all of which are hereby incorporated by reference in its entirety. This application is also related to the following applications, filed concurrently herewith, the entire contents of which are incorporated herein by reference:

PCT Patent Application No. PCT/US2011/048678, filed on Aug. 22, 2011, entitled "DENSITY-BASED SEPARATION OF BIOLOGICAL ANALYTES USING MULTIPHASE SYSTEMS;"

PCT Patent Application No. PCT/US2011/048675, filed on Aug. 22, 2011, entitled "MULTIPHASE SYSTEMS HAVING MULTIPLE PHASE PROPERTIES;" and PCT Patent Application No. PCT/US2011/048676, filed on Aug. 22, 2011, entitled "MULTIPHASE SYSTEMS FOR ANALYSIS OF SOLID MATERIALS."

INCORPORATION BY REFERENCE

All non-patent literature, patents, patent applications and publications cited herein are hereby incorporated by reference in their entirety in order to more fully describe the state of the art as known to those skilled therein as of the date of the invention described herein.

BACKGROUND

It is known that the aqueous mixtures of two polymers such as poly(ethylene glycol) (PEG) and dextran can separate spontaneously into two aqueous phases, called aqueous two-phase systems. Phase separation in aqueous solutions of polymers is an extraordinary and underexplored phenomenon. When two aqueous solutions of polymers are mixed, the resulting system is not homogeneous; rather, two discrete phases, or layers, form. These layers are ordered according to density and arise from the mutual immiscibility of the polymers for one another. In these systems, each phase predominantly consists of water (upwards of 70-90% (w/v)), while the polymer component is present in concentrations ranging from micromolar to millimolar. A low interfacial tension and rapid mass transfer of water-soluble molecules across the boundary characterize the interface between layers.

Previous studies of partitioning between aqueous phases have been limited to biphasic systems of immiscible polymers or inorganic salts and have focused on applications in protein chemistry, cell partitioning, and manufacturing. These Aqueous Two-Phase Systems ("ATPS") are exemplified by the poly(ethylene glycol)-dextran, dextran-Ficoll systems, and a poly(ethylene glycol) system comprising $(NH_4)_2SO_4$.

Although numerous biphasic systems have been reported, there have been relatively few reports of polymer systems that exhibit multiphase, e.g., more than two phases, separation: (i) poly(ethylene glycol)-dextran-Ficoll, (ii) Triton X100-poly(ethylene glycol)-dextran, and (iii) poly(propylene glycol)-poly(ethylene glycol)-dextran-Ficoll. The four-phase system, however, is not entirely an aqueous system because the liquid poly(propylene glycol) that was employed in the assay is insoluble in water. Thus, while polymeric, this "four" phase system can be compared to the incorporation of an organic solvent or perfluorinated alkane into a three-phase system.

SUMMARY

Described herein are methods of separating or analyzing analytes of interest using multi-phase systems ("MPS") comprising two or more phases having different densities. In some embodiments, MPS as described herein are used to separate analytes from each other or from impurities and other objects in the sample when the analytes migrate to phases characteristic of their densities, and in so doing, contact each phase of the multi-phase system sequentially. As used herein, "sequential contact" means that the analyte contacts and interacts with only one phase (and its major phase component) at a time except at the interface where the analyte may contact and interact with two adjacent phases simultaneously. That is, the interaction of the analyte with the MPS occurs when the MPS has already phase separated and not during the process of phase separation. In some embodiments, a multi-phase system comprising a phase component is used and the analyte contacts each phase of the multi-phase system sequentially.

As used herein, a sample comprising one or more analyte is a mixture of species that can be characterized, and differentiated, by a set of physical properties (e.g., density, size, or potentially others). A multi-phase system can be designed to separate the analyte mixture into multiple populations at the interfaces between phases. These populations can be pure (a single species; ideal) or mixed. If mixed, the compositions of the species captured at each interface share at least one feature. For example, their densities are greater than that of the phase above but lesser than that of the phase below.

The multi-phase systems used in the methods disclosed herein comprise two or more phases that are phase-separated from each other, wherein of the two or more phases comprises a phase component. The phase component is one or more selected from the group consisting of polymer, surfactant, or combinations thereof, wherein at least one of the phase components is a polymer. The phases in the multi-phase system can be aqueous or organic. In some embodiments, at least one phase of the multi-phase system is aqueous and at least one phase of the multi-phase system is organic.

As used herein, MPS refers to a multi-phase system. When two or more solutions containing a phase component are mixed, the resulting system is not homogeneous; rather, two or more discrete phases, or layers, form. These layers are ordered according to density and arise from the exhibit limited interaction of the phase components with one another. The two or more phases or solutions, which exhibit limited interaction and form distinct phase boundaries between adjacent phases. Each phase can be aqueous or non-aqueous. The non-aqueous phase comprises an organic liquid or an organic solvent.

As used herein, AMPS refers to an aqueous multi-phase polymer system. ATPS refers to an aqueous two-phase polymer system.

As used herein, an aqueous multi-phase polymer system comprises two or more polymer aqueous solutions or phases, which are phase-separated and in which at least two aqueous solutions each comprises a polymer. In some embodiments, the aqueous multi-phase polymer system can be combined with one or more immiscible organic phases to form a multi-phase system.

As used herein, the polymer includes, but is not limited to, the homopolymer, copolymer, terpolymer, and block copolymer, random copolymers and terpolymers of that polymer. As used herein, copolymer refers to a polymer derived from two monomeric species; similarly, a terpolymer refers to a polymer derived from three monomeric species. Block copolymers include, but are not limited to, block, graft, dendrimer, and star polymers. The polymer also includes various morphologies, including, but not limited to, linear polymer, branched polymer, crosslinked polymer, and dendrimer systems. As an example, polyacrylamide polymer refers to any polymer including polyacrylamide, e.g., a homopolymer, copolymer, terpolymer, block copolymer or terpolymer of polyacrylamide. Polyacrylamide can be a linear polymer, branched polymer, crosslinked polymer, or a dendrimer of polyacrylamide.

In one aspect, a multi-phase system is described, comprising:
two or more phase-separated phases including at least a first and second phases, wherein
each of the first and second phases comprises a phase component selected from the group consisting of a polymer, a surfactant and combinations thereof, wherein at least one of the first and second phases comprises a polymer;
each said phase has an upper and a lower phase boundary; and
each of the two or more phases has a different density and the phases, taken together, represent a density gradient; and
an analyte contained within the phase-separated solution, wherein the analyte is located predominantly at one of the phase boundaries.

The phase component is selected from the group consisting of a polymer, a surfactant and combinations thereof. The phase "combination" refers to the combination of a polymer and a surfactant, a combination of two or more polymers, a combination of two or more surfactants, or a combination of any number of polymers and any number of surfactants.

In any of the preceding embodiments, greater than 80% of the analyte is located at one or more of the phase boundaries.

In any of the preceding embodiments, greater than 90% of the analyte is located at one or more of the phase boundaries.

In any of the preceding embodiments, the system comprises more than one analyte and the additional analytes are located at the same or different phase boundary.

In another aspect, a multi-phase system is described, comprising:
at least two phase-separated non-aqueous phases, wherein
each phase comprises a phase component selected from the group consisting of a polymer, a surfactant and combinations thereof,
wherein at least one phase comprises a polymer; and
each of the two or more phases has a different density and the phases, taken together, represent a density gradient.

In any of the preceding embodiments, the multi-phase system comprises three or more phases.

In any of the preceding embodiments, the multi-phase system comprises more than one solvent, and wherein the phases comprising a common solvent share at least one boundary.

In any of the preceding embodiments, the phases comprises a common solvent and the common solvent is an aqueous solvent.

In any of the preceding embodiments, wherein the phases comprises a common solvent which is an organic solvent.

In any of the preceding embodiments, the organic solvent is selected from the groups consisting of liquid polymer, non-polar organic solvent, polar aprotic or protic solvent, supercritical fluid, fuel, oils, and fluorinated solvents, and combinations thereof.

In any of the preceding embodiments, the common solvent comprises dichloromethane.

In any of the preceding embodiments, the multi-phase system comprises phase separated solutions selected from the group consisting of organic solutions, silicon oils, ionic liquids, fluorinated solvents, and liquid metals.

In any of the preceding embodiments, the multi-phase system comprises three or more phases, and additional phase separated phases selected from the group consisting of organic solutions, silicon oils, ionic liquids, fluorinated solvents, and liquid metals.

In any of the preceding embodiments, the aqueous phase is selected from the group consisting of water, isotopes of water, buffered water, sea water, irrigation water, mine effluent, colloidal solutions, emulsions, and combinations thereof.

In any of the preceding embodiments, the multi-phase system further comprises one or more additional analytes located predominantly at one or more of the phase boundaries.

In any of the preceding embodiments, the analyte is insoluble in the multi-phase system.

In any of the preceding embodiments, the analyte has at least one dimension greater than 200 nm.

In any of the preceding embodiments, the analyte is selected from the group consisting of solid particles, an aggregate of particles, a liquid or gel immiscible in the solvent, a liquid crystal, crystalline materials.

In any of the preceding embodiments, the analyte is selected from the group consisting of gem, bead, metal, glass, rock, mineral, crystal, plastic, bone, rubber, paper, fabric, coal, gases, polymer particles, and a combination thereof.

In any of the preceding embodiments, the polymer is selected from the group of homopolymers, random copolymers, block copolymers, graft copolymers, ter-polymers, dendrimers, star polymers and combinations thereof.

In any of the preceding embodiments, the polymer is linear, branched and/or cross-linked.

In any of the preceding embodiments, the polymer is selected from the group consisting of dextran, dextran sulfate, chondroitin sulfate A, polysucrose, diethylamino-ethyl-dextran, poly(2-vinylpyridine-N-oxide), poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propanesulfonic acid), poly(diallyldimethyl ammonium chloride), poly(styrene sulfonic acid), polyallylamine, alginic acid, poly(bisphenol A carbonate), polydimethylsiloxane, polystyrene, poly(4-vinylpyridine), polycaprolactone, polysulfone, poly(methyl methacrylate-co-methacrylic acid), poly(methyl methacrylate), poly (tetrahydrofuran), poly(propylene glycol), and poly(vinyl acetate) and copolymers or terpolymer thereof.

In any of the preceding embodiments, the surfactant is selected from the group consisting of polysorbate, 3-[(3-cholamidopropyl)dimethylammonio]-1-propanesulfonate, polyoxyethylene-polyoxypropylene, 1-O-Octyl-β-D-glucopyranoside, 4-(1,1,3,3-Tetramethylbutyl)phenyl-polyethylene glycol, 2-(Perfluoroalkyl)ethyl methacrylate, nonylphenol polyoxyethylene, N,N-dimethyldodecylamine N-oxide, polyethylene glycol dodecyl ether, sodium dodecyl sulfate, sodium cholate, benzylalkonium chloride and dodecyltrimethylammonium chloride.

In any of the preceding embodiments, one or more phases further comprise an additive selected from the group consisting of a salt, a miscible surfactant, a co-solvent, an acid, a base, a miscible polymer, vitamin, drug, antibiotic, small molecule, dye, colloid, and flurophore.

In yet another aspect, an aqueous two-phase system is described, comprising: a phase-separated solution comprising two aqueous phases, wherein each of the phases comprises a phase component and has a different density and the phases, taken together, represent a density gradient, and wherein the phase component combination of the two phases is selected from the group consisting of:

| Number | Phase component combinations | |
|---|---|---|
| 1 | poly(2-ethyl-2-oxazoline) | poly(methacrylic acid) |
| 2 | poly(2-ethyl-2-oxazoline) | poly(vinyl alcohol) |
| 3 | poly(ethylene glycol) | poly(methacrylic acid) |
| 6 | poly(ethylene glycol) | poly(2-ethyl-2-oxazoline) |
| 8 | dextran | poly(2-ethyl-2-oxazoline) |
| 10 | Ficoll | poly(methacrylic acid) |
| 11 | Ficoll | poly(vinyl alcohol) |
| 12 | Ficoll | poly(2-ethyl-2-oxazoline) |
| 15 | polyacrylamide | poly(methacrylic acid) |
| 16 | polyacrylamide | poly(acrylic acid) |
| 18 | polyacrylamide | poly(2-ethyl-2-oxazoline) |
| 19 | polyacrylamide | poly(ethylene glycol) |
| 20 | poly(diallyldimethyl ammonium chloride | poly(methacrylic acid) |
| 21 | poly(diallyldimethyl ammonium chloride | poly(acrylic acid) |
| 22 | poly(diallyldimethyl ammonium chloride | poly(vinyl alcohol) |
| 23 | poly(diallyldimethyl ammonium chloride | poly(2-ethyl-2-oxazoline) |
| 24 | poly(diallyldimethyl ammonium chloride | poly(ethylene glycol) |
| 25 | dextran sulfate | poly(vinyl alcohol) |
| 26 | dextran sulfate | poly(2-ethyl-2-oxazoline) |
| 28 | chondroitin sulfate A | poly(methacrylic acid) |
| 29 | chondroitin sulfate A | poly(vinyl alcohol) |
| 30 | chondroitin sulfate A | poly(2-ethyl-2-oxazoline) |
| 31 | polyethyleneimine | poly(methacrylic acid) |
| 32 | polyethyleneimine | poly(2-ethyl-2-oxazoline) |
| 33 | polyethyleneimine | poly(ethylene glycol) |
| 34 | polyethyleneimine | Ficoll |
| 35 | polyethyleneimine | polyacrylamide |
| 36 | polyvinylpyrrolidone | poly(methacrylic acid) |
| 39 | poly(propylene glycol) | poly(methacrylic acid) |
| 41 | poly(propylene glycol) | polyacrylamide |
| 42 | poly(2-acrylamido-2-methyl-1-propanesulfonic acid) | dextran |
| 43 | poly(2-acrylamido-2-methyl-1-propanesulfonic acid) | polyvinylpyrrolidone |
| 44 | poly(styrene sulfonic acid) | poly(2-ethyl-2-oxazoline) |
| 45 | poly(styrene sulfonic acid) | dextran sulfate |
| 46 | diethylaminoethyl-dextran | poly(acrylic acid) |
| 47 | polyallylamine | dextran sulfate |
| 48 | alginic acid | poly(acrylic acid) |
| 49 | alginic acid | poly(propylene glycol) |
| 50 | (hydroxypropyl)methyl cellulose | poly(diallyldimethyl ammonium chloride |
| 51 | (hydroxypropyl)methyl cellulose | poly(propylene glycol) |
| 52 | carboxy-polyacrylamide | poly(methacrylic acid) |
| 53 | carboxy-polyacrylamide | poly(vinyl alcohol) |
| 54 | carboxy-polyacrylamide | polyethyleneimine |
| 55 | hydroxyethyl cellulose | dextran |
| 56 | hydroxyethyl cellulose | Ficoll |
| 57 | methyl cellulose | Ficoll |
| 58 | Zonyl | poly(methacrylic acid) |
| 59 | Zonyl | dextran |
| 60 | Zonyl | polyacrylamide |
| 61 | Brij | poly(2-ethyl-2-oxazoline) |
| 62 | Brij | Ficoll |
| 63 | Brij | polyallylamine |
| 64 | Tween | poly(methacrylic acid) |
| 65 | Tween | poly(vinyl alcohol) |
| 66 | Tween | poly(2-ethyl-2-oxazoline) |
| 69 | Tween | Ficoll |
| 70 | Tween | polyacrylamide |
| 71 | Tween | polyallylamine |
| 72 | Tween | hydroxyethyl cellulose |
| 73 | Triton | poly(methacrylic acid) |
| 74 | Triton | poly(acrylic acid) |
| 75 | Triton | poly(2-ethyl-2-oxazoline) |
| 77 | Triton | Ficoll |
| 78 | Triton | polyacrylamide |
| 79 | Triton | polyallylamine |
| 81 | nonylphenol polyoxyethylene | poly(methacrylic acid) |
| 82 | nonylphenol polyoxyethylene | dextran |
| 83 | 1-O-Octyl-B-D-glucopyranoside | poly(methacrylic acid) |
| 84 | 1-O-Octyl-B-D-glucopyranoside | poly(2-ethyl-2-oxazoline) |
| 86 | 1-O-Octyl-B-D-glucopyranoside | polyethyleneimine |
| 87 | Pluronic | poly(methacrylic acid) |
| 88 | Pluronic | poly(vinyl alcohol) |
| 89 | Pluroni | poly(2-ethyl-2-oxazoline) |
| 90 | Pluronic | dextran |
| 91 | Pluronic | Ficoll |
| 92 | Pluronic | polyacrylamide |
| 93 | Pluronic | polyethyleneimine |
| 94 | sodium dodecyl sulfate | poly(acrylic acid) |
| 95 | sodium cholate | poly(methacrylic acid) |
| 96 | sodium cholate | dextran sulfate |
| 97 | N,N-dimethyldodecylamine N-oxide | poly(methacrylic acid) |
| 98 | N,N-dimethyldodecylamine N-oxide | polyacrylamide |
| 99 | CHAPS | poly(methacrylic acid) |
| 100 | CHAPS | poly(2-ethyl-2-oxazoline) |
| 101 | CHAPS | poly(ethylene glycol) |
| 102 | CHAPS | dextran |
| 103 | CHAPS | Ficoll |
| 104 | CHAPS | polyacrylamide |
| 105 | CHAPS | polyethyleneimine |
| 106 | CHAPS | Pluronic |
| 107 | PVPNO | PA |
| 108 | PVPNO | PMAA |
| 111 | PVPNO | PEOZ |
| 112 | PVPNO | PEG |
| 116 | PVPNO | PEI |
| 117 | PVPNO | Tween |

In yet another aspect, an aqueous three-phase system is described, comprising:

a phase-separated solution comprising three aqueous phases, wherein each of the phases comprises a phase component and has a different density and the phases, taken together, represent a density gradient, and wherein the phase component combination of the three phases is selected from the group consisting of:

| Number | Phase component combinations | | |
|---|---|---|---|
| 1 | poly(methacrylic acid) | poly(2-ethyl-2-oxazoline) | poly(ethylene glycol) |
| 2 | poly(methacrylic acid) | poly(2-ethyl-2-oxazoline) | Ficoll |
| 3 | poly(methacrylic acid) | poly(2-ethyl-2-oxazoline) | polyacrylamide |

-continued

| Number | Phase component combinations | | |
|---|---|---|---|
| 4 | poly(methacrylic acid) | poly(2-ethyl-2-oxazoline) | poly(diallyldimethyl ammonium chloride) |
| 5 | poly(methacrylic acid) | poly(2-ethyl-2-oxazoline) | chondroitin sulfate A |
| 6 | poly(methacrylic acid) | poly(2-ethyl-2-oxazoline) | polyethyleneimine |
| 7 | poly(methacrylic acid) | poly(2-ethyl-2-oxazoline) | Tween |
| 8 | poly(methacrylic acid) | poly(2-ethyl-2-oxazoline) | Triton |
| 9 | poly(methacrylic acid) | poly(2-ethyl-2-oxazoline) | 1-O-Octyl-B-D-glucopyranoside |
| 10 | poly(methacrylic acid) | poly(2-ethyl-2-oxazoline) | Pluronic |
| 11 | poly(methacrylic acid) | poly(2-ethyl-2-oxazoline) | CHAPS |
| 12 | poly(methacrylic acid) | poly(ethylene glycol) | Ficoll |
| 13 | poly(methacrylic acid) | poly(ethylene glycol) | polyacrylamide |
| 14 | poly(methacrylic acid) | poly(ethylene glycol) | poly(diallyldimethyl ammonium chloride) |
| 15 | poly(methacrylic acid) | poly(ethylene glycol) | polyethyleneimine |
| 16 | poly(methacrylic acid) | poly(ethylene glycol) | polyvinylpyrrolidone |
| 17 | poly(methacrylic acid) | poly(ethylene glycol) | Tween 20 |
| 18 | poly(methacrylic acid) | poly(ethylene glycol) | 1-O-Octyl-B-D-glucopyranoside |
| 19 | poly(methacrylic acid) | poly(ethylene glycol) | CHAPS |
| 20 | poly(methacrylic acid) | Ficoll | polyethyleneimine |
| 21 | poly(methacrylic acid) | Ficoll | Tween |
| 22 | poly(methacrylic acid) | Ficoll | Triton |
| 23 | poly(methacrylic acid) | Ficoll | Pluronic |
| 24 | poly(methacrylic acid) | Ficoll | CHAPS |
| 25 | poly(methacrylic acid) | polyacrylamide | polyethyleneimine |
| 26 | poly(methacrylic acid) | polyacrylamide | poly(propylene glycol) |
| 27 | poly(methacrylic acid) | polyacrylamide | Zonyl |
| 28 | poly(methacrylic acid) | polyacrylamide | Tween |
| 29 | poly(methacrylic acid) | polyacrylamide | Triton |
| 30 | poly(methacrylic acid) | polyacrylamide | Pluronic |
| 31 | poly(methacrylic acid) | polyacrylamide | N,N-dimethyldodecylamine N-oxide |
| 32 | poly(methacrylic acid) | polyacrylamide | CHAPS |
| 33 | poly(methacrylic acid) | polyethyleneimine | carboxy-polyacrylamide |
| 34 | poly(methacrylic acid) | polyethyleneimine | 1-O-Octyl-B-D-glucopyranoside |
| 35 | poly(methacrylic acid) | polyethyleneimine | Pluronic |
| 36 | poly(methacrylic acid) | polyethyleneimine | CHAPS |
| 37 | poly(methacrylic acid) | Pluronic F68 | CHAPS |
| 38 | poly(acrylic acid) | poly(ethylene glycol) | polyacrylamide |
| 39 | poly(acrylic acid) | poly(ethylene glycol) | poly(diallyldimethyl ammonium chloride) |
| 40 | poly(acrylic acid) | polyacrylamide | Triton |
| 41 | poly(vinyl alcohol) | poly(2-ethyl-2-oxazoline) | poly(ethylene glycol) |
| 42 | poly(vinyl alcohol) | poly(2-ethyl-2-oxazoline) | dextran |
| 43 | poly(vinyl alcohol) | poly(2-ethyl-2-oxazoline) | Ficoll |
| 44 | poly(vinyl alcohol) | poly(2-ethyl-2-oxazoline) | polyacrylamide |
| 45 | poly(vinyl alcohol) | poly(2-ethyl-2-oxazoline) | poly(diallyldimethyl ammonium chloride) |
| 46 | poly(vinyl alcohol) | poly(2-ethyl-2-oxazoline) | dextran sulfate |
| 47 | poly(vinyl alcohol) | poly(2-ethyl-2-oxazoline) | chondroitin sulfate A |
| 48 | poly(vinyl alcohol) | poly(2-ethyl-2-oxazoline) | Tween |
| 49 | poly(vinyl alcohol) | poly(2-ethyl-2-oxazoline) | Pluronic |
| 50 | poly(vinyl alcohol) | poly(ethylene glycol) | dextran |
| 51 | poly(vinyl alcohol) | poly(ethylene glycol) | Ficoll |
| 52 | poly(vinyl alcohol) | poly(ethylene glycol) | polyacrylamide |
| 53 | poly(vinyl alcohol) | poly(ethylene glycol) | poly(diallyldimethyl ammonium chloride) |
| 54 | poly(vinyl alcohol) | poly(ethylene glycol) | dextran sulfate |
| 55 | poly(vinyl alcohol) | poly(ethylene glycol) | Tween |
| 56 | poly(vinyl alcohol) | dextran | Ficoll |
| 57 | poly(vinyl alcohol) | dextran | Tween |
| 58 | poly(vinyl alcohol) | dextran | Pluronic |
| 59 | poly(vinyl alcohol) | Ficoll | Tween |
| 60 | poly(vinyl alcohol) | Ficoll | Pluronic |
| 61 | poly(vinyl alcohol) | polyacrylamide | Tween |
| 62 | poly(vinyl alcohol) | polyacrylamide | Pluronic |
| 63 | poly(2-ethyl-2-oxazoline) | poly(ethylene glycol) | dextran |
| 64 | poly(2-ethyl-2-oxazoline) | poly(ethylene glycol) | Ficoll |
| 65 | poly(2-ethyl-2-oxazoline) | poly(ethylene glycol) | polyacrylamide |
| 66 | poly(2-ethyl-2-oxazoline) | poly(ethylene glycol) | poly(diallyldimethyl ammonium chloride) |
| 67 | poly(2-ethyl-2-oxazoline) | poly(ethylene glycol) | dextran sulfate |
| 68 | poly(2-ethyl-2-oxazoline) | poly(ethylene glycol) | polyethyleneimine |
| 69 | poly(2-ethyl-2-oxazoline) | poly(ethylene glycol) | Tween |
| 70 | poly(2-ethyl-2-oxazoline) | poly(ethylene glycol) | 1-O-Octyl-B-D-glucopyranoside |
| 71 | poly(2-ethyl-2-oxazoline) | poly(ethylene glycol) | CHAPS |
| 72 | poly(2-ethyl-2-oxazoline) | dextran | Ficoll |
| 73 | poly(2-ethyl-2-oxazoline) | dextran | Tween |
| 74 | poly(2-ethyl-2-oxazoline) | dextran | Triton |
| 75 | poly(2-ethyl-2-oxazoline) | dextran | Pluronic |
| 76 | poly(2-ethyl-2-oxazoline) | dextran | CHAPS |
| 77 | poly(2-ethyl-2-oxazoline) | Ficoll | polyethyleneimine |
| 78 | poly(2-ethyl-2-oxazoline) | Ficoll | Brij |
| 79 | poly(2-ethyl-2-oxazoline) | Ficoll | Tween |
| 80 | poly(2-ethyl-2-oxazoline) | Ficoll | Triton |

-continued

| Number | Phase component combinations | | |
|---|---|---|---|
| 81 | poly(2-ethyl-2-oxazoline) | Ficoll | Pluronic |
| 82 | poly(2-ethyl-2-oxazoline) | Ficoll | CHAPS |
| 83 | poly(2-ethyl-2-oxazoline) | polyacrylamide | polyethyleneimine |
| 84 | poly(2-ethyl-2-oxazoline) | polyacrylamide | Tween |
| 85 | poly(2-ethyl-2-oxazoline) | polyacrylamide | Triton |
| 86 | poly(2-ethyl-2-oxazoline) | polyacrylamide | Pluronic |
| 87 | poly(2-ethyl-2-oxazoline) | polyacrylamide | CHAPS |
| 88 | poly(2-ethyl-2-oxazoline) | dextran sulfate | poly(styrene sulfonic acid) |
| 89 | poly(2-ethyl-2-oxazoline) | polyethyleneimine | 1-O-Octyl-B-D-glucopyranoside |
| 90 | poly(2-ethyl-2-oxazoline) | polyethyleneimine | Pluronic |
| 91 | poly(2-ethyl-2-oxazoline) | polyethyleneimine | CHAPS |
| 92 | poly(2-ethyl-2-oxazoline) | Pluronic F68 | CHAPS |
| 93 | poly(ethylene glycol) | dextran | Ficoll |
| 94 | poly(ethylene glycol) | dextran | polyvinylpyrrolidone |
| 95 | poly(ethylene glycol) | dextran | Tween |
| 96 | poly(ethylene glycol) | dextran | CHAPS |
| 97 | poly(ethylene glycol) | Ficoll | polyethyleneimine |
| 98 | poly(ethylene glycol) | Ficoll | Tween |
| 99 | poly(ethylene glycol) | Ficoll | CHAPS |
| 100 | poly(ethylene glycol) | polyacrylamide | polyethyleneimine |
| 101 | poly(ethylene glycol) | polyacrylamide | Tween |
| 102 | poly(ethylene glycol) | polyacrylamide | CHAPS |
| 103 | poly(ethylene glycol) | polyethyleneimine | 1-O-Octyl-B-D-glucopyranoside |
| 104 | poly(ethylene glycol) | polyethyleneimine | CHAPS |
| 105 | dextran | Ficoll | hydroxyethyl cellulose |
| 106 | dextran | Ficoll | Tween |
| 107 | dextran | Ficoll | Triton |
| 108 | dextran | Ficoll | Pluronic |
| 109 | dextran | Ficoll | CHAPS |
| 110 | dextran | polyvinylpyrrolidone | poly(2-acrylamido-2-methyl-1-propanesulfonic acid) |
| 111 | dextran | hydroxyethyl cellulose | Tween |
| 112 | dextran | hydroxyethyl cellulose | Triton |
| 113 | dextran | Pluronic F68 | CHAPS |
| 114 | Ficoll | polyethyleneimine | Pluronic |
| 115 | Ficoll | polyethyleneimine | CHAPS |
| 116 | Ficoll | hydroxyethyl cellulose | Tween |
| 117 | Ficoll | hydroxyethyl cellulose | Triton |
| 118 | Ficoll | Pluronic F68 | CHAPS |
| 119 | polyacrylamide | polyethyleneimine | Pluronic |
| 120 | polyacrylamide | polyethyleneimine | CHAPS |
| 121 | polyacrylamide | Pluronic F68 | CHAPS |
| 122 | polyethyleneimine | Pluronic F68 | CHAPS |
| 123 | PEOZ | PEG | PVPNO |
| 124 | PEOZ | PEI | PVPNO |
| 125 | PEOZ | PA | PVPNO |
| 126 | PEOZ | PMAA | PVPNO |
| 127 | PEG | PEI | PVPNO |
| 128 | PEG | PMAA | PVPNO |
| 129 | PEG | PA | PVPNO |
| 130 | PEI | PA | PVPNO |
| 131 | PEI | PMAA | PVPNO |
| 132 | PA | PMAA | PVPNO |
| 133 | PEOZ | PEG | PVPNO |
| 134 | PEOZ | TWEEN | PVPNO |
| 135 | PEOZ | PA | PVPNO |
| 136 | PEOZ | PMAA | PVPNO |
| 137 | PEG | TWEEN | PVPNO |
| 138 | TWEEN | PA | PVPNO |
| 139 | TWEEN | PMAA | PVPNO |
| 140 | PA | PMAA | PVPNO |
| 141 | PEG | PA | PVPNO |
| 142 | PEG | PMAA | PVPNO |

In yet another aspect, an aqueous four-phase system is described, comprising:
a phase-separated solution comprising four aqueous phases, wherein each of the phases comprises a phase component and has a different density and the phases, taken together, represent a density gradient, and wherein the phase component combination of the four phases selected from the group consisting of:

| Number | Phase component combinations | | | |
|---|---|---|---|---|
| 1 | poly(methacrylic acid) | poly(2-ethyl-2-oxazoline) | poly(ethylene glycol) | Ficoll |
| 2 | poly(methacrylic acid) | poly(2-ethyl-2-oxazoline) | poly(ethylene glycol) | polyacrylamide |
| 3 | poly(methacrylic acid) | poly(2-ethyl-2-oxazoline) | poly(ethylene glycol) | poly(diallyldimethyl ammonium chloride |
| 4 | poly(methacrylic acid) | poly(2-ethyl-2-oxazoline) | poly(ethylene glycol) | polyethyleneimine |

-continued

| Number | Phase component combinations | | | |
|---|---|---|---|---|
| 5 | poly(methacrylic acid) | poly(2-ethyl-2-oxazoline) | poly(ethylene glycol) | Tween 20 |
| 6 | poly(methacrylic acid) | poly(2-ethyl-2-oxazoline) | poly(ethylene glycol) | 1-O-Octyl-B-D-glucopyranoside |
| 7 | poly(methacrylic acid) | poly(2-ethyl-2-oxazoline) | poly(ethylene glycol) | CHAPS |
| 8 | poly(methacrylic acid) | poly(2-ethyl-2-oxazoline) | Ficoll | polyethyleneimine |
| 9 | poly(methacrylic acid) | poly(2-ethyl-2-oxazoline) | Ficoll | Tween |
| 10 | poly(methacrylic acid) | poly(2-ethyl-2-oxazoline) | Ficoll | Triton |
| 11 | poly(methacrylic acid) | poly(2-ethyl-2-oxazoline) | Ficoll | Pluronic |
| 12 | poly(methacrylic acid) | poly(2-ethyl-2-oxazoline) | Ficoll | CHAPS |
| 13 | poly(methacrylic acid) | poly(2-ethyl-2-oxazoline) | polyacrylamide | polyethyleneimine |
| 14 | poly(methacrylic acid) | poly(2-ethyl-2-oxazoline) | polyacrylamide | Tween |
| 15 | poly(methacrylic acid) | poly(2-ethyl-2-oxazoline) | polyacrylamide | Triton |
| 16 | poly(methacrylic acid) | poly(2-ethyl-2-oxazoline) | polyacrylamide | Pluronic |
| 17 | poly(methacrylic acid) | poly(2-ethyl-2-oxazoline) | polyacrylamide | CHAPS |
| 18 | poly(methacrylic acid) | poly(2-ethyl-2-oxazoline) | polyethyleneimine | 1-O-Octyl-B-D-glucopyranoside |
| 19 | poly(methacrylic acid) | poly(2-ethyl-2-oxazoline) | polyethyleneimine | Pluronic |
| 20 | poly(methacrylic acid) | poly(2-ethyl-2-oxazoline) | polyethyleneimine | CHAPS |
| 21 | poly(methacrylic acid) | poly(2-ethyl-2-oxazoline) | Pluronic F68 | CHAPS |
| 22 | poly(methacrylic acid) | poly(ethylene glycol) | Ficoll | polyethyleneimine |
| 23 | poly(methacrylic acid) | poly(ethylene glycol) | Ficoll | Tween |
| 24 | poly(methacrylic acid) | poly(ethylene glycol) | Ficoll | CHAPS |
| 25 | poly(methacrylic acid) | poly(ethylene glycol) | polyacrylamide | polyethyleneimine |
| 26 | poly(methacrylic acid) | poly(ethylene glycol) | polyacrylamide | Tween |
| 27 | poly(methacrylic acid) | poly(ethylene glycol) | polyacrylamide | CHAPS |
| 28 | poly(methacrylic acid) | poly(ethylene glycol) | polyethyleneimine | 1-O-Octyl-B-D-glucopyranoside |
| 29 | poly(methacrylic acid) | poly(ethylene glycol) | polyethyleneimine | CHAPS |
| 30 | poly(methacrylic acid) | Ficoll | polyethyleneimine | Pluronic |
| 31 | poly(methacrylic acid) | Ficoll | polyethyleneimine | CHAPS |
| 32 | poly(methacrylic acid) | Ficoll | Pluronic F68 | CHAPS |
| 33 | poly(methacrylic acid) | polyacrylamide | polyethyleneimine | Pluronic |
| 34 | poly(methacrylic acid) | polyacrylamide | polyethyleneimine | CHAPS |
| 35 | poly(methacrylic acid) | polyacrylamide | Pluronic | CHAPS |
| 36 | poly(methacrylic acid) | polyethyleneimine | Pluronic | CHAPS |
| 37 | poly(vinyl alcohol) | poly(2-ethyl-2-oxazoline) | poly(ethylene glycol) | dextran |
| 38 | poly(vinyl alcohol) | poly(2-ethyl-2-oxazoline) | poly(ethylene glycol) | Ficoll |
| 39 | poly(vinyl alcohol) | poly(2-ethyl-2-oxazoline) | poly(ethylene glycol) | polyacrylamide |
| 40 | poly(vinyl alcohol) | poly(2-ethyl-2-oxazoline) | poly(ethylene glycol) | poly(diallyldimethyl ammonium chloride |
| 41 | poly(vinyl alcohol) | poly(2-ethyl-2-oxazoline) | poly(ethylene glycol) | dextran sulfate |
| 42 | poly(vinyl alcohol) | poly(2-ethyl-2-oxazoline) | poly(ethylene glycol) | Tween |
| 43 | poly(vinyl alcohol) | poly(2-ethyl-2-oxazoline) | dextran | Ficoll |
| 44 | poly(vinyl alcohol) | poly(2-ethyl-2-oxazoline) | dextran | Tween |
| 45 | poly(vinyl alcohol) | poly(2-ethyl-2-oxazoline) | dextran | Pluronic |
| 46 | poly(vinyl alcohol) | poly(2-ethyl-2-oxazoline) | Ficoll | Tween |
| 47 | poly(vinyl alcohol) | poly(2-ethyl-2-oxazoline) | Ficoll | Pluroni |
| 48 | poly(vinyl alcohol) | poly(2-ethyl-2-oxazoline) | polyacrylamide | Tween |
| 49 | poly(vinyl alcohol) | poly(2-ethyl-2-oxazoline) | polyacrylamide | Pluronic |
| 50 | poly(vinyl alcohol) | poly(ethylene glycol) | dextran | Ficoll |
| 51 | poly(vinyl alcohol) | poly(ethylene glycol) | dextran | Tween |
| 52 | poly(vinyl alcohol) | poly(ethylene glycol) | Ficoll | Tween |
| 53 | poly(vinyl alcohol) | poly(ethylene glycol) | polyacrylamide | Tween |
| 54 | poly(vinyl alcohol) | dextran | Ficoll | Tween |
| 55 | poly(vinyl alcohol) | dextran | Ficoll | Pluronic |
| 56 | poly(2-ethyl-2-oxazoline) | poly(ethylene glycol) | dextran | Ficoll |
| 57 | poly(2-ethyl-2-oxazoline) | poly(ethylene glycol) | dextran | Tween |
| 58 | poly(2-ethyl-2-oxazoline) | poly(ethylene glycol) | dextran | CHAPS |
| 59 | poly(2-ethyl-2-oxazoline) | poly(ethylene glycol) | Ficoll | polyethyleneimine |
| 60 | poly(2-ethyl-2-oxazoline) | poly(ethylene glycol) | Ficoll | Tween |
| 61 | poly(2-ethyl-2-oxazoline) | poly(ethylene glycol) | Ficoll | CHAPS |
| 62 | poly(2-ethyl-2-oxazoline) | poly(ethylene glycol) | polyacrylamide | polyethyleneimine |
| 63 | poly(2-ethyl-2-oxazoline) | poly(ethylene glycol) | polyacrylamide | Tween |
| 64 | poly(2-ethyl-2-oxazoline) | poly(ethylene glycol) | polyacrylamide | CHAPS |
| 65 | poly(2-ethyl-2-oxazoline) | poly(ethylene glycol) | polyethyleneimine | 1-O-Octyl-B-D-glucopyranoside |
| 66 | poly(2-ethyl-2-oxazoline) | poly(ethylene glycol) | polyethyleneimine | CHAPS |
| 67 | poly(2-ethyl-2-oxazoline) | dextran | Ficoll | Tween |
| 68 | poly(2-ethyl-2-oxazoline) | dextran | Ficoll | Triton |
| 69 | poly(2-ethyl-2-oxazoline) | dextran | Ficoll | Pluronic |
| 70 | poly(2-ethyl-2-oxazoline) | dextran | Ficoll | CHAPS |
| 71 | poly(2-ethyl-2-oxazoline) | dextran | Pluronic F68 | CHAPS |
| 72 | poly(2-ethyl-2-oxazoline) | Ficoll | polyethyleneimine | Pluronic |
| 73 | poly(2-ethyl-2-oxazoline) | Ficoll | polyethyleneimine | CHAPS |
| 74 | poly(2-ethyl-2-oxazoline) | Ficoll | Pluronic F68 | CHAPS |
| 75 | poly(2-ethyl-2-oxazoline) | polyacrylamide | polyethyleneimine | Pluronic |
| 76 | poly(2-ethyl-2-oxazoline) | polyacrylamide | polyethyleneimine | CHAPS |
| 77 | poly(2-ethyl-2-oxazoline) | polyacrylamide | Pluronic F68 | CHAPS |
| 78 | poly(2-ethyl-2-oxazoline) | polyethyleneimine | Pluronic F68 | CHAPS |
| 79 | poly(ethylene glycol) | dextran | Ficoll | Tween |
| 80 | poly(ethylene glycol) | dextran | Ficoll | CHAPS |
| 81 | poly(ethylene glycol) | Ficoll | polyethyleneimine | CHAPS |

-continued

| Number | Phase component combinations | | | |
|---|---|---|---|---|
| 82 | poly(ethylene glycol) | polyacrylamide | polyethyleneimine | CHAPS |
| 83 | dextran | Ficoll | hydroxyethyl cellulose | Tween |
| 84 | dextran | Ficoll | hydroxyethyl cellulose | Triton |
| 85 | dextran | Ficoll | Pluronic | CHAPS |
| 86 | Ficoll | polyethyleneimine | Pluronic | CHAPS |
| 87 | polyacrylamide | polyethyleneimine | Pluronic | CHAPS |
| 88 | PEOZ | PEG | PEI | PVPNO |
| 89 | PEOZ | PEG | PA | PVPNO |
| 90 | PEOZ | PEI | PA | PVPNO |
| 91 | PEOZ | PEI | PMAA | PVPNO |
| 92 | PEOZ | PA | PMAA | PVPNO |
| 93 | PEG | PEI | PA | PVPNO |
| 94 | PEG | PEI | PMAA | PVPNO |
| 95 | PEG | PA | PMAA | PVPNO |
| 96 | PEI | PA | PMAA | PVPNO |
| 97 | PEOZ | PEG | PMAA | PVPNO |
| 98 | PEOZ | PEG | PA | PVPNO |
| 99 | PEOZ | PEG | TWEEN | PVPNO |
| 100 | PEOZ | TWEEN | PA | PVPNO |
| 101 | PEOZ | TWEEN | PMAA | PVPNO |
| 102 | PEOZ | PA | PMAA | PVPNO |
| 103 | PEG | TWEEN | PA | PVPNO |
| 104 | PEG | TWEEN | PMAA | PVPNO |
| 105 | PEG | PA | PMAA | PVPNO |
| 106 | TWEEN | PA | PMAA | PVPNO |

In yet another aspect, an aqueous five-phase system is described, comprising:

a phase-separated solution comprising five aqueous phases, wherein each of the phases comprises a phase component and has a different density and the phases, taken together, represent a density gradient, and wherein the phase component combination of the five phases is selected from the group consisting of:

| number | Phase component combinations | | | | |
|---|---|---|---|---|---|
| 1 | poly(vinyl alcohol) | poly(2-ethyl-2-oxazoline) | poly(ethylene glycol) | dextran | Ficoll |
| 2 | poly(methacrylic acid) | poly(2-ethyl-2-oxazoline) | poly(ethylene glycol) | Ficoll | polyethyleneimine |
| 3 | poly(methacrylic acid) | poly(2-ethyl-2-oxazoline) | poly(ethylene glycol) | polyacrylamide | polyethyleneimine |
| 4 | poly(vinyl alcohol) | poly(2-ethyl-2-oxazoline) | poly(ethylene glycol) | dextran | Tween |
| 5 | poly(methacrylic acid) | poly(2-ethyl-2-oxazoline) | poly(ethylene glycol) | Ficoll | Tween |
| 6 | poly(vinyl alcohol) | poly(2-ethyl-2-oxazoline) | poly(ethylene glycol) | Ficoll | Tween |
| 7 | poly(vinyl alcohol) | poly(2-ethyl-2-oxazoline) | dextran | Ficoll | Tween |
| 8 | poly(vinyl alcohol) | poly(ethylene glycol) | dextran | Ficoll | Tween |
| 9 | poly(2-ethyl-2-oxazoline) | poly(ethylene glycol) | dextran | Ficoll | Tween |
| 10 | poly(methacrylic acid) | poly(2-ethyl-2-oxazoline) | poly(ethylene glycol) | polyacrylamide | Tween |
| 11 | poly(vinyl alcohol) | poly(2-ethyl-2-oxazoline) | poly(ethylene glycol) | polyacrylamide | Tween |
| 12 | poly(methacrylic acid) | poly(2-ethyl-2-oxazoline) | poly(ethylene glycol) | polyethyleneimine | 1-O-Octyl-B-D-glucopyranoside |
| 13 | poly(vinyl alcohol) | poly(2-ethyl-2-oxazoline) | dextran | Ficoll | Pluronic |
| 14 | poly(methacrylic acid) | poly(2-ethyl-2-oxazoline) | Ficoll | polyethyleneimine | Pluronic |
| 15 | poly(methacrylic acid) | poly(2-ethyl-2-oxazoline) | polyacrylamide | polyethyleneimine | Pluronic |
| 16 | poly(methacrylic acid) | poly(2-ethyl-2-oxazoline) | poly(ethylene glycol) | Ficoll | CHAPS |
| 17 | poly(2-ethyl-2-oxazoline) | poly(ethylene glycol) | dextran | Ficoll | CHAPS |
| 18 | poly(methacrylic acid) | poly(2-ethyl-2-oxazoline) | poly(ethylene glycol) | polyacrylamide | CHAPS |
| 19 | poly(methacrylic acid) | poly(2-ethyl-2-oxazoline) | poly(ethylene glycol) | polyethyleneimine | CHAPS |
| 20 | poly(methacrylic acid) | poly(2-ethyl-2-oxazoline) | Ficoll | polyethyleneimine | CHAPS |
| 21 | poly(methacrylic acid) | poly(ethylene glycol) | Ficoll | polyethyleneimine | CHAPS |
| 22 | poly(2-ethyl-2-oxazoline) | poly(ethylene glycol) | Ficoll | polyethyleneimine | CHAPS |
| 23 | poly(methacrylic acid) | poly(2-ethyl-2-oxazoline) | polyacrylamide | polyethyleneimine | CHAPS |
| 24 | poly(methacrylic acid) | poly(ethylene glycol)' | polyacrylamide | polyethyleneimine | CHAPS |
| 25 | poly(2-ethyl-2-oxazoline) | poly(ethylene glycol) | polyacrylamide | polyethyleneimine | CHAPS |
| 26 | poly(methacrylic acid) | poly(2-ethyl-2-oxazoline) | Ficoll | Pluronic | CHAPS |
| 27 | poly(2-ethyl-2-oxazoline) | dextran | Ficoll | Pluronic | CHAPS |
| 28 | poly(methacrylic acid) | poly(2-ethyl-2-oxazoline) | polyacrylamide | Pluronic | CHAPS |
| 29 | poly(methacrylic acid) | poly(2-ethyl-2-oxazoline) | polyethyleneimine | Pluronic | CHAPS |
| 30 | poly(methacrylic acid) | Ficoll | polyethyleneimine | Pluronic | CHAPS |
| 31 | poly(2-ethyl-2-oxazoline) | Ficoll | polyethyleneimine | Pluronic | CHAPS |
| 32 | poly(methacrylic acid) | polyacrylamide | polyethyleneimine | Pluronic | CHAPS |
| 33 | poly(2-ethyl-2-oxazoline) | polyacrylamide | polyethyleneimine | Pluronic | CHAPS |
| 34 | PEG | PEI | PA | PMAA | PVPNO |
| 35 | PEOZ | PEI | PA | PMAA | PVPNO |
| 36 | PEOZ | PEG | PA | PMAA | PVPNO |
| 37 | PEOZ | PEG | PEI | PMAA | PVPNO |
| 38 | PEOZ | PEG | PEI | PA | PVPNO |
| 39 | PEOZ | PEG | PEI | PA | PMAA |
| 40 | PEG | TWEEN | PA | PMAA | PVPNO |

-continued

| number | Phase component combinations | | | | |
|---|---|---|---|---|---|
| 41 | PEOZ | TWEEN | PA | PMAA | PVPNO |
| 42 | PEOZ | PEG | TWEEN | PMAA | PVPNO |
| 43 | PEOZ | PEG | TWEEN | PA | PVPNO |
| 44 | PEOZ | PEG | TWEEN | PA | PMAA |

In yet another aspect, an aqueous six-phase system is described, comprising:

a phase-separated solution comprising six aqueous phases, wherein each of the phases comprises a phase component and has a different density and the phases, taken together, represent a density gradient, and wherein the phase component combination of the six phases is selected from the group consisting of:

| number | Phase component combinations | | | | | |
|---|---|---|---|---|---|---|
| 1 | poly(vinyl alcohol) | poly(2-ethyl-2-oxazoline) | poly(ethylene glycol) | dextran | Ficoll | Tween |
| 2 | PMAA | PEOZ | PEG | Ficoll | PEI | CHAPS |
| 3 | PMAA | PEOZ | PEG | PA | PEI | CHAPS |
| 4 | PMAA | PEOZ | PEI | Ficoll | CHAPS | Pluronic |
| 5 | PMAA | PEOZ | PA | PEI | Pluronic | CHAPS |
| 6 | PEOZ | PEG | PEI | PA | PMAA | PVPNO |
| 7 | PEOZ | PEG | TWEEN | PA | PMAA | PVPNO |

In yet another aspect, a non-aqueous two-phase system is described, comprising:

two phase-separated non-aqueous phases, wherein each of the phases comprises a phase component and has a different density and the phases, taken together, represent a density gradient, and wherein the phase component combination of the two phases is selected from the group consisting of:
poly(bisphenol A carbonate)-polydimethylsiloxane, poly(bisphenol A carbonate)-polystyrene,
poly(bisphenol A carbonate)-poly(4-vinylpyridine), poly(bisphenol A carbonate)-poly(2-ethyl-2-oxazoline), poly(bisphenol A carbonate)-polycaprolactone, polydimethylsiloxane-polystyrene, polydimethylsiloxane-poly(4-vinylpyridine), polydimethylsiloxane-poly(2-ethyl-2-oxazoline), polydimethylsiloxane-polycaprolactone, polystyrene-poly(4-vinylpyridine),
polystyrene-poly(2-ethyl-2-oxazoline), polystyrene-polycaprolactone, poly(4-vinylpyridine)-poly(2-ethyl-2-oxazoline), poly(4-vinylpyridine)-polycaprolactone, poly(2-ethyl-2-oxazoline)-polycaprolactone, PPG-PEG, PPG-PL; PPG-PDMS; PPG-PBD; PEG-PL; PEG-PDMS; PEG-PEVE; PEG-PBD; PL-PDMS; PL-PBD; PDMS-PEVE; PDMS-PBD; and PEVE-PBD.

In yet another aspect, a non-aqueous three-phase system is described, comprising:

three phase-separated non-aqueous phases, wherein each of the phases comprises a phase component and has a different density and the phases, taken together, represent a density gradient, and wherein the phase component combination of the three phases is selected from the group consisting of:
poly(bisphenol A carbonate)-polydimethylsiloxane-polystyrene, poly(bisphenol A carbonate)-polydimethylsiloxane-poly(4-vinylpyridine), poly(bisphenol A carbonate)-polydimethylsiloxane-poly(2-ethyl-2-oxazoline, poly(bisphenol A carbonate)-polydimethylsiloxane-polycaprolactone, poly(bisphenol A carbonate)-polystyrene-poly(4-vinylpyridine), poly(bisphenol A carbonate)-polystyrene-poly(2-ethyl-2-oxazoline), poly(bisphenol A carbonate)-polystyrene-polycaprolactone, poly(bisphenol A carbonate)-poly(4-vinylpyridine)-poly(2-ethyl-2-oxazoline), poly(bisphenol A carbonate)-poly(4-vinylpyridine)-polycaprolactone, poly(bisphenol A carbonate)-poly(2-ethyl-2-oxazoline)-polycaprolactone, poly dimethylsiloxane-poly styrene-poly(4-vinylpyridine), poly dimethylsiloxane-poly styrene-poly(2-ethyl-2-oxazoline), polydimethylsiloxane-polystyrene-polycaprolactone, polydimethylsiloxane-poly(4-vinylpyridine)-poly(2-ethyl-2-oxazoline), poly dimethylsiloxane-poly(4-vinylpyridine)-poly caprolactone, polydimethylsiloxane-poly(2-ethyl-2-oxazoline)-polycaprolactone, polystyrene-poly(4-vinylpyridine)-poly(2-ethyl-2-oxazoline), polystyrene-poly(4-vinylpyridine)-polycaprolactone, polystyrene-poly(2-ethyl-2-oxazoline)-polycaprolactone, poly(4-vinylpyridine)-poly(2-ethyl-2-oxazoline)-polycaprolactone. PPG-PEG-PL; PPG-PDMS-PBD; PPG-PEG-PBD; PEG-PEVE-PBD; PEG-PEVE-PDMS; PPG-PEG-PDMS; PEG-PL-PDMS; PEG-PL-PBD; PL-PDMS-PBD; and PDMS-PEVE-PBD.

In yet another aspect, a non-aqueous four-phase system is described, comprising:

four phase-separated non-aqueous phases, wherein each of the phases comprises a phase component and has a different density and the phases, taken together, represent a density gradient, and wherein the phase component combination of the four phases is selected from the group consisting of:
poly(bisphenol A carbonate)-polydimethylsiloxane-polystyrene-poly(4-vinylpyridine), poly(bisphenol A carbonate)-polydimethylsiloxane-polystyrene-poly(2-ethyl-2-oxazoline),
poly(bisphenol A carbonate)-polydimethylsiloxane-polystyrene-polycaprolactone, poly(bisphenol A carbonate)-polydimethylsiloxane-poly(4-vinylpyridine)-poly(2-ethyl-2-oxazoline), poly(bisphenol A carbonate)-polydimethylsiloxane-poly(4-vinylpyridine) polycaprolactone, poly(bisphenol A carbonate)-polydimethylsiloxane-poly(2-ethyl-2-oxazoline)-polycaprolactone, poly(bisphenol A carbonate)-polystyrene-poly(4-vinylpyridine)-poly(2-ethyl-2-oxazoline), poly(bisphenol A carbonate)-polystyrene-poly(4-vinylpyridine)-polycaprolactone, poly(bisphenol A carbonate)-polystyrene-poly(2-ethyl-2-oxazoline)-poly-caprolactone, poly(bisphenol A carbonate)-poly(4-vinylpyridine)-poly(2-ethyl-2-oxazoline)-polycaprolactone, polydimethylsiloxane-polystyrene-poly(4-vinylpyridine)-poly(2-ethyl-2-oxazoline), polydimethylsiloxane-polystyrene-poly(4-vinylpyridine)-polycaprolactone, polydimethylsiloxane-polystyrene-poly(2-ethyl-2-oxazoline)-polycaprolactone, polydimethylsiloxane-poly(4-vinylpyridine)-poly(2-ethyl-2-oxazoline)-polycaprolactone, polystyrene-poly(4-vinylpyridine)-poly(2-ethyl-2-oxazoline)-polycaprolactone, PPG-PEG-PL-PDMS; PPG-PEG-PL-PBD; PPG-PEG-PDMS-PBD; PPG-PL-PDMS-PBD; and PEG-PL-PDMS-PBD.

In yet another aspect, a non-aqueous five-phase system is described, comprising:

five phase-separated non-aqueous phases, wherein each of the phases comprises a phase component and has a different density and the phases, taken together, represent a density gradient, and wherein the phase component combination of the five phases is selected from the group consisting of: poly(bisphenol A carbonate)-polydimethylsiloxane-polystyrene-poly(4-vinylpyridine)-poly(2-ethyl-2-oxazoline), poly(bisphenol A carbonate)-polydimethylsiloxane-polystyrene-polycaprolactone, poly(bisphenol A carbonate)-polydimethylsiloxane-polystyrene-poly(2-ethyl-2-oxazoline)-polycaprolactone, poly(bisphenol. A carbonate)-polydimethylsiloxane-poly(4-vinylpyridine)-poly(2-ethyl-2-oxazoline)-polycaprolactone, poly(bisphenol A carbonate)-polystyrene-poly(4-vinylpyridine)-poly(2-ethyl-2-oxazoline)-polycaprolactone, polydimethylsiloxane-polystyrene-poly(4-vinylpyridine)-poly(2-ethyl-2-oxazoline)-polycaprolactone, and PPG-PEG-PL-PDMS-PBD.

In yet another aspect, a non-aqueous six-phase system is described, comprising:

a phase-separated solution comprising six non-aqueous phases, wherein each of the phases has a different density and the phases, taken together, represent a density gradient, and wherein the composition of the phases is selected from the group consisting of:
poly(bisphenol A carbonate)-polydimethylsiloxane-polystyrene-poly(4-vinylpyridine)-poly(2-ethyl-2-oxazoline)-polycaprolactone.

In yet another aspect, a kit is described, comprising:

a plurality of phase components, in one or more solvents or in their solvent-free forms, selected from the group consisting of a polymer, a surfactant and combinations thereof, wherein at least one phase component comprises a polymer, each said phase component packaged separately;

instructions for combining the plurality of phase components in one or more solvents and for preparing a phase-separated solution therefrom; and instructions for analyzing an analyte the phase-separated solution.

In yet another aspect, a method of analyzing or separating a sample is described, comprising:

providing a phase-separated system comprising at least two phases, wherein the at least two phases each comprises a phase component selected from the group consisting of a polymer, a surfactant and combinations thereof, wherein at least one phase comprises a polymer;

each said phase has an upper and a lower phase boundary; and each of the two or more phases has a different density and the phases, taken together, represent a density gradient; and b) introducing a sample comprising one or more analytes of interest to the multi-phase system without disrupting the phase-separated solution; and c) allowing each of the analytes to migrate to a location in the phase-separated system that is characteristic of its density, wherein during migration the sample contacts one or more of the two or more phases sequentially.

In any of the preceding embodiments, greater than 80% of the analyte is located at one or more of the phase boundaries.

In any of the preceding embodiments, greater than 90% of the analyte is located at one or more of the phase boundaries.

In any of the preceding embodiments, the sample comprises a plurality of analytes and each analyte migrates to a different location in the phase-separated system.

In any of the preceding embodiments, after migration, the analyte resides at a boundary location.

In any of the preceding embodiments, the boundary location is at an interface between a phase with a density greater than the density of the analyte and a phase with a density that is less than the density of the analyte.

In any of the preceding embodiments, after migration, the analyte resides within a phase of the phase-separated system whose density matches the density of the analyte.

In any of the preceding embodiments, the analyte/phase-separated system is centrifuged to accelerate migration of the analyte.

In any of the preceding embodiments, the analyte migrates under gravitational forces.

In any of the preceding embodiments, the analyte migrates under buoyancy forces.

In any of the preceding embodiments, the phase separated system is supported in a column or test tube.

In any of the preceding embodiments, the phase separated system is supported along a filament or on a sheet.

In any of the preceding embodiments, the multi-phases are provided as dispersion or emulsion in another carrier phase.

In any of the preceding embodiments, the analyte of interest a size of more than 200 nm.

In any of the preceding embodiments, after analyte migration the phases and the analyte are in thermodynamic equilibrium.

In any of the preceding embodiments, the phase separated system comprises three or more phases.

In any of the preceding embodiments, the two or more phases comprise a common solvent which is an aqueous solvent.

In any of the preceding embodiments, the two or more phases comprise a common solvent which is an organic solvent.

In any of the preceding embodiments, the two or more phases comprise a common solvent which is a non-aqueous solvent selected from the groups consisting of liquid polymer, non-polar organic solvent, polar aprotic or protic solvent, supercritical fluid, fuel, oils, and fluorinated solvents, and combinations thereof.

In any of the preceding embodiments, the common solvent comprises dichloromethane.

In any of the preceding embodiments, the phase separated system comprises three or more phases including the two or more phases comprising a common solvent which is water and additional phase separated phases selected from the group consisting of organic solutions.

In any of the preceding embodiments, the aqueous solvent is selected from the group consisting of water, sea water, isotopes of water, buffered water, irrigation water, mine effluent, colloidal solutions, emulsions, and a combination thereof.

In any of the preceding embodiments, the analyte is selected from the group consisting of solid particles, an aggregate of particles, a liquid or gel immiscible in the solvent, a liquid crystal, crystalline materials.

In any of the preceding embodiments, the analyte is selected from the group consisting of gem, bead, metal, glass, rock, mineral, crystal, plastic, bone, rubber, paper, fabric, coal, polymer particles, gases.

In any of the preceding embodiments, the polymer is selected from the group of homopolymers, random copolymers, block copolymers, graft copolymers, ter-polymers, dendrimers, star polymers and combinations thereof.

In any of the preceding embodiments, the polymer is linear, branched and/or cross-linked.

In any of the preceding embodiments, the polymer is selected from the group consisting of dextran, dextran sulfate, chondroitin sulfate A, polysucrose, diethylaminoethyl-dextran, poly(2-vinylpyridine-N-oxide), polysucrose, poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propanesulfonic acid), poly(diallyldimethyl ammonium chloride), poly(styrene sulfonic acid), polyallylamine, alginic acid, poly(bisphenol A carbonate), polydimethylsiloxane, polystyrene, poly(4-vinylpyridine), polycaprolactone, polysulfone, poly(methyl methacrylate-co-methacrylic acid), poly(methyl methacrylate), poly(tetrahydrofuran), poly(propylene glycol), and poly(vinyl acetate) and copolymers or terpolymer thereof.

In any of the preceding embodiments, the surfactant is selected from the group consisting of polysorbate, 3-[(3-cholamidopropyl)dimethylammonio]-1-propanesulfonate, polyoxyethylene-polyoxypropylene, 1-O-Octyl-β-D-glucopyranoside, Tetramethylbutyl)phenyl-polyethylene glycol, nonylphenol polyoxyethylene, 4-(1,1,3,3-Tetramethylbutyl)phenyl-polyethylene glycol, 2-(Perfluoroalkyl)ethyl methacrylate, N,N-dimethyldodecylamine N-oxide, polyethylene glycol dodecyl ether, sodium dodecyl sulfate, sodium cholate, benzylalkonium chloride and dodecyltrimethylammonium chloride.

In any of the preceding embodiments, one or more phases further comprise an additive selected from the group consisting of a so-solvent, an acid, a base, a miscible polymer, vitamin, drug, antibiotic, small molecule, dye, and flurophore.

In any of the preceding embodiments, the sample is selected from the group consisting of forensics study sample, a sample indicative of animal health, a sample indicative of human identity used for border control, home land security, or intelligence, a sample from food processing, a sample indicative of product quality, a sample indicative of environmental safety, a sample containing different crystal polymorphs, and a combination thereof.

In any of the preceding embodiments, the phases in the multi-phases have low interfacial free energy.

In any of the preceding embodiments, the method further comprises collecting the analyte from the boundary location.

In yet another aspect, a method of determining the density of a solid particle using a multi-phase system is described, comprising:

a) providing a multi-phase system comprising two or more phases, wherein at least two of the phases each comprise a phase component selected from the group consisting of a polymer, a surfactant, and a combination thereof and at least one of the two phase comprises a polymer;

each of the two or more phases has a different density and the two or more phases, taken together, represent a density gradient; and the phases are phase-separated from each other;

b) introducing a solid particle to the multi-phase system;

c) allowing the solid particle to migrate to a location in the multiphase system that is characteristic of its density, wherein during migration the sample contacts one or more of the two or more phases sequentially; and d) determining the density of the solid particle, wherein the solid particle resides in an interface between two adjacent phases and the density of the solid particle is calculated based on the position of the solid particle, the buoyancy, and the interfacial tension between the two phases.

In any of the preceding embodiments, the solid particle's density is determined by using the equation that gravity of the solid particle ($F_g$; N)=buoyancy ($F_B$; N)+ the interfacial tension ($F_f$; N).

In yet another aspect, a method of creating a multi-phase system is described, comprising:

identifying a two-phase system comprising a first phase comprising a first polymer and a second phase comprising a second polymer, wherein the first and second phases are and phase-separated from each other; and introducing a third phase comprising a copolymer of the first and second polymers to the two-phase system; wherein the copolymer is formed by polymerization of the monomers of the first and second polymers, and the first, second, and third phase are phase-separated from each other.

In any of the preceding embodiments, the first, second, and third phases are each organic or each aqueous.

In yet another aspect, a method of analyzing an analyte is described, comprising:

mixing a sample containing an analyte of interest and a plurality of phase components in an appropriate solvent as set forth in the multi-phase system of any one of the preceding embodiments;

allowing the mixture to phase separate, wherein the analyte interacts with all of phase components during phase separate, wherein the analyte preferentially resides in one phase based on the analyte's affinity to that phase.

In yet another aspect, a method of preparing a multi-phase system is described, comprising:

mixing at least a substantially pure first and second phase components and a common solvent to form a mixture, wherein the first and second phase components are each selected from the group consisting of a polymer, a surfactant, and a combination thereof and at least of the first and second phase components is a polymer; and allowing the mixture to phase-separate to form a multi-phase system comprising at least:

a first phase comprising the first phase component; and a second phase comprising the second phase component; wherein the first and second phase are in contact and phase-separate from each other.

In any of the preceding embodiments, the method further comprises shaking or stirring the mixture.

In any of the preceding embodiments, the common solvent is aqueous or organic.

In yet another aspect, a method of the broadening the density range of an existing multi-phase system is described, comprising:

providing an existing multi-phase system comprising two or more phases including at least a top phase and a bottom phase at the top and bottom of the existing multi-phase system, respectively, and a first and second phases. wherein
the first and second phases are in contact, phase-separated from each other, and each comprising a phase component selected from the group consisting of a polymer, a surfactant, and a combination thereof;
at least one of the first and second phases comprising a polymer;
each of the two or more phases has a different density and the two or more phases, taken together, represent a density gradient;
adding, to the existing multi-phase system, one or more additional phase(s) with densities lower than the top phase of the existing multi-phase system; and
allowing the additional phase(s) and the existing multi-phase system to phase-separate to form a new multi-phase system.

In yet another aspect, a method of the broadening the density range of an existing multi-phase system is described, comprising:
providing an existing multi-phase system comprising two or more phases including at least a top phase and a bottom phase at the top and bottom of the existing multi-phase system, respectively, and a first and second phases. wherein
the first and second phases share a common solvent, phase-separated from each other, and each comprising a phase component selected from the group consisting of a polymer, a surfactant, and a combination thereof;
at least one of the first and second phases comprising a polymer;
each of the two or more phases has a different density and the two or more phases, taken together, represent a density gradient;
adding, to the existing multi-phase system, one or more additional phase(s) with densities higher than the bottom phase of the existing multi-phase system; and
allowing the additional phase(s) and the existing multi-phase system to phase-separate to form a new multi-phase system.

In any of the preceding embodiments, the additional phase is aqueous or organic.

In any of the preceding embodiments, the additional phase comprises a phase component selected from the group consisting of a polymer, a surfactant, and a combination thereof.

In yet another aspect, a method of the shifting the density range of an existing multi-phase system is described, comprising:
providing an existing multi-phase system comprising two or more phases comprising a common solvent and including at least a first and second phases, wherein
the first and second phases share a common solvent, phase-separated from each other, and each comprising a phase component selected from the group consisting of a polymer, a surfactant, and a combination thereof;
at least one of the first and second phases comprising a polymer;
each of the two or more phases has a different density and the two or more phases, taken together, represent a density gradient;
adding, to the existing multi-phase system, one or more additive(s) with densities higher or lower than the common solvent to form a mixture; and
allowing the mixture to phase-separate to form a new multi-phase system with a density range different from that of the existing multi-phase system.

In any of the preceding embodiments, the additive is a co-solvent mixable with the common solvent.

In any of the preceding embodiments, the additive is a salt soluble in the common solvent.

In any of the preceding embodiments, one or more phases are a solvent-free liquid polymer phase.

BRIEF DESCRIPTION OF THE DRAWING

The subject matter is described with reference to the following figures, which are presented for the purpose of illustration only and are not intended to be limiting of the invention.

FIG. 1 is plot of the miscibility characteristics of binary mixtures of aqueous polymer solutions, in which light gray indicates miscible binary systems, dark gray indicates immiscible binary systems and black represents incompatible binary systems.

FIG. 5 illustrates dichloromethane-polymer-polymer ternary mixtures, categorized as either biphasic (+), homogeneous (−), or incompatible (0).

FIG. 10 B shows a selective accumulation of Allura Red in the top phase of the PEG/PMAA two-phase system.

FIG. 11A(i) shows a patterned paper with Allura red spotted in hydrophilic regions.

FIG. 11A(ii) shows the top and bottom phases of a PEG-PMAA two-phase APS spotted on two sets of hydrophilic regions on a patterned paper.

FIG. 11B shows the selective accumulation of Allura Red in the top phase of the PEG/PMAA two-phase system deposited on the hydrophilic regions of the patterned paper.

DETAILED DESCRIPTION

Introduction

Figure 2A:
FIG. 2A-2C shows images of multiphase polymer systems. A) A three-phase system comprised of poly(propylene glycol)-polyacrylamide-poly(methacrylic acid). B) A four-phase system comprised of poly(vinyl alcohol)-poly(2-ethyl-2-oxazoline)-poly(ethylene glycol)-polyacrylamide. C) A five-phase system comprised of poly(vinyl alcohol)-poly(2-ethyl-2-oxazoline)-poly(ethylene glycol)-dextran-Ficoll.

The disclosed methods are used to separate objects or impurities in samples according to the densities of the objects or impurities, relative to the densities of the phases of a MPS. Everything has a density. Thus, because the disclosed methods can be used to separate, isolate, characterize, analyze, prepare, and purify such diverse objects, the disclosed methods can be applied to many contexts. For example, the disclosed methods can be used in the forensics, security, and intelligence contexts to separate and process objects of interest from complex samples, e.g., to detect explosives residues or separate biological specimens from samples that have been contaminated by environmental debris from crime scenes. These methods can also be used monitor animal and plant health. Animal tissues and plant material can be broken down to the cellular level to detect cellular abnormalities indicative of disease and infection. Similarly, these methods can be used to detect contaminants such as pathogens, pests, heavy metals, and pesticides in drinking water and in food processing to ensure quality control.

Multi-Phase Systems

A multi-phase system comprising two or more phases is described, wherein the two or more phases include at least a first and second phases in contact with and phase-separated from each other, each of first and second phases comprises a phase component selected from the group consisting of a polymer, a surfactant, and a combination thereof, and at least one of the first and second phases comprise a polymer. Each of the two or more phases has a different density and the phases, taken together, represent a density gradient, with the density of the phases increasing from the top phase to the bottom phase of the MPS.

In some embodiments, the MPS includes at least two phases with a common solvent. In some embodiments, the multi-phase polymer system comprises at least three phases. In some embodiments, the multi-phase system comprises at least four phases. In some embodiments, the multi-phase polymer system comprises at least five phases. In some embodiments, the multi-phase polymer system comprises at least six phases. Multi-phase system with more phases are contemplated. When more than two phases are used, it is possible to include phases using different solvents. It is also possible to include phases that do not include a phase component, such as aqueous or organic solvents, liquid polymers, fluorinated liquids, liquid metals, e.g., mercury, and ionic liquids. Such variety improves the ability of the system to separate complex samples. For example, the additional phases can extend the density range of the sample, making it possible to separate or distinguish samples of higher or lower density. Non-limiting examples of liquid polymers include poly(propylene glycol) (PPG), poly(ethylene glycol) (PEG), Pluronic L121 (PL), polydimethylsiloxane (PDMS), poly(ethyl vinyl ether) (PEVE), polybutadiene (PBD).

Each of the phases of the multi-phase system comprises a phase component. The phase component is selected from the group consisting of a polymer, a surfactant, and combinations thereof.

Figure 4:
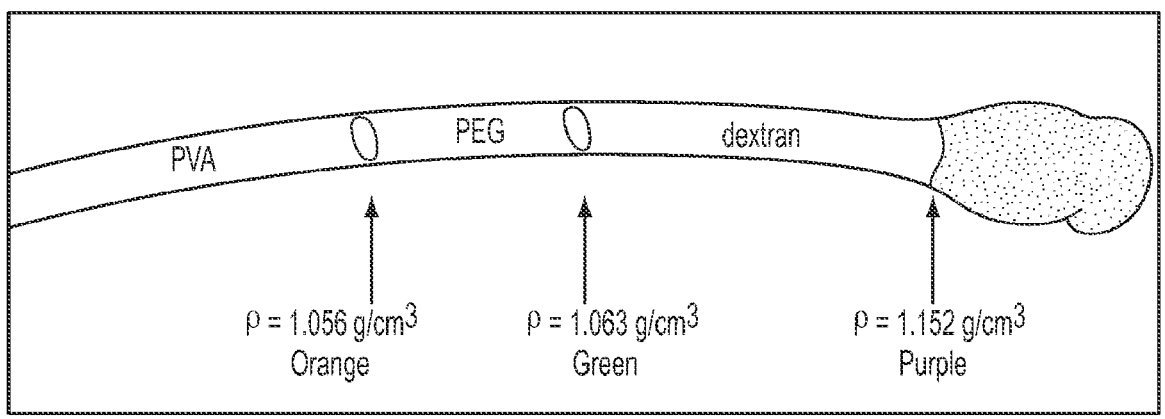
FIG. 4 shows an image of dyed density standards banding at the polymer/polymer interface of the triphasic poly(vinyl alcohol)/poly(ethylene glycol)/dextran system.

An exemplary MPS system is shown in FIG. 4. The flexible tubing contains a 3-phase multi-phase system prepared from poly(vinyl alcohol) ("PVA") ($\rho=1.056$ g/cm$^3$), poly(ethylene glycol) ("PEG") ($\rho=1.063$) and dextran ($\rho=1.152$ g/cm$^3$), all in water. PVA, the polymer of lowest density, represents the 'top' of the density gradient and dextran, the lowest. The delineation of each band can be observed from the location of colored density standard beads. Orange beads having an intermediate density between that of PVA and PEG are located at the PVA/PEG interface. Green beads having an intermediate density between that of PEG and dextran are located at the PEG/dextran interface. Purple beads that are denser than dextran sit below the dextran band. This example demonstrates the ability of the multi-phase system to distinguish between phases density variations of as little as ±0.01 g/cm$^3$. Distinctions of as little as ±0.001 g/cm$^3$ have been demonstrated.

Non-limiting examples of polymer include dextran, polysucrose (herein referred to by the trade name "Ficoll"), poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propanesulfonic acid), dextran sulfate, diethylaminoethyl-dextran, chondroitin sulfate A, poly(2-vinylpyridine-N-oxide), poly(diallyldimethyl ammonium chloride), poly(styrene sulfonic acid), polyallylamine, alginic acid, nonylphenol polyoxyethylene, poly(bisphenol A carbonate), polydimethylsiloxane, polystyrene, poly(4-vinylpyridine), polycaprolactone, polysulfone, poly(methyl methacrylate-co-methacrylic acid), poly(methyl methacrylate), poly(tetrahydrofuran), poly(propylene glycol), and poly(vinyl acetate). As used herein, a polymer includes its homopolymer, copolymer, terpolymer, block copolymer, random polymer, linear polymer, branched polymer, cross-linked polymer, and/or dendrimer system.

Non-limiting examples of surfactants include polysorbate (herein referred to by the trade name "Tween"), 3-[(3-cholamidopropyl)dimethylammonio]-1-propanesulfonate (CHAPS), polyoxyethylene-polyoxypropylene (herein referred to by the trade name "Pluronic"), 1-O-Octyl-β-D-glucopyranoside, 4-(1,1,3,3-Tetramethylbutyl)phenyl-polyethylene glycol (herein referred to by the trade name "Triton"), 2-(Perfluoroalkyl)ethyl methacrylate (herein referred to by the trade name "Zonyl"), N,N-dimethyldodecylamine N-oxide, polyethylene glycol dodecyl ether (herein referred to by the trade name "Brij"), sodium dodecyl sulfate, sodium cholate, benzylalkonium chloride and dodecyltrimethylammonium chloride. In some specific embodiments, surfactant phases comprising Pluronic and CHAPS are selected to form an aqueous multi-phase polymer system with one or more aqueous polymer phases. Non-limiting examples of the polymer used in these embodiments include poly(methacrylic acid), poly(2-ethyl-2-oxazoline), dextran, Ficoll, polyacrylamide, and polyethyleneimine. The use of the surfactant can provide additional aqueous phases and facilitate the formation of the multi-phase systems. Other appropriate surfactants to accomplish this objective can be selected by the persons of ordinary skills in the art.

The phase components are selected so that the resulting phases are phase-separated from each other. As used herein, phase-separation refers to the phenomena where two ore more solutions, each comprising a phase component, when mixed together, form the same number of distinct phases where each phase has clear boundaries and is separated from other phases. Each phase component used in the solution is selected to be soluble in the solvent of the phase, so that each resulting phase is a distinct solution of the phase component and that each phase is phase-separated from other adjacent phase(s). When the multi-phase polymer system is designed, each phase component is selected to predominantly reside in one particular phase of the multi-phase system. It should be noted that in the resulting multi-phase system, every phase can contain varying amounts of other phase components from other phases in the MPS, in addition to the selected desired phase component in that phase. Unless otherwise specified, the phase component composition in each phase of the multi-phase system recited herein generally refers to the starting phase component composition of each phase, or to the predominant phase component composition of each phase. In some embodiments, the phase component composition on a phase component comprises predominantly one phase component and small amount of one or more other phase components. In some embodiments, the phase component composition in a phase comprises more than 50% and more typically more than about 70% of one phase component. In some embodiments, the phase component composition in a polymer phase comprises more than about 75% of one phase component. In some embodiments, the phase component composition in a phase comprises more than about 80% of one phase component. In some embodiments, the phase component composition on a phase comprises more than about 85% of one phase component by weight. In some embodiments, the phase component composition on a phase comprises more than about 90% of one phase component by weight. In some embodiments, the phase component composition in a phase comprises more than about 95% of one phase component. In some embodiments, the phase component composition in a phase comprises more than about 99% of one phase component by weight. Other combinations of phase component compositions are contemplated.

In some embodiments, the concentration of the phase component in the phase is from about 0.1% to about 50% (wt/vol). In some embodiments, the concentration of the phase component in the phase is from about 0.5% to about 40% (wt/vol). In some embodiments, the concentration of the phase component in the phase is from about 1% to about 20% (wt/vol). In some embodiments, the concentration of the phase component in the phase is from about 5% to about 10% (wt/vol). In some embodiments, the concentration of the phase component in the phase is about 10% (wt/vol). In some embodiments, the concentration of the phase component in the phase is about 15% (wt/vol). In some embodiments, the composition or density of the resulting phases in the multi-phase system could be affected by the starting concentration of the phase component phases.

In some embodiments, the multi-phase system is aqueous and each phase of the MPS comprises a phase component soluble in an aqueous solvent. Non-limiting examples of aqueous solvent include water, $D_2O$, seawater, mine effluent, and irrigation water and mixtures thereof. Seawater could be used in studying small ocean organisms to keep buoyant densities close to what they are in nature. Irrigation water or mine effluent could be used to study the density effects on micro-organisms when exposed to these liquids. The analytes may also include particulate matter that could be suspended in these aqueous solutions.

In some embodiments, the aqueous multi-phase systems can comprise additional one or more organic phases comprising organic solvents. The organic phase is immiscible with and phase-separated from the aqueous polymer phases. Such additional phases are not required to have a phase component.

In some embodiments described herein, the multi-phase may comprise at least one aqueous phase. In some embodiments described herein, the multi-phase may comprise at least one organic phase. In some embodiments described herein, the multi-phase may comprise all organic phases or all aqueous phases.

In some embodiments, the aqueous multi-phase systems may be combined with one or more phases comprising organic solvents. Suitable organic solvents are those that are immiscible with water and will phase-separate from the aqueous phases.

In some embodiments, the multi-phase system is organic and each phase of the MPS comprises a phase component dissolved in an organic solvent.

In some specific embodiments, the different phases of the MPS comprise the same organic solvent. In other specific embodiments, the different phases of the MPS comprise different organic solvent.

Non-limiting examples of organic solvent include organic solvent selected from the groups consisting of liquid polymer, non-polar organic solvent, polar aprotic or protic solvent. Non-limiting examples of non-polar organic solvent include hexane and xylene. Non-limiting examples of polar aprotic organic solvent include dichloromethane and chloroform. Non-limiting examples of polar protic solvent include ethanol and methanol. Other suitable examples of organic solvents include supercritical fluid, fuel, oils, and fluorinated solvents, and combinations thereof. In some embodiments, non-limiting examples of suitable organic solvents include chloroform, dichloromethane ether, ethyl acetate, dimethylformamide, benzene, toluene, xylene, hexanes, acetonitrile, diethylether, trichloroethane, benzyl alcohol, acetone, aniline, mineral oil, perfluorinated solvents, and oils, tetrahydrofuran (THF), or water miscible solvents such as ethanol and methanol, supercritical $CO_2$, complex hydrocarbons such as fuel, and hydrophobic, high viscosity fluids such as lubricants. For instance, using fuel as a common solvent for a MPS, particulates suspended in fuel can be analyzed that are the result from engine breakdown, fuel contamination, shale/rock particulates (from freshly mined fuels), etc.

In other embodiments, the MPS comprises a liquid polymer as one of the phases. Non-limiting examples of liquid polymers include polyethyleneimine, polybutadiene, polydimethylsiloxane, poly(propylene glycol), poly(ethyl vinyl ether), cis(polyisoprene) and Tween (surfactant). Such additional phases are not required to have a phase component.

In some embodiments, the multi-phase system comprises at least an aqueous phase and at least an organic phase. Each phase may comprise a phase component and the mixture of aqueous and organic phases, taken together, represents a density gradient.

In some embodiments, one or more of the phases of the MPS are degassed to remove residual amount of gas dissolved in the phases. In some embodiments, the phases are degassed to remove oxygen from the phase to avoid possible oxidation of the sample applied onto the MPS. For example, highly viscous phases of MPS are degassed to remove any bubbles entrapped in phases or at interfaces. Degassing can also remove $H_2$, $N_2$, $CH_4$, $NH_3$, Ar, and other trace gases such as $H_2S$, and NOx. Other gases may be added (e.g., ammonia), to perform chemistry on separated species.

In some embodiments, one or more salt can be added to an aqueous multi-phase phase component system. The salts dissolve in the phase resulting in change of the phase density and typically do not partition between phases. Salts can also change the ionic strength of the solution. Non-limiting examples of salts include light or heavy salts, NaCl, NaBr, LiBr, KBr, RbBr, CsBr, and some phosphate salts. Other salts could be sodium metatungstate or manganese chloride. Non-limiting examples of salts also include sodium chloride, potassium chloride, sulfates, phosphates, nitrites, and citrates. The addition of salts can help the phase-separation process. In some embodiments, salt(s) can be added to the phase component systems in order to adjust the density, pH, and/or osmolality of the multiphase systems. In some embodiments, small molecules can be added for some specific functions. In some specific embodiments, heparin or sodium EDTA is added as an anticoagulant. In some other embodiments, sodium benzoate is added as a preservative. In other embodiments, paramagnetic salts are added to exploit magnetic properties.

In one or more embodiments, particularly multi-phase systems designed for use with more than two phase components, one or more polymers or surfactants that do not phase separate with each of the other phase components can be used as additives to modify the density, viscosity, osmolality, or refractive index of the phase component in which the additive resides. The polymers or surfactants are added to the various phases of the multi-phase system in addition to the phase components at concentrations less than is required to phase separate into a separate phase. In this instance, the surfactant performs the functions that are typical of surfactants, such as modify the surface tension of the solution.

Non-limiting examples of other additives that can be included in the phases include used in formulations to produce aggregation include, organic additives such as dyes and reactive or non-reactive dissolved gasses and cosolvents. In addition, the phases can be colloids or micelles.

Various types of form factors of the MPS can be used. In some embodiments, the MPS is contained in a tube or container, such as a test tube or flexible plastic tubing. In still other embodiments, the MPS is deposited on cloth or string. In still other embodiments, the MPS is deposited in bottle or drum or on porous films or sponges. For example, a string or porous filament can be held in a test tube during the formation of the multi-phase system, such that the phase separated domains are absorbed into the porous filament. The filament is then removed from the MPS and contains a thin layer of phase-separated domains along the length of the filament.

In some embodiments, the MPS is deposited on paper. In some embodiments, the MPS is deposited on patterned paper. Paper can be patterned using hydrophobic barrier substantially permeating the thickness of the paper, thus defining one or more hydrophilic regions on the paper. In some specific embodiments, the paper can be patterned following the procedures described in PCT Publication No. 2008/049083, the content of which is incorporated in its entirety by reference. In some specific embodiments, the MPS is aqueous and the aqueous phases of the MPS are deposited on a plurality of the hydrophilic regions on paper. By way of example, phase separation bands from an MPS column can be individually spotted on patterned regions of paper. The individual spotted regions can be stacked to recreate the density gradient in the MPS column. Alternatively, the individual spotted regions can be stacked to provide a density variation that is different from the original MPS column.

In some embodiments, the MPSs as described herein have the characteristics that, once formed, are at equilibrium: (i) the compositions and properties of the phase-separated layers do not change with time, (ii) MPS may be prepared well in advance of their use, and (iii) MPS may be reformed if perturbed or agitated.

Generally speaking, if a combination of multiple phase component phases results in a phase-separated MPS, any sub-combination of the multiple phase component phases will also result in a phase-separated MPS. Thus, if a five-phase component MPS phase-separates, any four-polymer aqueous system selected from the five phase component phases can also phase-separate. Likewise, any two- or three-phase component MPS selected from the five phase component phases can also phase-separate. Other suitable combinations of polymers are contemplated.

In some embodiments, whether or not a MPS comprising multiple phase components will phase-separate can be predicted based on the properties of the MPSs containing the sub-combination of the multiple phase components. For instance, phase solutions containing phase components A, B, and C, respectively, will phase-separate and form a three-phase MPS if the phase component A solution and phase component B solution phase-separate, the phase component A solution and phase component C solution phase-separate, the phase component B solution and phase component C solution phase-separate. Similarly, solutions of phase components A, B, C, and D will form a four-phase MPS if the following phase components combinations all phase-separate: A-B-C, A-B-D, A-C-D, and B-C-D. Likewise, solutions of phase components A, B, C, D, and E will form a five-phase MPS if the following phase components combinations all phase-separate: A-B-C-D, A-B-C-E, A-B-D-E, A-C-D-E, B-C-D-E. Also, solutions of phase components A, B, C, D, E, and F will form a six-phase MPS if the following phase components combinations all phase-separate: A-B-C-D-E, A-B-C-D-F, A-B-C-E-F, A-B-D-E-F, A-C-D-E-F, and B-C-D-E-F. The prediction of more complex MPSs based on the same principle is contemplated. These predictions have largely been confirmed by experimental data. Certain predicted MPS have not been produced by experiments can be produced via routine experimental optimization.

As used herein, a MPS can be identified by its phase components in the phases of the MPS. For instance, a Ficoll-dextran-poly(2-ethyl-2-oxazoline) system refers to a three-phase MPS, wherein the phase components in each phases of the MPS are Ficoll, dextran, and poly(2-ethyl-2-oxazoline), but not necessarily in that order. Each phase includes a suitable solvent capable of dissolving the phase components. In some instances, a liquid polymer is used and the liquid polymer forms a phase with no solvent added.

Method

1. Method of Preparing a Multi-Phase System

Multi-phase systems can be prepared by preparing stock solutions of the desired phase components, mixing the desired stock solutions, and allowing the mixture to phase separate. Appropriate volumes of stock solutions are combined. Salts can be added to facilitate polymer-polymer phase separation. Typically, the combined stock solutions are centrifuged to accelerate phase separation. Although separation can occur by gravity settling, the time scales are longer than centrifugation.

Alternatively, MPSs can be prepared by combined the desired phase components in their substantially pure solid or liquid form with a common solvent, followed by mixing or shaking the mixture and allowing the mixture to phase separate. As used herein, a substantially pure phase component refers to a polymer or surfactant with more than 80%, 85%, 90%, 95%, 98%, 99%, or 99.9% purity and free of any solvent. A combination of these two methods can also be used, e.g., one or more phase component stock solutions can be mixed with one or more phase components in their pure solid or liquid forms, and the mixture can then be mixed or shaken and allowed to phase separate. In an exemplary embodiment, stock solutions of 1 mL 20% PVA, 1 mL 20% PEG, and 1 mL 40% dextran can be combined and allowed to phase separate to form a three-phase MPS. Alternatively, 200 mg PVA, 200 mg PEG, 400 mg dextran, and 3 mL water can be combined and allowed to phase separate to form the same three-phase MPS.

In yet another aspect, a multi-phase system can be prepared based on the known behavior of existing multiphase systems. Once a two-phase system is identified, having a first phase with a first polymer (A) and a second phase with a second polymer (B), it is possible to prepare a three phase polymer system by introducing a third phase having a copolymer of the first and second polymers to the two-phase system, e.g., the copolymer is an A-B block, an A-B-A block, etc. In other words, once two polymers are identified that form immiscible phases, then it is expected that copolymers of these two immiscible polymers will phase separate from both starting homopolymers. Non-limiting examples of the first and the second polymers include poly(ethylene glycol)-poly(propylene glycol)- and Pluronic (a PEG-PPG copolymer).

In some embodiments, the copolymer comprises about 10% of the first polymer monomer and about 90% of the second polymer monomer. In some embodiments, the copolymer comprises about 20% of the first polymer monomer and about 80% of the second polymer monomer. In some embodiments, the copolymer comprises about 30% of the first polymer monomer and about 70% of the second polymer monomer. In some embodiments, the copolymer comprises about 40% of the first polymer monomer and about 60% of the second polymer monomer. In some embodiments, the copolymer comprises about 50% of the first polymer monomer and about 50% of the second polymer monomer. In some embodiments, the first, second, and co-polymers phases are aqueous. In some embodiments, the first, second, and co-polymers phases are organic.

2. Method of Analyzing an Analyte of Interest Based on Affinity

In yet another aspect, a novel MPS is used for analyzing or separating an analyte of interest. In some embodiments, the separation of the analyte is based on affinity. The analyte has preferential affinity for one phase over other phases of the MPS. In order for the MPS to be used for affinity analysis, the different phase components interact with the analyte and preferentially partition into the phase with which it has the highest affinity.

In order to preferentially partition into one phase or another, the analyte is subjected to simultaneous contact with all of the phases in the novel multi-phase systems as described herein. The analyte and the MPS mixture is subjected to thorough mixing so that the analyte can interact with the entire system and preferentially partitions into one phase as the mixed system phase separates. In some embodiments, the analyte and the MPS mixture is stacked in a shaker or by hand. Other methods of mixing known in the art are contemplated. Mixing creates a non-equilibrium state. The system may regain equilibrium by centrifuging or waiting for gravity to settle out the phases again.

Partitioning, as described in this manner, is well suited for small analytes. Exemplary small analytes include small molecules, proteins and peptides, antibodies, oligonucleotides, organelles, viruses, and cells. Some analytes are small enough so that they are not suitable for density based separation. In these cases, the analytes can be subjected to partitioning in MPS, or affinity based separation using a MPS.

3. Method of Analyzing or Separating an Analyte of Interest Based on Density

The multi-phase systems are well suited for analysis of analytes based on density. That is, the MPS can distinguish among analytes based on differences in their density. In order to separate analytes in this way, the MPS system should have a density range that is close to that of the analyst of interest. Of course it is possible that some of the analytes can be of higher density or lower density than the density range of the MPS, in which case they would occupy positions above and below the MPS respectively during the separation process.

In some embodiments, the MPS is used to analyze an analyte of interest. Each phase of the MPS has an upper and a lower phase boundary, and the multi-phase system further comprises an analyte located at one of said boundaries. In other words, the analyte may remain at the interface of two adjacent phases. This may be due to the fact that the density of the analyte is between the two adjacent phases contacting the interface. In other embodiments, the analyte may have the same density as that of one of the phases and the analyte will remain in the phase without contacting any boundary and between the upper and lower boundaries of that phase. In still other embodiments, the analyte may have a density less than that of the top phase of the MPS (the phase with the least density) and remain at the top of the MPS with a portion of the analyte above the upper boundary of the top phase. In still other embodiments, the analyte may have a density more than that of the bottom phase of the MPS (the phase with the most density) and remain at the bottom of the MPS. Non-limiting examples of the analytes include solid particles, aggregates of small particles, plastic resins, wood fragments, glasses, and minerals.

In some specific embodiments, the analyte is subjected to sequential contact with one or more of the phases in the multi-phase system. In these embodiments, the analyte is separated based on its density. The analyte is introduced into a phase separated multi-phase system without disturbing the phases and allowed to migrate to a location in the multiphase system that is characteristic of its density. This density-based separation is described in more details below.

In yet another aspect, a method of analyzing or separating a sample comprising one or more analytes of interest using a multi-phase system is described, comprising:

a) providing a multi-phase system comprising two or more phases including at least two adjacent phases, wherein
    each of the two adjacent phases comprises a phase component selected from the group consisting of a polymer, a surfactant, and a combination thereof;
    at least one of the two adjacent phases comprises a polymer;
    each of the two or more phases has a different density and the two or more phases, taken together, represent a density gradient; and
    the two adjacent phases are phase-separated from each other;

b) introducing a sample comprising one or more analytes of interest to the multi-phase system; and c) allowing each of the analytes to migrate to a location in the multiphase system that is characteristic of its density, wherein during migration the sample contacts one or more of the two or more phases sequentially.

In some embodiments, each of the adjacent phases share a common solvent. In some embodiments, each of the adjacent phases share a common organic solvent. The organic solvent can be selected from the groups consisting of liquid polymer, non-polar organic solvent, polar aprotic or protic solvent, supercritical fluid, fuel, oils, and fluorinated solvents, and combinations thereof. In some embodiments, each of the two or more phases comprises a phase component. In some embodiments, each of the two or more phases is organic. In some embodiments, each of the two or more phases is aqueous. In some embodiments, the multi-phase system comprises at least one aqueous phase and at least one organic phase. In some specific embodiments, the MPS comprises a mixture of aqueous and organic phases. In some embodiments, the polymer is selected from the group consisting of homopolymer, block copolymer, copolymer, terpolymer, random copolymer, and a combination thereof. In some embodiments, the polymer has a morphology selected from a group consisting of linear polymer, branched polymer, crosslinked polymer, and dendrimer system.

In some specific embodiments, the multi-phase system further comprises one or more additional phases selected from the group consisting of silicone oil, ionic liquid, fluorinated liquid, organic solvent, liquid metal, and a combination thereof. The additional phases are not required to have a phase component.

In these embodiments, the analyte is introduced into the MPS and allowed to migrate through the one or more phases of the MPS, one phase at a time. Thus, the analyte will contact the phase(s) of the MPS sequentially and migrate to a location of MPS corresponding to its density. In this process, the analyte does not have simultaneous contact with two or more phases of the MPS except when passing the interface between two adjacent phases. This method is distinguished from the separation based on affinity as described above in that in the latter, the analyte needs to have simultaneous contact with all of the phases of the MPS so that a thermodynamic equilibrium is reached and the analyte can preferentially reside in one of the phases based on its affinity towards that phase. This process is commonly referred to as 'partitioning' or 'extraction.' In comparison, in the density-based separation as described herein, the analyte migrates through the MPS phase one at a time, contacting one or more of the phases sequentially and eventually arriving at a location in the MPS characteristic of its density. Because the analyte only experiences a single phase at a time, no partitioning or extraction of the analyte into a particular phase is possible.

Samples comprising the analyte(s) can be introduced to the MPS in the form of a solution or suspension of material. Non-limiting examples of ways in which these samples can be added to the MPS include by pour, pipette, injection, drip, siphon, capillary action, spray, aspiration followed by expulsion, and pump.

In some embodiments, the multi-phases is provided as dispersion or emulsion in another carrier phase. The multi-phase system can be provided in the form of droplets, and they can be dispersed in an oil or fluorinated solvent to be collected/combined prior to use.

Each phase of the MPS has an upper and a lower phase boundary, and two adjacent phases forms a common interface in between. In most instances, there is not an exact match between the analyte density and the density of any particular phase. The analyte's density is between the densities of two adjacent phases in a MPS, and the analyte should therefore remain at the interface of the two adjacent phases. If the analyte should have the same density as that of one of the phases, the analyte will remain with in the density-matched phase without contacting any boundary. In this case, the analyte resides within the phase due to a density match and not due to any favorable or preferential interaction of the analyte with one phase over another. In still other embodiments, the analyte may have a density less than that of the top phase of the MPS (the phase with the least density) and remain at the top of the MPS with a portion of the analyte above the upper boundary of the top phase after migration. In still other embodiments, the analyte may have a density more than that of the bottom phase of the MPS (the phase with the most density) and remain at the bottom of the MPS after migration.

Figure 6:
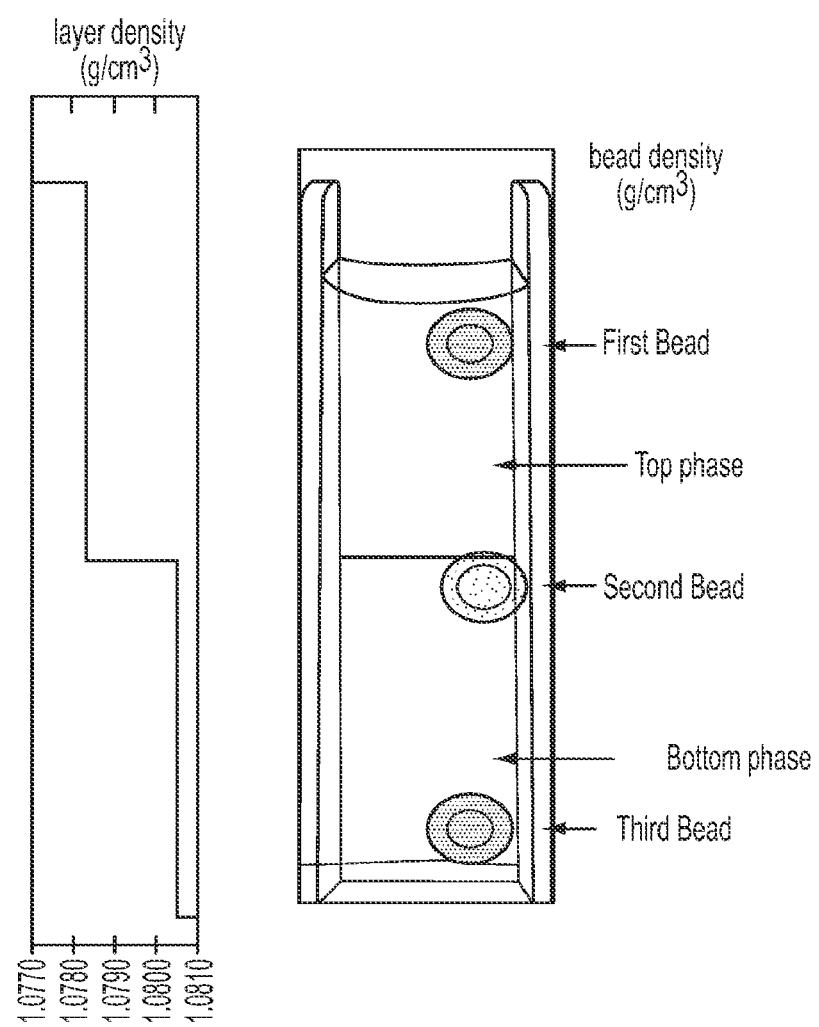
FIG. 6 illustrates a two phase MPS used for separating beads based on density.

A density-based separation of a sample containing one or more analytes using MPS is described with reference to FIG. 6. As shown in FIG. 6, a two-phase MPS (a dextran-Ficoll ATPS) is used for separation of three beads with different densities. A two-phase MPS functions as a two-step sink/float assay and provides three possible equilibrium positions for an object based on the differences in density between the object and its environment: (i) at the interface between air and the top phase, (ii) at the interface between the top and bottom phases, and (iii) at the interface between the bottom phase and the container. As shown in FIG. 6, the first bead, with a density less than the density of the top phase, will reside at the upper boundary of the top phase. The second bead, with a density less than the density of the bottom phase but higher than the top phase, will reside at the interface between the top and the bottom phases. Lastly, the third bead, with a density higher than the densities of the top and bottom phases, will reside at bottom of the MPS and at the interface between the bottom phase and the container. In some embodiments, using the density step produced by the MPS, the objects with density difference of less than 0.100 g/cm$^3$ can be separated. In some embodiments, using the density step produced by the MPS, the objects with density difference of less than 0.050 g/cm$^3$ can be separated. In some embodiments, using the density step produced by the MPS, the objects with density difference of less than 0.010 g/cm$^3$ can be separated. In some embodiments, using the density step produced by the MPS, the objects with density difference of less than 0.005 g/cm$^3$ can be separated. In some embodiments, using the density step produced by the MPS, the objects with density difference of less than 0.004 g/cm$^3$ can be separated. In some embodiments, using the density step produced by the MPS, the objects with density difference of less than 0.002 g/cm$^3$ can be separated. In some embodiments, using the density step produced by the MPS, the objects with density difference of less than 0.001 g/cm$^3$ can be separated.

In some embodiments, the analyte is allowed to migrate based on gravity. In other embodiments, the analyte is allowed to migrate using a centrifuge. Non-limiting examples of centrifuge include laboratory centrifuges (using either a fixed angle or swinging bucket rotors) or a soft-centrifuge. Soft centrifugation refers the uses of soft tubing, e.g., polyethylene tubing, as the sample container and a simple device as the rotor (see, Wong et al., "Egg beater as centrifuge: isolating human blood plasma from whole blood in resource-poor setting", Lab Chip, 2008, 8, 2032-2037). In some specific embodiments, the soft centrifugation is achieved by an eggbeater centrifuge. Other methods of soft centrifugation known in the art are also contemplated.

Migration occurs until the analyte reaches a phase with which it is density matched or a phase of higher density, so that it no longer moves over time through the multi-phase system. This situation is referred to as having reached an 'equilibrium location'. In the case of gravity migration, the time to reach equilibrium migration is in the range of seconds, minutes, hours, days, or more. This depends on the viscosity of the phases, density difference between the phase and the analyte, and the size/shape of the analyte. Use of centrifugation can accelerate the migration process and reduce the time to reach equilibrium location. The centrifuge works using the sedimentation principle, where the centripetal acceleration causes more dense substances to separate out along the radial direction (the bottom of the tube). By the same token, lighter objects will tend to move to the top. The centrifugation can be run at different temperatures such as 4° C., 22° C., 37° C., or 60° C. Additionally, the centrifugation can be run at from low speed (several multiples of g) to 170,000 g or more. The centrifugation can be run from seconds, minutes, hours, or days. The centrifugation can be run using swinging bucket or fixed angle.

Because the separation is carried out using gravity (enhanced gravitational force using centrifugation), the analyte is desirably in suspension in the MPS phases, e.g., the analyte is insoluble in the MPS phases. In addition, separation will be achieved more readily and in a shorter time frame for larger analytes. Without additional modifications, such as aggregating smaller particles into larger aggregates or tagging smaller particles to increase size and/or density, and objects having a dimension of greater than 100 nm, greater than 200 nm, greater than 500 nm, greater than 750 nm or greater than 1 m can be separated. There is no upper limit to the size of the particles that can be separated using the MPS; however, practical considerations such as the size of the density column may limit its application.

In embodiments in which the sample comprises small particles that are of interest, the samples can be subjected to aggregating agents to induce aggregation of the small particles, so that the analyte is larger and can be separated readily using MPS. or the densities of the small particles can be modified using additives to force their migration to different locations in the MPS such that the aggregated small particles pass through one or more phases sequentially. If small particles, such as viruses or cells, have multiple copies of a ligand on their surface, they can be aggregated using reagents functionalized with multiple copies of molecules that recognize that ligand. Non-limiting examples of aggregating agents include multivalent particles (for viruses, cells, anything expressing a surface marker), adenosine diphosphate (for platelets), hemagglutinin (for erythrocytes), concanavalin A (for erythrocytes). For example, a CD4+ T cell and a microparticle functionalized with an antibody to CD4; adenosine diphosphate aggregates platelets; hemagglutinin aggregates erythrocytes; and DNA aggregates gold colloids. The ranges of sizes for the aggregates can be from 10 nm to 100 μm.

Various additives can be added to the phases of MPS. Non-limiting examples of additives include salt, $D_2O$, buffered water, and polymers and surfactant whose amounts are not sufficient to affect a phase separation.

As used herein, the density range of a MPS refers to the range from the lowest density of the phases in MPS, i.e., the density of the top phase, to the highest density of the phases in the MPS, i.e., the density of the bottom phase. The range of the densities of the phases in MPS can be shifted or modified, e.g., broadened. A MPS has a density range set by the top phase (lowest density) and the bottom phase (highest density). Accordingly, if two or more analytes all have densities lower than the density of the top phase in a MPS, the two or more analyte will all reside at the upper boundary of the top phase in a density-based separation and remain unseperated. Likewise, if two or more analytes all have densities higher than the density of the bottom phase in a MPS, the two or more analyte will all reside at the lower boundary of the bottom phase, i.e., the bottom of the MPS, in a density-based separation and remain unseparated.

In some embodiments, the lower end of the density range of an existing MPS can be broadened by adding additional phase(s) with densities lower than the top phase of the existing MPS. The additional phases can phase separate from the phases of the existing MPS and form a new MPS. Thus, the density range of the MPS is effectively broadened by lowering the lower end of the density range. The additional phases can be one or more aqueous phases comprising phase components, or a pure organic or aqueous solvent.

In some embodiments, the upper end of the density range of an existing MPS can be broadened by adding additional phase(s) with densities higher than the bottom phase of the existing MPS. The additional phases can phase separate from the phases of the existing MPS and form a new MPS. Thus, the density range of the MPS is effectively broadened by increasing the upper end of the density range. The additional phases can be one or more aqueous phases comprising phase components, or a pure organic or aqueous solvent.

In some embodiments, each phase of the MPS may have a common solvent. In some embodiments, the density range of a MPS having a common solvent can be shifted by adding one or more additives to the phases of the MPS. In some embodiments, the additive may be soluble in or mixable with the common solvent and thus evenly distributed in each phase of the MPS. Non-limiting examples of the additives include co-solvent, salt, and a combination thereof. The additive may have a density higher or lower than the common solvent. As a result, the density of each phase may all increase or decrease, respectively, upon the addition of the additive.

In some embodiments, the density range of the MPS can be shifted by adding a co-solvent. The co-solvent may be miscible with the common solvent of the MPS and have a density higher or lower than the common solvent of the MPS. In some embodiments, the co-solvent is evenly distributed in all of the MPS phases. In these instances, if a co-solvent with a density higher than the common solvent is added to each phase of the MPS, the density of each phase of the MPS will increase. Alternatively, if a co-solvent with a density lower than the common solvent is added to each phase of the MPS, the density of each phase of the MPS will decrease. In either case, the density range of the original MPS will be shifted. In some specific embodiments, the common solvent of MPS is water and the co-solvent is $D_2O$. $D_2O$ has a density higher than water and thus the density of a water phase will be lower than that of a phase containing water and $D_2O$ as co-solvent (under the same phase component concentrations). In this case, each phase's density will increase.

In some embodiments, the density range of the MPS can be shifted by adding salt. The salt can dissolve in the common solvent of the MPS and is evenly distributed in all of the MPS phases. The salt may have a density higher than the common solvent of the MPS. Non-limiting examples of salts include alkali metal or alkali earth metal halide, phosphate, sulfate, carbonate. Other salts commonly known in the art are contemplated. In some specific examples, the salt is selected from the group consisting of LiBr, NaBr, KBr, RbBr, CsBr, and a combination thereof. The density of the salt is usually higher than the common solvent of the MPS, therefore the density of each phase of the MPS will increase. Alternatively, other small molecules with low densities and soluble in aqueous or organic solvents can be used as additives to decrease the density of a phase.

As a result of the disclosed methods, one or more analytes of interest may preferentially accumulate in one of the phase or at an interface in the MPS, while another analyte, impurity or object in the sample containing the analyte may preferentially accumulate in another phase or interface of the MPS. The desired analyte in the sample can be visualized after separation via a variety of methods. Firstly, separation of some analytes can visualized by human eye. Those that are not readily visible by the eye can be visualized using methods known in the art. For example, separation can be visualized with the aid of a microscope and magnifying glass or by using fluorescent dyes.

In some embodiments, it will be sufficient to simply observe the location of the analyte in the multi-phase system. Suitable analytes for observation by eyes include beads, cells, plastic resins, plastics, glitter, minerals, gems, archaeological species (bone and dirt and clay), etc.

In other embodiments, the desired analyte in the sample can be recovered by retrieving the phase that this analyte preferentially has accumulated in, thus resulting in an improved purity of such analyte. Analytes can be recovered from the system using extraction methods known in the art. In several aspects of one or more embodiments, analytes retained in gradients can be recovered using a fractionator, pipette, drip method, side-puncturing a tube, or combinations thereof. In one aspect, a fractionator can be used to carefully control the pressure on the liquid and pull known volumes of the gradient in certain increments. The drip method can also be used to extract separated analytes. The bottom of a tube is punctured and allowed to drip into sample tubes. This method, like the fractionator method, is ideal for systems such as the disclosed MPS that form clear visual interfaces that can be observed by eye. In another aspect, a pipette is introduced to the top of the sample to remove most, but not all, of the top layer without pulling too close to the interface. Once the top layer is mostly removed, a clean pipette tip can be inserted from the top layer into the second layer. Light agitation of the tip can be used to clear the interface from the tip. The desired layer can then be drawn up in the pipette. The interfaces above and below the desired layer should not be drawn up with the desired layer to avoid layer contamination. In yet another aspect, a plastic tube is side punctured one or more times using a needle, such as a 21 to 16 gauge needle, to puncture the tube at the desired phase. The desired phase is pulled from the tube volume. In each of these aspects, if the analyte of interest is in a phase, the interfaces above and below the phase should not be disturbed to avoid layer contamination. Similarly, if the analyte of interest is in an interface, the phases above and below the interface should not be disturbed to avoid layer contamination.

The sample containing the analyte can be liquid, e.g., liquid droplets (immiscible in that various phases of the MPS), a solid, gel, or liquid crystal. The sample is selected from the group consisting of forensics study sample, a sample indicative of animal health, a sample indicative of human identity used for border control, home land security, or intelligence, a sample from food processing, a sample indicative of product quality, a sample indicative of environmental safety, a sample containing different crystal polymorphs, and combinations thereof. By way of example, rocks and bones can be separated by density. This may assist in forensic investigations or archaeology where it is desired to remove impurities found with valuable evidence. It also may be able to distinguish between different fragments of materials. Because the method is non-destructive, it can be used to separate a materials and the forensic evidence can be further analyzed. Other non-limiting examples include crystallites, mineral, biomineral (bone), composite, plastic, textile, wood, and all applications of those species. For instance, the MPS described herein can be used for checking for viable seeds, or grains, detecting oils of plant origins, or distinguishing different type of food products including cheeses, peanut butter, and honeys.

In some embodiments, a two-phase MPS can be used for purposes disclosed herein. In some other embodiments, three or more phase systems are used. It was believed that the inclusion of additional phases may prevent the enrichment of the target molecule in a specific phase, because the target molecule may distribute into the additional phases. This belief may account for the lack of literature regarding these multi-phase polymer systems. Applicants have surprisingly found that broadening the landscape of polymers that demonstrate immiscibility in aqueous multi-phase polymer systems provides superior tunability for applications based on differences in density and affinity and finer control over the partitioning of complex mixtures of subjects.

In some embodiments, the multi-phase polymer system is provided by mixing suitable polymers or surfactants with a solvent and subjecting the mixture to centrifugation. For instance, a mixture of solid polymers or surfactants can be mixed with a common solvent, e.g., water, to allow the resulting mixture to phase-separate to form a MPS. Any types of centrifugation known in the art can be used in the formation of the MPS. In some embodiments, the MPS is formed using soft centrifugation. Soft centrifugation is described above. In some specific embodiments, the soft centrifugation is achieved by an eggbeater centrifuge. Other methods of soft centrifugation known in the art are also contemplated.

The method Applicants report here combines the portability and simplicity of the soft centrifuge with aqueous multiphase density barriers generated from immiscible polymers or surfactants. Immiscible polymers or surfactants have numerous advantages over discontinuous density gradients for field use: they are easily prepared, owing to the nature of their mutual immiscibility; they are stable, and thus amenable to long term storage; and they are versatile, as Applicants have previously identified a suite of multiphase systems that can be altered (composition and/or density) to suit the application.

3. Method of Determining an Object's Density Using a MPS

All matter is characterized by physical properties (e.g., mass, conductivity, and permittivity). As measurable quantities, the use of physical properties to compare objects has the potential to be widely applicable to a range of problems. Differences in density, for example, have been used to analyze the composition or purity of samples and monitor chemical processes. One approach to density analysis is the sink/float assay—an object is introduced to a solution and is either more dense (i.e., it sinks) or less dense (i.e., it floats) than the solution. This assay, and its binary method of separation, has applications in recovering archaeological samples from soil, liberating metals from plastics in scrap recycling, and isolating biological materials. Using this approach, applications requiring the density-based separation of multiple components involve a series of solutions with a range of densities. In some embodiments, a MPS produced from a mixture of immiscible liquids is used to determine the density of an object. Mixtures of liquids that result in phase separation include oil/water, dichloromethane/water, aqueous two-phase polymer systems (ATPS), and MPS as described herein.

In yet another aspect, a method of determining the density of a solid particle using a multi-phase system is described, comprising:

a) providing a multi-phase system comprising two or more phases, wherein
   at least one of the phases comprises a phase component, wherein the phase component is selected from the group consisting of a polymer, a surfactant, and a combination thereof;
   each of the two or more phases has a different density and the two or more phases, taken together, represent a density gradient; and
   the phases are phase-separated from each other;
b) introducing a solid particle to the multi-phase system;
c) allowing the solid particle to migrate to a location in the multiphase system that is characteristic of its density, wherein during migration the sample contacts one or more of the two or more phases sequentially; and
d) determining the density of the solid particle.

In some embodiments, the solid particle is within one of the phases after migration and the density of the solid particle is measured as the density of the phase the containing the solid particle.

In some embodiments, the solid particle is a bead residing in an interface between two adjacent phases and the density of the bead is calculated based on the position of the bead, the buoyancy, and the interfacial tension between the two phases. In these embodiments, the bead is captured at the liquid/liquid interface of a MPS, and a displacement of interface can be observed (see FIG. 7) proportional to differential buoyant density of the bead across the density step. By balancing the gravitational, buoyant, and interfacial forces that act on the bead at the liquid/liquid interface, an equation is derived capable of calculating the density of the bead to within an accuracy of 1% using measured geometric parameters (e.g., bead radius and contact angle). This equation is used to calculate the unknown density of a polystyrene bead, e.g., a polystyrene bead.

Current approaches to density-based separations employ gradients: (i) kinetic density gradients must be produced in situ by centrifugation during a separation, centrifugation parameters (e.g., time and relative centrifugal force) require optimization, and do not provide interfaces for sample collection; and (ii) sequential step gradients (e.g., using increasing concentrations of sucrose or Ficoll) require skill to prepare, must be prepared immediately prior to use, and the interfaces between layers are under thermodynamic control (e.g., diffusion and mixing will destroy the interface). In contrast, density steps prepared by phase separation offer many ideal features: (i) steps form spontaneously after mixing, (ii) the systems are at equilibrium and may be prepared in advance, (iii) the magnitude of the density step can be adjusted by changing the concentrations of the components that comprise each phase, and (iv) the interface between phases is well-defined and thus useful for isolating objects after separation.

In some embodiments, beads of known density are introduced to an ATPS manually and allowed to settle under gravity (i.e., Ig). The differences in density between the bead and each layer of the ATPS (i.e., the buoyant density) controls the rates by which the bead migrates through the system. For example, the beads required approximately ten minutes to migrate completely through the small density step produced by the ATPS (for a dextran-Ficoll ATPS, the zp between the two phases is 0.0023 g/cm$^3$). In some embodiments, centrifugal force is applied to speed up the migration. The applied centrifuge increases the sedimentation rate of each bead, but does not affect the final position of the bead.

Figure 8:
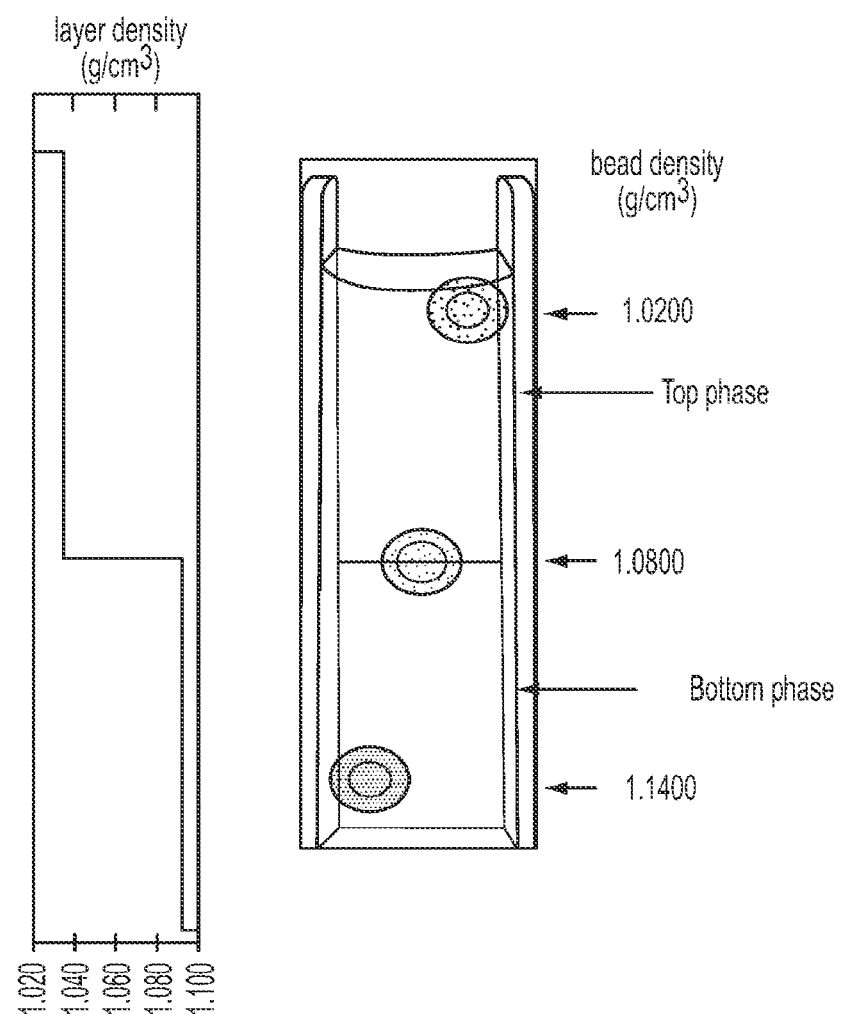
FIG. 8 illustrates a density-based separation using a two-phase MPS.

Referring back to FIG. 6, three beads are separated by using the density step produced by the ATPS, e.g., a dextran-Ficoll ATPS, with one bead at each possible interface (FIG. 6). In some embodiments, the differences in density between the beads in this set can be very small, e.g., less than about 0.0020 g/cm$^3$, but the density step between phases in the ATPS resolves each bead readily. Separations of beads with larger differences in density using a larger density step are also possible (e.g., PEG-Ficoll ATPS; FIG. 8).

Figure 7A:
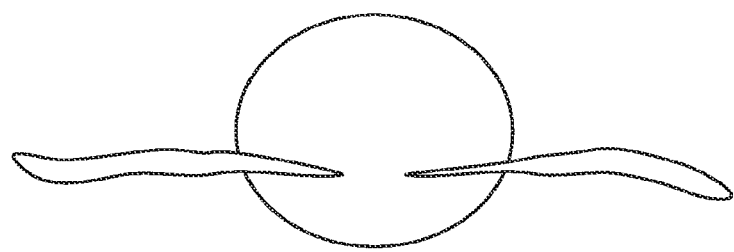
FIG. 7A-7B illustrates forces on a sphere at an interface. (A) An image of a polystyrene bead ($\rho=1.0456$ g/cm$^3$) at the interface between a poly(ethylene glycol)-Ficoll aqueous two-phase polymer system (layer densities of 1.0320 g/cm$^3$ and 1.1122 g/cm$^3$, respectively). (B) An overlayed schematic of the three forces acting on the bead at the liquid/liquid interface: gravitational force ($F_g$), buoyant force ($F_B$), and interfacial tension ($F_I$).

The position of the bead in the interface can be used to measure density. While the layer/layer interface captured beads predictably based on density, the presence of the bead displaced partially the otherwise continuous interface of the ATPS (FIG. 7A). As a result, the absolute position of the bead varied in a manner that depended on (i) the density of the bead, (ii) the density of each layer, and (iii) the contact angle at the bead/liquid/liquid interface. There are three forces acting on a bead residing at the interface of an ATPS: (i) gravity ($F_g$; N), (ii) buoyancy ($F_B$; N), (iii) and the interfacial tension ($F_I$; N). At equilibrium, these forces are balanced (equation 1).

$$\vec{F}_g = \vec{F}_B + \vec{F}_I \qquad (1)$$

In some embodiments, the density of the solid object or particle can be calculated based on equation 1. In some specific embodiments, the solid object is a bead and the density of the bead ($\rho_0$; g/cm$^3$) can be calculated as a function of the density of the top phase ($\rho_t$; g/cm$^3$), the density of the bottom phase ($\rho_b$; g/cm$^3$), the acceleration due to gravity (g; m/s$^2$), the interfacial tension between the top and bottom layers ($\gamma_{bt}$; N/m), the surface/liquid/liquid contact angle ($\theta_c$; deg), the angle between the bead center and the bead/interface point of intersection ($\varphi$; deg), the bead radius (R; m), and the displacement of the interface (d; m) (equation 2; for a full derivation, please see experimental section). Equation 2 comprises terms for the mean solution density, a correction for buoyancy, and a correction for surface tension.

$$\rho_0 = \frac{(\rho_b + \rho_t)}{2} + \frac{(\rho_b - \rho_t)}{4}\left[\cos^3\phi - 3\cos\phi + 3\frac{d}{R}\sin^2\phi\right] + \frac{3\gamma_{bt}}{2gR^2}\sin\phi\cos(\theta_c + \phi - \pi) \qquad (2)$$

Figure 7B:
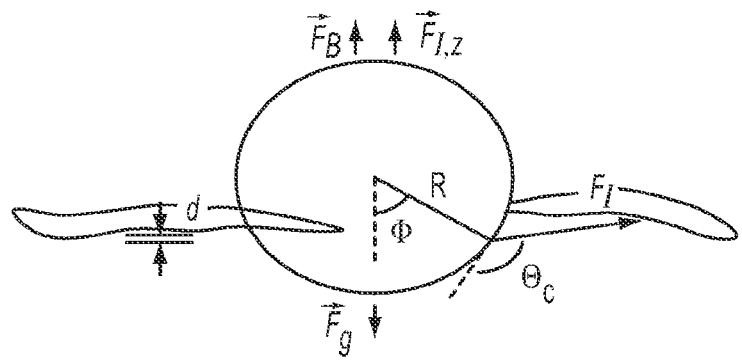

In some embodiments, the density of a bead of unknown density is calculated geometrically using equation (2) from several measured variables (FIG. 7B).

Preparation of Specific Multiphase Systems

In one aspect, a multi-phase system comprising two or more phases is described, wherein
   each phase comprises a phase component selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(vinyl alcohol), poly(2-ethyl-2-oxazoline), poly(ethylene glycol), dextran, Ficoll, and Tween;

with the proviso that the multi-phase system does not include:

an aqueous three-phase system wherein the phase components in the three phases are a combination of poly(ethylene glycol)-dextran-Ficoll; or an aqueous two-phase system wherein the phase components in the two phases are a combination selected from the group consisting of poly(vinyl alcohol)-poly(ethylene glycol), poly(vinyl alcohol)-dextran, dextran-Ficoll, poly(ethylene glycol)-Ficoll, poly(ethylene glycol)-dextran, poly(ethylene glycol)-Tween, and dextran-Tween. The solvent for each phase can be aqueous or organic. In some embodiments, the MPS comprises a mixture of aqueous and organic phases.

In some embodiments, the multi-phase system is a six-phase system and the phase components in the six phases are poly(vinyl alcohol), poly(2-ethyl-2-oxazoline), poly(ethylene glycol), dextran, Ficoll, and Tween, respectively. In some specific embodiments, each phase of the MPS is aqueous phase.

In some embodiments, the multi-phase system is a five-phase system and the phase components in the five phases are a combination of phase components selected from the group consisting of poly(vinyl alcohol)-poly(2-ethyl-2-oxazoline)-poly(ethylene glycol)-dextran-Ficoll,
poly(vinyl alcohol)-poly(2-ethyl-2-oxazoline)-poly(ethylene glycol)-dextran-Tween,
poly(vinyl alcohol)-poly(2-ethyl-2-oxazoline)-poly(ethylene glycol)-Ficoll-Tween,
poly(vinyl alcohol)-poly(ethylene glycol)-dextran-Ficoll-Tween,
poly(vinyl alcohol)-poly(2-ethyl-2-oxazoline)-dextran-Ficoll-Tween, and
poly(2-ethyl-2-oxazoline)-poly(ethylene glycol)-dextran-Ficoll-Tween. In some specific embodiments, each phase of the MPS is aqueous phase.

In some embodiments, the multi-phase system is a four-phase system and the phase components in the four phases are a combination of phase components selected from the group consisting of poly(vinyl alcohol)-poly(2-ethyl-2-oxazoline)-poly(ethylene glycol)-dextran,
poly(vinyl alcohol)-poly(2-ethyl-2-oxazoline)-poly(ethylene glycol)-Ficoll,
poly(vinyl alcohol)-poly(2-ethyl-2-oxazoline)-poly(ethylene glycol)-Tween,
poly(vinyl alcohol)-poly(2-ethyl-2-oxazoline)-dextran-Ficoll,
poly(vinyl alcohol)-poly(2-ethyl-2-oxazoline)-dextran-Tween,
poly(vinyl alcohol)-poly(2-ethyl-2-oxazoline)-Ficoll-Tween,
poly(vinyl alcohol)-poly(ethylene glycol)-dextran-Ficoll,
poly(vinyl alcohol)-poly(ethylene glycol)-dextran-Tween,
poly(vinyl alcohol)-poly(ethylene glycol)-Ficoll-Tween,
poly(vinyl alcohol)-dextran-Ficoll-Tween,
poly(2-ethyl-2-oxazoline)-poly(ethylene glycol)-dextran-Ficoll,
poly(2-ethyl-2-oxazoline)-poly(ethylene glycol)-dextran-Tween,
poly(2-ethyl-2-oxazoline)-poly(ethylene glycol)-Ficoll-Tween,
poly(2-ethyl-2-oxazoline)-dextran-Ficoll-Tween, and
poly(ethylene glycol)-dextran-Ficoll-Tween. In some specific embodiments, each phase of the four-phase MPS is aqueous phase.

In some embodiments, the multi-phase system is a three-phase system and the phase components in the three phases are a combination of phase components selected from the group consisting of poly(vinyl alcohol)-poly(2-ethyl-2-oxazoline)-poly(ethylene glycol),
poly(vinyl alcohol)-poly(2-ethyl-2-oxazoline)-dextran,
poly(vinyl alcohol)-poly(2-ethyl-2-oxazoline)-Ficoll,
poly(vinyl alcohol)-poly(2-ethyl-2-oxazoline)-Tween,
poly(vinyl alcohol)-poly(ethylene glycol)-dextran,
poly(vinyl alcohol)-poly(ethylene glycol)-Ficoll,
poly(vinyl alcohol)-poly(ethylene glycol)-Tween,
poly(vinyl alcohol)-dextran-Ficoll,
poly(vinyl alcohol)-dextran-Tween,
poly(vinyl alcohol)-Ficoll-Tween,
poly(2-ethyl-2-oxazoline)-poly(ethylene glycol)-dextran,
poly(2-ethyl-2-oxazoline)-poly(ethylene glycol)-Ficoll,
poly(2-ethyl-2-oxazoline)-poly(ethylene glycol)-Tween,
poly(2-ethyl-2-oxazoline)-dextran-Ficoll,
poly(2-ethyl-2-oxazoline)-dextran-Tween,
poly(2-ethyl-2-oxazoline)-Ficoll-Tween,
poly(ethylene glycol)-dextran-Tween,
poly(ethylene glycol)-Ficoll-Tween, and
dextran-Ficoll-Tween. In some specific embodiments, each phase of the three-phase MPS is aqueous phase.

In some embodiments, the multi-phase system is a two-phase system and the phase components in the two phases are a combination of phase components selected from the group consisting of poly(vinyl alcohol)-poly(2-ethyl-2-oxazoline),
poly(ethylene glycol)-poly(2-ethyl-2-oxazoline),
poly(ethylene glycol)-dextran,
poly(vinyl alcohol)-Ficoll,
poly(2-ethyl-2-oxazoline)-Ficoll,
poly(vinyl alcohol)-Tween,
poly(2-ethyl-2-oxazoline)-Tween, and
Tween 20-Ficoll. In some specific embodiments, each phase of the two-phase MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(methacrylic acid), poly(2-ethyl-2-oxazoline), poly(ethylene glycol), polyacrylamide, polyethyleneimine, and CHAPS. The solvent for each phase can be aqueous or organic. In some embodiments, the MPS comprises a mixture of aqueous and organic phases. In some embodiments, the MPS comprises all aqueous phases. In some embodiments, the MPS comprises all organic phases.

In some embodiments, the multi-phase system is a six-phase system and the phase components in the six phases are poly(methacrylic acid), poly(2-ethyl-2-oxazoline), poly(ethylene glycol), polyacrylamide, polyethyleneimine, and CHAPS, respectively. In some specific embodiments, each phase of the MPS is aqueous phase.

In some embodiments, the multi-phase system is a five-phase system and the phase components in the five phases are a combination of phase components selected from the group consisting of
poly(methacrylic acid)-poly(2-ethyl-2-oxazoline)-poly(ethylene glycol)-polyacrylamide-polyethyleneimine,
poly(methacrylic acid)-poly(2-ethyl-2-oxazoline)-poly(ethylene glycol)-polyacrylamide-CHAPS,
poly(methacrylic acid)-poly(2-ethyl-2-oxazoline)-poly(ethylene glycol)-polyethyleneimine-CHAPS,
poly(methacrylic acid)-poly(2-ethyl-2-oxazoline)-polyethyleneimine-polyacrylamide-CHAPS,
poly(methacrylic acid)-poly(ethylene glycol)-polyethyleneimine-polyacrylamide-CHAPS, and
poly(2-ethyl-2-oxazoline)-poly(ethylene glycol)-polyethyleneimine-polyacrylamide-CHAPS. In some specific embodiments, each phase of the MPS is aqueous phase.

In some embodiments, the multi-phase system is a four-phase system and the phase components in the four phases are a combination of phase components selected from the group consisting of
poly(methacrylic acid)-poly(2-ethyl-2-oxazoline)-poly(ethylene glycol)-polyethyleneimine,
poly(methacrylic acid)-poly(2-ethyl-2-oxazoline)-poly(ethylene glycol)-polyacrylamide,
poly(methacrylic acid)-poly(2-ethyl-2-oxazoline)-poly(ethylene glycol)-CHAPS,
poly(methacrylic acid)-poly(2-ethyl-2-oxazoline)-polyacrylamide-polyethyleneimine,
poly(methacrylic acid)-poly(2-ethyl-2-oxazoline)-polyacrylamide-CHAPS,
poly(methacrylic acid)-poly(2-ethyl-2-oxazoline)-polyethyleneimine-CHAPS,
poly(methacrylic acid)-polyethyleneimine-poly(ethylene glycol)-polyacrylamide,
poly(methacrylic acid)-poly(ethylene glycol)-polyacrylamide-CHAPS,
poly(methacrylic acid)-poly(ethylene glycol)-polyethyleneimine-CHAPS,
poly(methacrylic acid)-polyacrylamide-polyethyleneimine-CHAP S,
poly(2-ethyl-2-oxazoline)-poly(ethylene glycol)-polyacrylamide-polyethyleneimine,
poly(2-ethyl-2-oxazoline)-poly(ethylene glycol)-polyacrylamide-CHAPS,
poly(2-ethyl-2-oxazoline)-poly(ethylene glycol)-polyethyleneimine-CHAPS,
poly(2-ethyl-2-oxazoline)-polyacrylamide-polyethyleneimine-CHAPS, and
poly(ethylene glycol)-polyacrylamide-polyethyleneimine-CHAPS. In some specific embodiments, each phase of the MPS is aqueous phase.

In some embodiments, the multi-phase system is a three-phase system and the phase components in the three phases are a combination of phase components selected from the group consisting of
poly(methacrylic acid)-poly(2-ethyl-2-oxazoline)-poly(ethylene glycol),
poly(methacrylic acid)-poly(2-ethyl-2-oxazoline)-polyacrylamide,
poly(methacrylic acid)-poly(2-ethyl-2-oxazoline)-polyethyleneimine,
poly(methacrylic acid)-poly(2-ethyl-2-oxazoline)-CHAPS,
poly(methacrylic acid)-poly(ethylene glycol)-polyacrylamide,
poly(methacrylic acid)-poly(ethylene glycol)-polyethyleneimine,
poly(methacrylic acid)-poly(ethylene glycol)-CHAPS,
poly(methacrylic acid)-polyacrylamide-polyethyleneimine,
poly(methacrylic acid)-polyacrylamide-CHAPS,
poly(methacrylic acid)-polyethyleneimine-CHAPS,
poly(2-ethyl-2-oxazoline)-poly(ethylene glycol)-polyethyleneimine,
poly(2-ethyl-2-oxazoline)-poly(ethylene glycol)-polyacrylamide,
poly(2-ethyl-2-oxazoline)-poly(ethylene glycol)-CHAPS,
poly(2-ethyl-2-oxazoline)-poly acrylamide-poly ethyleneimine,
poly(2-ethyl-2-oxazoline)-polyacrylamide-CHAPS,
poly(2-ethyl-2-oxazoline)-poly ethyleneimine-CHAPS,
poly(ethylene glycol)-polyacrylamide-polyethyleneimine,
poly(ethylene glycol)-polyacrylamide-CHAPS,
poly(ethylene glycol)-polyethyleneimine-CHAPS, and
polyacrylamide-polyethyleneimine-CHAPS. In some specific embodiments, each phase of the MPS is aqueous phase.

In some embodiments, the multi-phase system is a two-phase system and the phase components in the two phases are a combination of phase components selected from the group consisting of
poly(methacrylic acid)-poly(2-ethyl-2-oxazoline),
poly(methacrylic acid)-poly(ethylene glycol),
poly(methacrylic acid)-polyacrylamide,
poly(methacrylic acid)-polyethyleneimine,
poly(methacrylic acid)-CHAPS,
poly(2-ethyl-2-oxazoline)-polyethyleneimine,
poly(2-ethyl-2-oxazoline)-polyacrylamide,
poly(2-ethyl-2-oxazoline)-poly(ethylene glycol),
poly(2-ethyl-2-oxazoline)-CHAPS,
poly(ethylene glycol)-polyethyleneimine,
poly ethyleneimine-poly acrylamide,
polyethyleneimine-CHAPS,
polyacrylamide-poly(ethylene glycol),
poly(ethylene glycol)-CHAPS, and
polyacrylamide-CHAPS. In some specific embodiments, each phase of the two-phase MPS is aqueous phase.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of poly(methacrylic acid), poly(2-ethyl-2-oxazoline), polyacrylamide, polyethyleneimine, Pluronic and CHAPS. Pluronic F68 is the species of PEG-PPG co-polymer that is a member of a large family of PEG-PPG block copolymers. It is contemplates that others in the family will have similar properties.

In some embodiments, the multi-phase system is a six-phase system and the phase components in the six phases are poly(methacrylic acid), poly(2-ethyl-2-oxazoline), polyacrylamide, polyethyleneimine, Pluronic, and CHAPS, respectively. In some embodiments, the MPS comprises a mixture of aqueous and organic phases.

In some embodiments, the multi-phase system is a five-phase system and the phase components in the five phases are a combination of phase components selected from the group consisting of
poly(methacrylic acid)-poly(2-ethyl-2-oxazoline)-polyacrylamide-polyethyleneimine-Pluronic,
poly(methacrylic acid)-poly(2-ethyl-2-oxazoline)-polyacrylamide-Pluronic-CHAPS,
poly(methacrylic acid)-poly(2-ethyl-2-oxazoline)-polyethyleneimine-Pluronic-CHAPS,
poly(methacrylic acid)-polyacrylamide-polyethyleneimine-Pluronic-CHAPS, and
poly(2-ethyl-2-oxazoline)-polyacrylamide-polyethyleneimine-Pluronic-CHAPS. In some specific embodiments, each phase of the MPS is aqueous phase.

In some embodiments, the multi-phase system is a four-phase system and the phase components in the four phases are a combination of phase components selected from the group consisting of
poly(methacrylic acid)-poly(2-ethyl-2-oxazoline)-polyacrylamide-Pluronic,
poly(methacrylic acid)-poly(2-ethyl-2-oxazoline)-polyacrylamide-CHAPS,
poly(methacrylic acid)-poly(2-ethyl-2-oxazoline)-polyethyleneimine-Pluronic,
poly(methacrylic acid)-poly(2-ethyl-2-oxazoline)-polyethyleneimine-CHAPS,
poly(methacrylic acid)-poly(2-ethyl-2-oxazoline)-Pluronic-CHAPS,
poly(methacrylic acid)-poly(2-ethyl-2-oxazoline)-polyacrylamide-polyethyleneimine,
poly(methacrylic acid)-polyacrylamide-polyethyleneimine-Pluronic,
poly(methacrylic acid)-polyacrylamide-polyethyleneimine-CHAPS,
poly(methacrylic acid)-polyacrylamide-Pluronic-CHAPS,
poly(methacrylic acid)-polyethyleneimine-Pluronic-CHAPS,
polyacrylamide-poly(2-ethyl-2-oxazoline)-polyethyleneimine-Pluronic F68,
polyacrylamide-poly(2-ethyl-2-oxazoline)-polyethyleneimine-CHAPS,
polyacrylamide-poly(2-ethyl-2-oxazoline)-Pluronic-CHAPS,
polyethyleneimine-poly(2-ethyl-2-oxazoline)-Pluronic-CHAPS, and
polyacrylamide-polyethyleneimine-Pluronic-CHAPS. In some specific embodiments, each phase of the MPS is aqueous phase.

In some embodiments, the multi-phase system is a three-phase system and the phase components in the three phases are a combination of phase components selected from the group consisting of
poly(methacrylic acid)-poly(2-ethyl-2-oxazoline)-polyacrylamide,
poly(methacrylic acid)-poly(2-ethyl-2-oxazoline)-polyethyleneimine,
poly(methacrylic acid)-poly(2-ethyl-2-oxazoline)-Pluronic,
poly(methacrylic acid)-poly(2-ethyl-2-oxazoline)-CHAPS,
poly(methacrylic acid)-polyacrylamide-polyethyleneimine,
poly(methacrylic acid)-polyacrylamide-Pluronic,
poly(methacrylic acid)-polyacrylamide-CHAPS,
poly(methacrylic acid)-polyethyleneimine-Pluronic,
poly(methacrylic acid)-polyethyleneimine-CHAPS,
poly(methacrylic acid)-Pluronic-CHAPS,
poly(2-ethyl-2-oxazoline)-polyacrylamide-poly ethyleneimine,
poly(2-ethyl-2-oxazoline)-polyacrylamide-Pluronic,
poly(2-ethyl-2-oxazoline)-polyacrylamide-CHAPS,
poly(2-ethyl-2-oxazoline)-poly ethyleneimine-Pluronic,
poly(2-ethyl-2-oxazoline)-poly ethyleneimine-CHAPS,
poly(2-ethyl-2-oxazoline)-Pluronic-CHAPS,
poly acrylamide-poly ethyleneimine-CHAPS,
poly acrylamide-poly ethyleneimine-Pluronic,
polyacrylamide-Pluronic-CHAPS, and
polyethyleneimine-Pluronic-CHAPS. In some specific embodiments, each phase of the MPS is aqueous phase.

In some embodiments, the multi-phase system is a two-phase system and the phase components in the two phases are a combination of phase components selected from the group consisting of
poly(methacrylic acid)-poly(2-ethyl-2-oxazoline),
poly(methacrylic acid)-Pluronic,
poly(methacrylic acid)-polyacrylamide,
poly(methacrylic acid)-polyethyleneimine,
poly(methacrylic acid)-CHAPS,
poly(2-ethyl-2-oxazoline)-polyethyleneimine,
poly(2-ethyl-2-oxazoline)-polyacrylamide,
poly(2-ethyl-2-oxazoline)-Pluronic,
poly(2-ethyl-2-oxazoline)-CHAPS,
poly(ethylene glycol)-polyethyleneimine,
poly ethyleneimine-poly acrylamide,
polyethyleneimine-CHAPS,
poly acrylamide-Pluronic,
Pluronic-CHAPS, and
polyacrylamide-CHAPS. In some specific embodiments, each phase of the two-phase MPS is aqueous phase.

In yet another aspect, a multi-phase system comprising two or more phases is described, wherein
 each phase comprises a phase component, wherein the phase component is selected from the group consisting of a polymer, a surfactant, and a combination thereof;
 each of the two or more phases has a different density and the phases, taken together, represent a density gradient; and
 the phases are phase-separated from each other, wherein the phase components are selected from the groups consisting of poly(methacrylic acid), poly(2-ethyl-2-oxazoline), poly(ethylene glycol), polyethyleneimine, Ficoll, and CHAPS, with the proviso that the multi-phase system does not include:
 an aqueous two-phase system wherein the phase components in the two phases are a combination of poly(ethylene glycol)-Ficoll. In some embodiments, the MPS comprises a mixture of aqueous and organic phases.

In some embodiments, the multi-phase system is a six-phase system and the phase components in the six phases are poly(methacrylic acid), poly(2-ethyl-2-oxazoline), poly(ethylene glycol), Ficoll, polyethyleneimine, and CHAPS, respectively. In some specific embodiments, each phase of the MPS is aqueous phase.

In some embodiments, the multi-phase system is a five-phase system and the phase components in the five phases are a combination of phase components selected from the group consisting of
poly(methacrylic acid)-poly(2-ethyl-2-oxazoline)-poly(ethylene glycol)-Ficoll-polyethyleneimine,
poly(methacrylic acid)-poly(2-ethyl-2-oxazoline)-poly(ethylene glycol)-Ficoll-CHAPS, poly(methacrylic acid)-poly(2-ethyl-2-oxazoline)-poly(ethylene glycol)-polyethyleneimine-CHAPS,
poly(methacrylic acid)-poly(2-ethyl-2-oxazoline)-polyethyleneimine-Ficoll-CHAPS, poly(methacrylic acid)-poly(ethylene glycol)-polyethyleneimine-Ficoll-CHAPS, and poly(2-ethyl-2-oxazoline)-poly(ethylene glycol)-polyethyleneimine-Ficoll-CHAPS. In some specific embodiments, each phase of the MPS is aqueous phase.

In some embodiments, the multi-phase system is a four-phase system and the phase components in the four phases are a combination of phase components selected from the group consisting of poly ethyleneimine-poly(2-ethyl-2-oxazoline)-poly(ethylene glycol)-poly(methacrylic acid), poly(methacrylic acid)-poly(2-ethyl-2-oxazoline)-poly(ethylene glycol)-Ficoll, poly(methacrylic acid)-poly(2-ethyl-2-oxazoline)-poly(ethylene glycol)-CHAPS, poly(methacrylic acid)-poly(2-ethyl-2-oxazoline)-Ficoll-polyethyleneimine, poly(methacrylic acid)-poly(2-ethyl-2-oxazoline)-Ficoll-CHAPS, poly(methacrylic acid)-poly(2-ethyl-2-oxazoline)-polyethyleneimine-CHAPS, poly(methacrylic acid)-polyethyleneimine-poly(ethylene glycol)-Ficoll, poly(methacrylic acid)-poly(ethylene glycol)-Ficoll-CHAPS, poly(methacrylic acid)-poly(ethylene glycol)-polyethyleneimine-CHAPS, poly(methacrylic acid)-Ficoll-polyethyleneimine-CHAPS, poly(2-ethyl-2-oxazoline)-poly(ethylene glycol)-Ficoll-polyethyleneimine, poly(2-ethyl-2-oxazoline)-poly(ethylene glycol)-Ficoll-CHAPS, poly(2-ethyl-2-oxazoline)-poly(ethylene glycol)-polyethyleneimine-CHAPS, poly(2-ethyl-2-oxazoline)-Ficoll-polyethyleneimine-CHAPS, and poly(ethylene glycol)-Ficoll-polyethyleneimine-CHAPS. In some specific embodiments, each phase of the MPS is aqueous phase.

In some embodiments, the multi-phase system is a three-phase system and the phase components in the three phases are a combination of phase components selected from the group consisting of poly(methacrylic acid)-poly(2-ethyl-2-oxazoline)-poly(ethylene glycol), poly(methacrylic acid)-poly(2-ethyl-2-oxazoline)-Ficoll, poly(methacrylic acid)-poly(2-ethyl-2-oxazoline)-polyethyleneimine, poly(methacrylic acid)-poly(2-ethyl-2-oxazoline)-CHAPS, poly(methacrylic acid)-poly(ethylene glycol)-Ficoll, poly(methacrylic acid)-poly(ethylene glycol)-polyethyleneimine, poly(methacrylic acid)-poly(ethylene glycol)-CHAPS, poly(methacrylic acid)-Ficoll-polyethyleneimine, poly(methacrylic acid)-Ficoll-CHAPS, poly(methacrylic acid)-polyethyleneimine-CHAPS, polyethyleneimine-poly(2-ethyl-2-oxazoline)-poly(ethylene glycol), poly(2-ethyl-2-oxazoline)-poly(ethylene glycol)-Ficoll, poly(2-ethyl-2-oxazoline)-poly(ethylene glycol)-CHAPS, poly(2-ethyl-2-oxazoline)-Ficoll-polyethyleneimine, poly(2-ethyl-2-oxazoline)-Ficoll-CHAPS, poly(2-ethyl-2-oxazoline)-poly ethyleneimine-CHAPS, poly(ethylene glycol)-Ficoll-polyethyleneimine, poly(ethylene glycol)-Ficoll-CHAPS, poly(ethylene glycol)-polyethyleneimine-CHAPS, and Ficoll-polyethyleneimine-CHAPS. In some specific embodiments, each phase of the MPS is aqueous phase.

In some embodiments, the multi-phase system is a two-phase system and the phase components in the two phases are a combination of phase components selected from the group consisting of poly(methacrylic acid)-poly(2-ethyl-2-oxazoline), poly(methacrylic acid)-poly(ethylene glycol), poly(methacrylic acid)-Ficoll, poly(methacrylic acid)-polyethyleneimine, poly(methacrylic acid)-CHAPS, poly(2-ethyl-2-oxazoline)-polyethyleneimine, poly(2-ethyl-2-oxazoline)-Ficoll, poly(2-ethyl-2-oxazoline)-poly(ethylene glycol), poly(2-ethyl-2-oxazoline)-CHAPS, poly(ethylene glycol)-polyethyleneimine, polyethyleneimine-Ficoll, polyethyleneimine-CHAPS, poly(ethylene glycol)-CHAPS, and Ficoll-CHAPS. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(methacrylic acid), poly(2-ethyl-2-oxazoline), polyethyleneimine, Pluronic F68, Ficoll, and CHAPS. In some embodiments, the MPS comprises a mixture of aqueous and organic phases.

In some embodiments, the multi-phase system is a six-phase system and the phase components in the six phases are poly(methacrylic acid), poly(2-ethyl-2-oxazoline), Pluronic F68, Ficoll, polyethyleneimine, and CHAPS, respectively. In some specific embodiments, each phase of the MPS is aqueous phase.

In some embodiments, the multi-phase system is a five-phase system and the phase components in the five phases are a combination of phase components selected from the group consisting of poly(methacrylic acid)-poly(2-ethyl-2-oxazoline)-Pluronic-Ficoll-polyethyleneimine, poly(methacrylic acid)-poly(2-ethyl-2-oxazoline)-Pluronic-Ficoll-CHAPS, poly(methacrylic acid)-poly(2-ethyl-2-oxazoline)-Pluronic-polyethyleneimine-CHAPS, poly(methacrylic acid)-poly(2-ethyl-2-oxazoline)-polyethyleneimine-Ficoll-CHAPS, poly(methacrylic acid)-Pluronic-polyethyleneimine-Ficoll-CHAPS, and poly(2-ethyl-2-oxazoline)-Pluronic-polyethyleneimine-Ficoll-CHAPS. In some specific embodiments, each phase of the MPS is aqueous phase.

In some embodiments, the multi-phase system is a four-phase system and the phase components in the four phases are a combination of phase components selected from the group consisting of poly(methacrylic acid)-poly(2-ethyl-2-oxazoline)-Pluronic-Ficoll, poly(methacrylic acid)-poly(2-ethyl-2-oxazoline)-Pluronic-CHAPS, poly(methacrylic acid)-poly(2-ethyl-2-oxazoline)-Ficoll-polyethyleneimine,
poly(methacrylic acid)-poly(2-ethyl-2-oxazoline)-Pluronic-polyethyleneimine,
poly(methacrylic acid)-poly(2-ethyl-2-oxazoline)-Ficoll-CHAPS,
poly(methacrylic acid)-poly(2-ethyl-2-oxazoline)-polyethyleneimine-CHAPS,
poly(methacrylic acid)-polyethyleneimine-Pluronic-Ficoll,
poly(methacrylic acid)-Pluronic-Ficoll-CHAPS,
poly(methacrylic acid)-Pluronic-polyethyleneimine-CHAPS,
poly(methacrylic acid)-Ficoll-polyethyleneimine-CHAPS,
poly(2-ethyl-2-oxazoline)-Pluronic-Ficoll-polyethyleneimine,
poly(2-ethyl-2-oxazoline)-Pluronic-Ficoll-CHAPS,
poly(2-ethyl-2-oxazoline)-Pluronic-poly ethyleneimine-CHAPS,
poly(2-ethyl-2-oxazoline)-Ficoll-polyethyleneimine-CHAPS, and
Pluronic F68-Ficoll-polyethyleneimine-CHAPS. In some specific embodiments, each phase of the MPS is aqueous phase.

In some embodiments, the multi-phase system is a three-phase system and the phase components in the three phases are a combination of phase components selected from the group consisting of
poly(methacrylic acid)-poly(2-ethyl-2-oxazoline)-Pluronic,
poly(methacrylic acid)-poly(2-ethyl-2-oxazoline)-Ficoll,
poly(methacrylic acid)-poly(2-ethyl-2-oxazoline)-polyethyleneimine,
poly(methacrylic acid)-poly(2-ethyl-2-oxazoline)-CHAPS,
poly(methacrylic acid)-Pluronic-Ficoll,
poly(methacrylic acid)-Pluronic-polyethyleneimine,
poly(methacrylic acid)-Pluronic-CHAPS,
poly(methacrylic acid)-Ficoll-polyethyleneimine,
poly(methacrylic acid)-Ficoll-CHAPS,
poly(methacrylic acid)-polyethyleneimine-CHAPS,
poly(2-ethyl-2-oxazoline)-Pluronic-Ficoll,
poly(2-ethyl-2-oxazoline)-Pluronic-CHAPS,
poly(2-ethyl-2-oxazoline)-Pluronic-poly ethyleneimine,
poly(2-ethyl-2-oxazoline)-Ficoll-polyethyleneimine,
poly(2-ethyl-2-oxazoline)-Ficoll-CHAPS,
poly(2-ethyl-2-oxazoline)-poly ethyleneimine-CHAPS,
Pluronic-Ficoll-poly ethyleneimine,
Pluronic-Ficoll-CHAPS,
Pluronic-polyethyleneimine-CHAPS, and
Ficoll-polyethyleneimine-CHAPS. In some specific embodiments, each phase of the MPS is aqueous phase.

In some embodiments, the multi-phase system is a two-phase system and the phase components in the two phases are a combination of phase components selected from the group consisting of
poly(methacrylic acid)-poly(2-ethyl-2-oxazoline),
poly(methacrylic acid)-Pluronic,
poly(methacrylic acid)-Ficoll,
poly(methacrylic acid)-polyethyleneimine,
poly(methacrylic acid)-CHAPS,
poly(2-ethyl-2-oxazoline)-polyethyleneimine,
poly(2-ethyl-2-oxazoline)-Ficoll,
poly(2-ethyl-2-oxazoline)-Pluronic,
poly(2-ethyl-2-oxazoline)-CHAPS,
Pluronic F68-polyethyleneimine,
polyethyleneimine-Ficoll,
polyethyleneimine-CHAPS,
Pluronic-Ficoll,
Pluronic-CHAPS, and
Ficoll-CHAPS. In some embodiments, the MPS comprises a mixture of aqueous and organic phases.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of poly(methacrylic acid), poly(2-ethyl-2-oxazoline), poly(ethylene glycol), Ficoll, and Tween, with the proviso that the multi-phase system does not include:
an aqueous two-phase system wherein the phase components in the two phases are a combination selected from the group consisting poly(ethylene glycol)-Ficoll, and poly(ethylene glycol)-Tween. In some embodiments, the MPS comprises a mixture of aqueous and organic phases. In some embodiments, the MPS comprises all aqueous phases. In some embodiments, the MPS comprises all organic phases.

In some embodiments, the multi-phase system is a five-phase system and the phase components in the five phases are poly(methacrylic acid), poly(2-ethyl-2-oxazoline), poly (ethylene glycol), Ficoll, and Tween, respectively. In some specific embodiments, each phase of the MPS is aqueous phase.

In some embodiments, the multi-phase system is a four-phase system and the phase components in the four phases are a combination of phase components selected from the group consisting of
poly(methacrylic acid)-poly(2-ethyl-2-oxazoline)-poly(ethylene glycol)-Ficoll,
poly(methacrylic acid)-poly(2-ethyl-2-oxazoline)-poly(ethylene glycol)-Tween,
poly(2-ethyl-2-oxazoline)-poly(ethylene glycol)-Ficoll-Tween,
poly(methacrylic acid)-poly(ethylene glycol)-Ficoll-Tween, and
poly(methacrylic acid)-poly(2-ethyl-2-oxazoline)-Ficoll-Tween. In some specific embodiments, each phase of the MPS is aqueous phase.

In some embodiments, wherein the multi-phase system is a three-phase system and the phase components in the three phases are a combination of phase components selected from the group consisting of
poly(methacrylic acid)-poly(2-ethyl-2-oxazoline)-poly(ethylene glycol),
poly(methacrylic acid)-poly(2-ethyl-2-oxazoline)-Ficoll,
poly(methacrylic acid)-poly(2-ethyl-2-oxazoline)-Tween,
poly(methacrylic acid)-poly(ethylene glycol)-Ficoll,
poly(methacrylic acid)-poly(ethylene glycol)-Tween,
poly(methacrylic acid)-Ficoll-Tween,
poly(2-ethyl-2-oxazoline)-poly(ethylene glycol)-Ficoll,
poly(2-ethyl-2-oxazoline)-poly(ethylene glycol)-Tween,
poly(2-ethyl-2-oxazoline)-Ficoll-Tween, and
poly(ethylene glycol)-Ficoll-Tween. In some specific embodiments, each phase of the MPS is aqueous phase.

In some embodiments, the multi-phase system is a two-phase system and the phase components in the two phases are a combination of phase components selected from the group consisting of
poly(methacrylic acid)-poly(2-ethyl-2-oxazoline),
poly(methacrylic acid)-poly(ethylene glycol),
poly(methacrylic acid)-Tween,
poly(methacrylic acid)-Ficoll,
poly(2-ethyl-2-oxazoline)-poly(ethylene glycol), poly(2-ethyl-2-oxazoline)-Ficoll,
poly(2-ethyl-2-oxazoline)-Tween, and
Ficoll-Tween. In some specific embodiments, each phase of the two-phase MPS is aqueous phase.

In yet another aspect, multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of poly(methacrylic acid), poly(2-ethyl-2-oxazoline), poly(ethylene glycol), polyacrylamide, and Tween,
with the proviso that the multi-phase system does not include:
an aqueous two-phase system wherein the phase components in the two phases are a combination of poly(ethylene glycol)-Tween. In some embodiments, the MPS comprises a mixture of aqueous and organic phases. In some embodiments, the MPS comprises all aqueous phases. In some embodiments, the MPS comprises all organic phases.

In some embodiments, the multi-phase system is a five-phase system and the phase components in the five phases are poly(methacrylic acid), poly(2-ethyl-2-oxazoline), poly(ethylene glycol), polyacrylamide, and Tween, respectively. In some specific embodiments, each phase of the MPS is aqueous phase.

In some embodiments, the multi-phase system is a four-phase system and the phase components in the four phases are a combination of phase components selected from the group consisting of
poly(methacrylic acid)-poly(2-ethyl-2-oxazoline)-poly(ethylene glycol)-polyacrylamide,
poly(methacrylic acid)-poly(2-ethyl-2-oxazoline)-poly(ethylene glycol)-Tween,
poly(2-ethyl-2-oxazoline)-poly(ethylene glycol)-polyacrylamide-Tween,
poly(methacrylic acid)-poly(ethylene glycol)-polyacrylamide-Tween, and
poly(methacrylic acid)-poly(2-ethyl-2-oxazoline)-polyacrylamide-Tween. In some specific embodiments, each phase of the MPS is aqueous phase.

In some embodiments, the multi-phase system is a three-phase system and the phase components in the three phases are a combination of phase components selected from the group consisting of
poly(methacrylic acid)-poly(2-ethyl-2-oxazoline)-poly(ethylene glycol),
poly(methacrylic acid)-poly(2-ethyl-2-oxazoline)-polyacrylamide,
poly(methacrylic acid)-poly(2-ethyl-2-oxazoline)-Tween,
poly(methacrylic acid)-poly(ethylene glycol)-polyacrylamide,
poly(methacrylic acid)-poly(ethylene glycol)-Tween,
poly(methacrylic acid)-polyacrylamide-Tween,
poly(2-ethyl-2-oxazoline)-poly(ethylene glycol)-polyacrylamide,
poly(2-ethyl-2-oxazoline)-poly(ethylene glycol)-Tween,
poly(2-ethyl-2-oxazoline)-polyacrylamide-Tween, and
poly(ethylene glycol)-polyacrylamide-Tween. In some specific embodiments, each phase of the MPS is aqueous phase.

In some embodiments, the multi-phase system is a two-phase system and the phase components in the two phases are a combination of phase components selected from the group consisting of
poly(methacrylic acid)-poly(2-ethyl-2-oxazoline),
poly(methacrylic acid)-poly(ethylene glycol),
poly(methacrylic acid)-Tween,
poly(methacrylic acid)-polyacrylamide,
poly(2-ethyl-2-oxazoline)-poly(ethylene glycol),
poly(2-ethyl-2-oxazoline)-polyacrylamide,
poly(2-ethyl-2-oxazoline)-Tween,
poly(ethylene glycol)-polyacrylamide, and
polyacrylamide-Tween. In some specific embodiments, each phase of the MPS is aqueous phase.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of poly(vinyl alcohol), poly(2-ethyl-2-oxazoline), poly(ethylene glycol), polyacrylamide, and Tween,
with the proviso that the multi-phase system does not include:
an aqueous two-phase system wherein the phase components in the two phases are a combination selected from the group consisting of poly(vinyl alcohol)-poly(ethylene glycol) and poly(ethylene glycol)-Tween. In some embodiments, the MPS comprises a mixture of aqueous and organic phases. In some embodiments, the MPS comprises all aqueous phases. In some embodiments, the MPS comprises all organic phases.

In some embodiments, the multi-phase system is a five-phase system and the phase components in the five phases are poly(vinyl alcohol), poly(2-ethyl-2-oxazoline), poly(ethylene glycol), polyacrylamide, and Tween, respectively. In some specific embodiments, each phase of the MPS is aqueous phase.

In some embodiments, wherein the multi-phase system is a four-phase system and the phase components in the four phases are a combination of phase components selected from the group consisting of
poly(vinyl alcohol)-poly(2-ethyl-2-oxazoline)-poly(ethylene glycol)-polyacrylamide,
poly(vinyl alcohol)-poly(2-ethyl-2-oxazoline)-poly(ethylene glycol)-Tween,
poly(2-ethyl-2-oxazoline)-poly(ethylene glycol)-polyacrylamide-Tween,
poly(vinyl alcohol)-poly(ethylene glycol)-polyacrylamide-Tween, and
poly(vinyl alcohol)-poly(2-ethyl-2-oxazoline)-polyacrylamide-Tween. In some specific embodiments, each phase of the MPS is aqueous phase.

In some embodiments, the multi-phase system is a three-phase system and the phase components in the three phases are a combination of phase components selected from the group consisting of
poly(vinyl alcohol)-poly(2-ethyl-2-oxazoline)-poly(ethylene glycol),
poly(vinyl alcohol)-poly(2-ethyl-2-oxazoline)-polyacrylamide, poly(vinyl alcohol)-poly(2-ethyl-2-oxazoline)-Tween,
poly(vinyl alcohol)-poly(ethylene glycol)-polyacrylamide,
poly(vinyl alcohol)-poly(ethylene glycol)-Tween,
poly(vinyl alcohol)-polyacrylamide-Tween,
poly(2-ethyl-2-oxazoline)-poly(ethylene glycol)-polyacrylamide,
poly(2-ethyl-2-oxazoline)-poly(ethylene glycol)-Tween,
poly(2-ethyl-2-oxazoline)-polyacrylamide-Tween, and
poly(ethylene glycol)-polyacrylamide-Tween. In some specific embodiments, each phase of the MPS is aqueous phase.

In some embodiments, the multi-phase system is a two-phase system and the phase components in the two phases are a combination of phase components selected from the group consisting of
poly(vinyl alcohol)-poly(2-ethyl-2-oxazoline),
poly(vinyl alcohol)-Tween,
poly(vinyl alcohol)-polyacrylamide,
poly(2-ethyl-2-oxazoline)-poly(ethylene glycol),
poly(2-ethyl-2-oxazoline)-polyacrylamide,
poly(2-ethyl-2-oxazoline)-Tween,
poly(ethylene glycol)-polyacrylamide, and
polyacrylamide-Tween. In some specific embodiments, each phase of the MPS is aqueous phase.

In yet another aspect, a multi-phase system comprising two or more phases is described, wherein
  each phase comprises a phase component, wherein the phase component is selected from the group consisting of a polymer, a surfactant, and a combination thereof;
  each of the two or more phases has a different density and the phases, taken together, represent a density gradient; and
  the phases are phase-separated from each other, wherein the phase components are selected from the groups consisting of poly(methacrylic acid), poly(2-ethyl-2-oxazoline), poly(ethylene glycol), polyethyleneimine, and 1-O-Octyl-β-D-glucopyranoside, with the proviso that the multi-phase system does not include:
an aqueous two-phase system wherein the phase components in the two phases are a combination of 1-O-Octyl-β-D-glucopyranoside-poly(ethylene glycol). In some embodiments, the MPS comprises a mixture of aqueous and organic phases. In some embodiments, the MPS comprises all aqueous phases. In some embodiments, the MPS comprises all organic phases.

In some embodiments, the multi-phase system is a five-phase system and the phase components in the five phases are poly(methacrylic acid), poly(2-ethyl-2-oxazoline), poly(ethylene glycol), polyethyleneimine, and 1-O-Octyl-β-D-glucopyranoside, respectively. In some specific embodiments, each phase of the MPS is aqueous phase.

In some embodiments, the multi-phase system is a four-phase system and the phase components in the four phases are a combination of phase components selected from the group consisting of
poly(methacrylic acid)-poly(2-ethyl-2-oxazoline)-poly(ethylene glycol)-polyethyleneimine,
poly(methacrylic acid)-poly(2-ethyl-2-oxazoline)-poly(ethylene glycol)-1-O-Octyl-β-D-glucopyranoside,
poly(2-ethyl-2-oxazoline)-poly(ethylene glycol)-polyethyleneimine-1-O-Octyl-3-D-glucopyranoside,
poly(methacrylic acid)-poly(ethylene glycol)-polyethyleneimine-1-O-Octyl-β-D-glucopyranoside, and
poly(methacrylic acid)-poly(2-ethyl-2-oxazoline)-polyethyleneimine-1-O-Octyl-3-D-glucopyranoside. In some specific embodiments, each phase of the MPS is aqueous phase.

In some embodiments, the multi-phase system is a three-phase system and the phase components in the three phases are a combination of phase components selected from the group consisting of
poly(methacrylic acid)-poly(2-ethyl-2-oxazoline)-poly(ethylene glycol),
poly(methacrylic acid)-poly(2-ethyl-2-oxazoline)-polyethyleneimine,
poly(methacrylic acid)-poly(2-ethyl-2-oxazoline)-1-O-Octyl-β-D-glucopyranoside,
poly(methacrylic acid)-poly(ethylene glycol)-polyethyleneimine,
poly(methacrylic acid)-poly(ethylene glycol)-1-O-Octyl-β-D-glucopyranoside,
poly(methacrylic acid)-polyethyleneimine-1-O-Octyl-β-D-glucopyranoside,
poly(2-ethyl-2-oxazoline)-poly(ethylene glycol)-polyethyleneimine,
poly(2-ethyl-2-oxazoline)-poly(ethylene glycol)-1-O-Octyl-β-D-glucopyranoside,
poly(2-ethyl-2-oxazoline)-polyethyleneimine-1-O-Octyl-β-D-glucopyranoside, and
poly(ethylene glycol)-polyethyleneimine-1-O-Octyl-β-D-glucopyranoside. In some specific embodiments, each phase of the MPS is aqueous phase.

In some embodiments, the multi-phase system is a two-phase system and the phase components in the two phases are a combination of phase components selected from the group consisting of
poly(methacrylic acid)-poly(2-ethyl-2-oxazoline),
poly(methacrylic acid)-poly(ethylene glycol),
poly(methacrylic acid)-1-O-Octyl-β-D-glucopyranoside,
poly(methacrylic acid)-polyethyleneimine,
poly(2-ethyl-2-oxazoline)-poly(ethylene glycol),
poly(2-ethyl-2-oxazoline)-polyethyleneimine,
poly(2-ethyl-2-oxazoline)-1-O-Octyl-β-D-glucopyranoside,
poly(ethylene glycol)-polyethyleneimine, and
polyacrylamide-1-O-Octyl-β-D-glucopyranoside. In some specific embodiments, each phase of the two-phase MPS is aqueous phase.

In yet another aspect, a multi-phase system comprising two or more phases is described, wherein
  each phase comprises a phase component, wherein the phase component is selected from the group consisting of a polymer, a surfactant, and a combination thereof;
  each of the two or more phases has a different density and the phases, taken together, represent a density gradient; and
  the phases are phase-separated from each other, wherein the phase components are selected from the groups consisting of poly(vinyl alcohol), poly(2-ethyl-2-oxazoline), dextran, Ficoll, and Pluronic,
  with the proviso that the multi-phase system does not include:
an aqueous two-phase system wherein the phase components in the two phases are a combination selected from the group consisting of poly(vinyl alcohol)-dextran, and dextran-Ficoll. In some embodiments, the MPS comprises a mixture of aqueous and organic phases. In some embodiments, the MPS comprises all aqueous phases. In some embodiments, the MPS comprises all organic phases.

In some embodiments, the multi-phase system is a five-phase system and the phase components in the five phases are poly(vinyl alcohol), poly(2-ethyl-2-oxazoline), dextran, Ficoll, and Pluronic, respectively. In some specific embodiments, each phase of the MPS is aqueous phase.

In some embodiments, the multi-phase system is a four-phase system and the phase components in the four phases are a combination of phase components selected from the group consisting of poly(vinyl alcohol)-poly(2-ethyl-2-oxazoline)-dextran-Ficoll,
poly(vinyl alcohol)-poly(2-ethyl-2-oxazoline)-dextran-Pluronic,
poly(vinyl alcohol)-poly(2-ethyl-2-oxazoline)-Ficoll-Pluronic,
poly(vinyl alcohol)-dextran-Ficoll-Pluronic, and
poly(2-ethyl-2-oxazoline)-dextran-Ficoll-Pluronic. In some specific embodiments, each phase of the MPS is aqueous phase.

In some embodiments, the multi-phase system is a three-phase system and the phase components in the three phases are a combination of phase components selected from the group consisting of poly(vinyl alcohol)-poly(2-ethyl-2-oxazoline)-dextran,
poly(vinyl alcohol)-poly(2-ethyl-2-oxazoline)-Ficoll,
poly(vinyl alcohol)-poly(2-ethyl-2-oxazoline)-Pluronic,
poly(2-ethyl-2-oxazoline)-dextran-Ficoll,
poly(2-ethyl-2-oxazoline)-dextran-Pluronic,
poly(2-ethyl-2-oxazoline)-Ficoll-Pluronic,
dextran-Ficoll-Pluronic,
poly(vinyl alcohol)-dextran-Ficoll,
poly(vinyl alcohol)-dextran-Pluronic, and
poly(vinyl alcohol)-Ficoll-Pluronic. In some specific embodiments, each phase of the MPS is aqueous phase.

In some embodiments, the multi-phase system is a two-phase system and the phase components in the two phases are a combination of phase components selected from the group consisting of poly(vinyl alcohol)-poly(2-ethyl-2-oxazoline),
poly(vinyl alcohol)-Ficoll,
poly(vinyl alcohol)-Pluronic,
poly(2-ethyl-2-oxazoline)-dextran,
poly(2-ethyl-2-oxazoline)-Ficoll,
poly(2-ethyl-2-oxazoline)-Pluronic,
dextran-Pluronic, and
Ficoll-Pluronic. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(2-ethyl-2-oxazoline), poly(ethylene glycol), dextran, Ficoll, and CHAPS, with the proviso that the multi-phase system does not include:

an aqueous three-phase system wherein the phase components in the three phases are a combination of poly (ethylene glycol)-dextran-Ficoll; or an aqueous two-phase system wherein the phase components in the two phases are a combination selected from the group consisting of dextran-Ficoll, poly(ethylene glycol)-Ficoll, and poly(ethylene glycol)-dextran. In some embodiments, the MPS comprises a mixture of aqueous and organic phases. In some embodiments, the MPS comprises all aqueous phases. In some embodiments, the MPS comprises all organic phases.

In some embodiments, the multi-phase system is a five-phase system and the phase components in the five phases are poly(2-ethyl-2-oxazoline), poly(ethylene glycol), dextran, Ficoll, and CHAPS, respectively. In some specific embodiments, each phase of the MPS is aqueous phase.

In some embodiments, the multi-phase system is a four-phase system and the phase components in the four phases are a combination of phase components selected from the group consisting of poly(2-ethyl-2-oxazoline)-poly(ethylene glycol)-dextran-Ficoll,
poly(2-ethyl-2-oxazoline)-poly(ethylene glycol)-dextran-CHAPS,
poly(2-ethyl-2-oxazoline)-poly(ethylene glycol)-Ficoll-CHAPS,
poly(2-ethyl-2-oxazoline)-dextran-Ficoll-CHAPS, and
poly(ethylene glycol)-dextran-Ficoll-CHAPS. In some specific embodiments, each phase of the MPS is aqueous phase.

In some embodiments, the multi-phase system is a three-phase system and the phase components in the three phases are a combination of phase components selected from the group consisting of poly(2-ethyl-2-oxazoline)-poly(ethylene glycol)-dextran,
poly(2-ethyl-2-oxazoline)-poly(ethylene glycol)-Ficoll,
poly(2-ethyl-2-oxazoline)-poly(ethylene glycol)-CHAPS,
poly(2-ethyl-2-oxazoline)-dextran-Ficoll,
poly(2-ethyl-2-oxazoline)-dextran-Ficoll,
poly(2-ethyl-2-oxazoline)-Ficoll-CHAPS,
poly(ethylene glycol)-dextran-CHAPS,
poly(ethylene glycol)-Ficoll-CHAPS, and
dextran-Ficoll-CHAPS. In some specific embodiments, each phase of the MPS is aqueous phase.

In some embodiments, the multi-phase system is a two-phase system and the phase components in the two phases are a combination of phase components selected from the group consisting of poly(2-ethyl-2-oxazoline)-poly(ethylene glycol),
poly(2-ethyl-2-oxazoline)-dextran,
poly(2-ethyl-2-oxazoline)-Ficoll,
poly(2-ethyl-2-oxazoline)-CHAPS,
poly(ethylene glycol)-CHAPS,
dextran-CHAPS, and
Ficoll-CHAPS. In some specific embodiments, each phase of the two-phase MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(2-ethyl-2-oxazoline), Pluronic, dextran, Ficoll, and CHAPS, with the proviso that the multi-phase system does not include:

an aqueous two-phase system wherein the phase components in the two phases are a combination of dextran-Ficoll. In some embodiments, the MPS comprises a mixture of aqueous and organic phases. In some embodiments, the MPS comprises all aqueous phases. In some embodiments, the MPS comprises all organic phases.

In some embodiments, the multi-phase system is a five-phase system and the phase components in the five phases are poly(2-ethyl-2-oxazoline), Pluronic F68, dextran, Ficoll, and CHAPS, respectively. In some specific embodiments, each phase of the MPS is aqueous phase.

In some embodiments, the multi-phase system is a four-phase system and the phase components in the four phases are a combination of phase components selected from the group consisting of
poly(2-ethyl-2-oxazoline)-Pluronic-dextran-Ficoll,
poly(2-ethyl-2-oxazoline)-Pluronic-dextran-CHAPS,
poly(2-ethyl-2-oxazoline)-Pluronic-Ficoll-CHAPS,
poly(2-ethyl-2-oxazoline)-dextran-Ficoll-CHAPS, and
Pluronic-dextran-Ficoll-CHAPS. In some specific embodiments, each phase of the MPS is aqueous phase.

In some embodiments, the multi-phase system is a three-phase system and the phase components in the three phases are a combination of phase components selected from the group consisting of
poly(2-ethyl-2-oxazoline)-Pluronic-dextran,
poly(2-ethyl-2-oxazoline)-Pluronic-Ficoll,
poly(2-ethyl-2-oxazoline)-Pluronic-CHAPS,
poly(2-ethyl-2-oxazoline)-dextran-Ficoll,
poly(2-ethyl-2-oxazoline)-dextran-Ficoll,
poly(2-ethyl-2-oxazoline)-Ficoll-CHAPS,
Pluronic-dextran-Ficoll
Pluronic-dextran-CHAPS,
Pluronic-Ficoll-CHAPS, and
dextran-Ficoll-CHAPS. In some specific embodiments, each phase of the MPS is aqueous phase.

In some embodiments, the multi-phase system is a two-phase system and the phase components in the two phases are a combination of phase components selected from the group consisting of
poly(2-ethyl-2-oxazoline)-Pluronic,
poly(2-ethyl-2-oxazoline)-dextran,
poly(2-ethyl-2-oxazoline)-Ficoll,
poly(2-ethyl-2-oxazoline)-CHAPS,
Pluronic-dextran,
Pluronic-Ficoll,
Pluronic-CHAPS,
dextran-CHAPS, and
Ficoll-CHAPS. In some specific embodiments, each phase of the two-phase MPS is aqueous phase.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of poly(methacrylic acid), poly(2-ethyl-2-oxazoline), polyacrylamide, and Triton. In some embodiments, the MPS comprises a mixture of aqueous and organic phases. In some embodiments, the MPS comprises all aqueous phases. In some embodiments, the MPS comprises all organic phases.

In some embodiments, the multi-phase system is a four-phase system and the phase components in the four phases are poly(methacrylic acid), poly(2-ethyl-2-oxazoline), polyacrylamide, and Triton, respectively. In some specific embodiments, each phase of the MPS is aqueous phase.

In some embodiments, the multi-phase system is a three-phase system and the phase components in the three phases are a combination of phase components selected from the group consisting of
poly(methacrylic acid)-poly(2-ethyl-2-oxazoline)-polyacrylamide,
poly(methacrylic acid)-poly(2-ethyl-2-oxazoline)-Triton,
poly(methacrylic acid)-polyacrylamide-Triton, and
poly(2-ethyl-2-oxazoline)-polyacrylamide-Triton. In some embodiments, the multi-phase system is a two-phase system and the phase components in the two phases are a combination of phase components selected from the group consisting of
poly(methacrylic acid)-poly(2-ethyl-2-oxazoline),
poly(methacrylic acid)-polyacrylamide,
poly(methacrylic acid)-Triton,
poly(2-ethyl-2-oxazoline)-polyacrylamide,
poly(2-ethyl-2-oxazoline)-Triton, and
polyacrylamide-Triton. In some specific embodiments, each phase of the MPS is aqueous phase.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of poly(vinyl alcohol), poly(2-ethyl-2-oxazoline), dextran, and Ficoll,
with the proviso that the multi-phase system does not include:
an aqueous two-phase system wherein the phase components in the two phases are a combination selected from the group consisting of dextran-Ficoll, and dextran-poly(vinyl alcohol). In some embodiments, the MPS comprises a mixture of aqueous and organic phases. In some embodiments, the MPS comprises all aqueous phases. In some embodiments, the MPS comprises all organic phases.

In some embodiments, the multi-phase system is a four-phase system and the phase components in the four phases are poly(vinyl alcohol), poly(2-ethyl-2-oxazoline), dextran, and Ficoll, respectively. In some embodiments, the multi-phase system is a three-phase system and the phase components in the three phases are a combination of phase components selected from the group consisting of
poly(vinyl alcohol)-poly(2-ethyl-2-oxazoline)-dextran,
poly(vinyl alcohol)-poly(2-ethyl-2-oxazoline)-Ficoll,
poly(2-ethyl-2-oxazoline)-dextran-Ficoll, and
poly(vinyl alcohol)-dextran-Ficoll. In some embodiments, the multi-phase system is a two-phase system and the phase components in the two phases are a combination of phase components selected from the group consisting of
poly(vinyl alcohol)-poly(2-ethyl-2-oxazoline),
poly(vinyl alcohol)-dextran-Ficoll,
poly(2-ethyl-2-oxazoline)-dextran, and
poly(2-ethyl-2-oxazoline)-Ficoll. In some specific embodiments, each phase of the MPS is aqueous phase.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of poly(vinyl alcohol), poly(2-ethyl-2-oxazoline), polyacrylamide, and Pluronic,
with the proviso that the multi-phase system does not include:
an aqueous two-phase system wherein the phase components in the two phases are a combination of polyacrylamide-poly(vinyl alcohol). In some embodiments, the MPS comprises a mixture of aqueous and organic phases. In some embodiments, the MPS comprises all aqueous phases. In some embodiments, the MPS comprises all organic phases.

In some embodiments, the multi-phase system is a four-phase system and the phase components in the four phases are poly(vinyl alcohol), poly(2-ethyl-2-oxazoline), polyacrylamide, and Pluronic, respectively. In some embodiments, the multi-phase system is a three-phase system and the phase components in the three phases are a combination of phase components selected from the group consisting of
poly(vinyl alcohol)-poly(2-ethyl-2-oxazoline)-polyacrylamide,
poly(vinyl alcohol)-poly(2-ethyl-2-oxazoline)-Pluronic,
poly(vinyl alcohol)-polyacrylamide-Pluronic, and
poly(2-ethyl-2-oxazoline)-polyacrylamide-Pluronic. In some embodiments, the multi-phase system is a two-phase system and the phase components in the two phases are a combination of phase components selected from the group consisting of
poly(vinyl alcohol)-poly(2-ethyl-2-oxazoline),
poly(vinyl alcohol)-Pluronic,
poly(2-ethyl-2-oxazoline)-polyacrylamide,
poly(2-ethyl-2-oxazoline)-Pluronic, and
polyacrylamide-Pluronic. In some specific embodiments, each phase of the MPS is aqueous phase.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of dextran, Ficoll, hydroxyethyl cellulose, and Tween, with the proviso that the multi-phase system does not include:
an aqueous two-phase system wherein the phase components in the two phases are a combination selected from the group consisting of dextran-Ficoll and dextran-Tween. In some embodiments, the MPS comprises a mixture of aqueous and organic phases. In some embodiments, the MPS comprises all aqueous phases. In some embodiments, the MPS comprises all organic phases.

In some embodiments, the multi-phase system is a four-phase system and the phase components in the four phases are dextran, Ficoll, hydroxyethyl cellulose, and Tween, respectively. In some embodiments, the multi-phase system is a three-phase system and the phase components in the three phases are a combination of phase components selected from the group consisting of
dextran-Ficoll-hydroxyethyl cellulose,
dextran-Ficoll-Tween,
dextran-hydroxyethyl cellulose-Tween, and
Ficoll-hydroxyethyl cellulose-Tween. In some embodiments, the multi-phase system is a two-phase system and the phase components in the two phases are a combination of phase components selected from the group consisting of
dextran-hydroxyethyl cellulose,
Ficoll-hydroxyethyl cellulose,
Ficoll-Tween, and
hydroxyethyl cellulose-Tween. In some specific embodiments, each phase of the MPS is aqueous phase.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of dextran, Ficoll, hydroxyethyl cellulose, and Triton, with the proviso that the multi-phase system does not include:
an aqueous two-phase system wherein the phase components in the two phases are a combination selected from the group consisting of dextran-Ficoll and dextran-Triton. In some embodiments, the MPS comprises a mixture of aqueous and organic phases. In some embodiments, the MPS comprises all aqueous phases. In some embodiments, the MPS comprises all organic phases.

In some embodiments, the multi-phase system is a four-phase system and the phase components in the four phases are dextran, Ficoll, hydroxyethyl cellulose, and Triton, respectively. In some embodiments, the multi-phase system is a three-phase system and the phase components in the three phases are a combination of phase components selected from the group consisting of
dextran-Ficoll-hydroxyethyl cellulose,
dextran-Ficoll-Triton,
dextran-hydroxyethyl cellulose-Triton, and
Ficoll-hydroxyethyl cellulose-Triton. In some embodiments, the multi-phase system is a two-phase system and the phase components in the two phases are a combination of phase components selected from the group consisting of
dextran-hydroxyethyl cellulose,
Ficoll-hydroxyethyl cellulose,
Ficoll-Triton, and
hydroxyethyl cellulose-Triton. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(methacrylic acid), poly(2-ethyl-2-oxazoline), poly(ethylene glycol), and poly(diallyldimethyl ammonium chloride). In some embodiments, the multi-phase system is a four-phase system and the phase components in the four phases are poly(methacrylic acid), poly(2-ethyl-2-oxazoline), poly(ethylene glycol), and poly(diallyldimethyl ammonium chloride), respectively. In some embodiments, wherein the multi-phase system is a three-phase system and the phase components in the three phases are a combination of phase components selected from the group consisting of poly(methacrylic acid)-poly(2-ethyl-2-oxazoline)-poly(ethylene glycol),
poly(methacrylic acid)-poly(2-ethyl-2-oxazoline)-poly(diallyldimethyl ammonium chloride),
poly(methacrylic acid)-poly(ethylene glycol)-poly(diallyldimethyl ammonium chloride), and
poly(2-ethyl-2-oxazoline)-poly(ethylene glycol)-poly(diallyldimethyl ammonium chloride). In some embodiments, the multi-phase system is a two-phase system and the phase components in the two phases are a combination of phase components selected from the group consisting of
poly(methacrylic acid)-poly(2-ethyl-2-oxazoline, poly (methacrylic acid)-poly(ethylene glycol), poly(methacrylic acid)-poly(diallyldimethyl ammonium chloride), poly(2-ethyl-2-oxazoline)-poly(ethylene glycol), poly(2-ethyl-2-oxazoline)-poly(diallyldimethyl ammonium chloride), and poly(ethylene glycol)-poly(diallyldimethyl ammonium chloride). In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(methacrylic acid), poly(2-ethyl-2-oxazoline), Ficoll, and Triton. In some embodiments, the multi-phase system is a four-phase system and the phase components in the four phases are poly(methacrylic acid), poly(2-ethyl-2-oxazoline), Ficoll, and Triton, respectively. In some embodiments, the multi-phase system is a three-phase system and the phase components in the three phases are a combination of phase components selected from the group consisting of poly(methacrylic acid)-poly(2-ethyl-2-oxazoline)-Ficoll, poly(methacrylic acid)-poly(2-ethyl-2-oxazoline)-Triton, poly(methacrylic acid)-Ficoll-Triton, and poly(2-ethyl-2-oxazoline)-Ficoll-Triton. In some embodiments, the multi-phase system is a two-phase system and the phase components in the two phases are a combination of phase components selected from the group consisting of poly(methacrylic acid)-poly(2-ethyl-2-oxazoline), poly(methacrylic acid)-Ficoll, poly(methacrylic acid)-Triton, poly(2-ethyl-2-oxazoline)-Ficoll, poly(2-ethyl-2-oxazoline)-Triton, and Ficoll-Triton. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(vinyl alcohol), poly(2-ethyl-2-oxazoline), poly(ethylene glycol), and poly(diallyldimethyl ammonium chloride), with the proviso that the multi-phase system does not include: an aqueous two-phase system wherein the phase components in the two phases are a combination of poly(ethylene glycol)-poly(vinyl alcohol). In some embodiments, the multi-phase system is a four-phase system and the phase components in the four phases are poly(vinyl alcohol), poly(2-ethyl-2-oxazoline), poly(ethylene glycol), and poly(diallyldimethyl ammonium chloride), respectively. In some embodiments, the multi-phase system is a three-phase system and the phase components in the three phases are a combination of phase components selected from the group consisting of poly(vinyl alcohol)-poly(2-ethyl-2-oxazoline)-poly(ethylene glycol), poly(vinyl alcohol)-poly(2-ethyl-2-oxazoline)-poly(diallyldimethyl ammonium chloride), poly(vinyl alcohol)-poly(ethylene glycol)-poly(diallyldimethyl ammonium chloride), and poly(2-ethyl-2-oxazoline)-poly(ethylene glycol)-poly(diallyldimethyl ammonium chloride). In some embodiments, the multi-phase system is a two-phase system and the phase components in the two phases are a combination of phase components selected from the group consisting of poly(vinyl alcohol)-poly(2-ethyl-2-oxazoline, poly(vinyl alcohol)-poly(diallyldimethyl ammonium chloride), poly(2-ethyl-2-oxazoline)-poly(ethylene glycol), poly(2-ethyl-2-oxazoline)-poly(diallyldimethyl ammonium chloride), and poly(ethylene glycol)-poly(diallyldimethyl ammonium chloride). In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(2-ethyl-2-oxazoline), dextran, Ficoll, and Triton, with the proviso that the multi-phase system does not include: an aqueous two-phase system wherein the phase components in the two phases are a combination selected from the group consisting of dextran-Ficoll and dextran-Triton. In some embodiments, the multi-phase system is a four-phase system and the phase components in the four phases are poly(2-ethyl-2-oxazoline), dextran, Ficoll, and Triton, respectively. In some embodiments, the multi-phase system is a three-phase system and the phase components in the three phases are a combination of phase components selected from the group consisting of poly(2-ethyl-2-oxazoline)-dextran-Ficoll, poly(2-ethyl-2-oxazoline)-dextran-Triton, poly(2-ethyl-2-oxazoline)-Ficoll-Triton, and dextran-Ficoll-Triton. In some embodiments, the multi-phase system is a two-phase system and the phase components in the two phases are a combination of phase components selected from the group consisting of poly(2-ethyl-2-oxazoline)-dextran, poly(2-ethyl-2-oxazoline)-Ficoll, poly(2-ethyl-2-oxazoline)-Triton, and Ficoll-Triton. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(2-ethyl-2-oxazoline), dextran, Ficoll, and CHAPS, with the proviso that the multi-phase system does not include: an aqueous two-phase system wherein the phase components in the two phases are a combination of dextran-Ficoll. In some embodiments, the multi-phase system is a four-phase system and the phase components in the four phases are poly(2-ethyl-2-oxazoline), dextran, Ficoll, and CHAPS, respectively. In some embodiments, the multi-phase system is a three-phase system and the phase components in the three phases are a combination of phase components selected from the group consisting of poly(2-ethyl-2-oxazoline)-dextran-Ficoll, poly(2-ethyl-2-oxazoline)-dextran-CHAPS, poly(2-ethyl-2-oxazoline)-Ficoll-CHAPS, and dextran-Ficoll-CHAPS. In some embodiments, the multi-phase system is a two-phase system and the phase components in the two phases are a combination of phase components selected from the group consisting of poly(2-ethyl-2-oxazoline)-dextran, poly(2-ethyl-2-oxazoline)-Ficoll, dextran-CHAPS, poly(2-ethyl-2-oxazoline)-CHAPS, and Ficoll-CHAPS. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(acrylic acid), poly(ethylene glycol), and poly(diallyldimethyl ammonium chloride), with the proviso that the multi-phase system does not include: an aqueous two-phase system wherein the phase components in the two phases are a combination of poly(ethylene glycol)-poly(acrylic acid). In some embodiments, the multi-phase system is a three-phase system and the phase components in the three phases are poly(acrylic acid), poly(ethylene glycol), and poly(diallyldimethyl ammonium chloride), respectively. In some embodiments, the multi-phase system is a two-phase system and the phase components in the two phases are a combination of phase components selected from the group consisting of poly(acrylic acid)-poly(diallyldimethyl ammonium chloride), and poly(ethylene glycol)-poly(diallyldimethyl ammonium chloride). In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(acrylic acid), polyacrylamide, and Triton. In some embodiments, the multi-phase system is a three-phase system and the phase components in the three phases are poly(acrylic acid), polyacrylamide, and Triton, respectively. In some embodiments, the multi-phase system is a two-phase system and the phase components in the two phases are a combination of phase components selected from the group consisting of poly(acrylic acid)-polyacrylamide, poly(acrylic acid)-Triton, and polyacrylamide-Triton. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(2-ethyl-2-oxazoline), dextran sulfate, and poly(styrene sulfonic acid). In some embodiments, the multi-phase system is a three-phase system and the phase components in the three phases are poly(2-ethyl-2-oxazoline), dextran sulfate, and poly(styrene sulfonic acid), respectively. In some embodiments, the multi-phase system is a two-phase system and the phase components in the two phases are a combination of phase components selected from the group consisting of poly(2-ethyl-2-oxazoline)-dextran sulfate, poly(2-ethyl-2-oxazoline)-poly(styrene sulfonic acid), and dextran sulfate-poly(styrene sulfonic acid). In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(2-ethyl-2-oxazoline), dextran sulfate, and poly(ethylene glycol), with the proviso that the multi-phase system does not include: an aqueous two-phase system wherein the phase components in the two phases are a combination of poly(ethylene glycol)-dextran sulfate. In some embodiments, the multi-phase system is a three-phase system and the phase components in the three phases are poly(2-ethyl-2-oxazoline), dextran sulfate, and poly(ethylene glycol), respectively. In some embodiments, the multi-phase system is a two-phase system and the phase components in the two phases are a combination of phase components selected from the group consisting of poly(2-ethyl-2-oxazoline)-dextran sulfate, and poly(2-ethyl-2-oxazoline)-poly(ethylene glycol). In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(vinyl alcohol), polyethyleneimine, and poly(2-ethyl-2-oxazoline). In some embodiments, the multi-phase system is a three-phase system and the phase components in the three phases are poly(vinyl alcohol), polyethyleneimine, and poly(2-ethyl-2-oxazoline), respectively. In some embodiments, the multi-phase system is a two-phase system and the phase components in the two phases are a combination of phase components selected from the group consisting of poly(vinyl alcohol)-polyethyleneimine, poly(vinyl alcohol)-poly(2-ethyl-2-oxazoline, and poly(2-ethyl-2-oxazoline)-polyethyleneimine. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(vinyl alcohol), polyethyleneimine, and poly(2-ethyl-2-oxazoline). In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(vinyl alcohol), polyethyleneimine, and poly(2-ethyl-2-oxazoline), respectively. In some embodiments, the multi-phase system is a two-phase system and the phase components in the two phases are a combination of phase components selected from the group consisting of poly(vinyl alcohol)-polyethyleneimine, poly(vinyl alcohol)-poly(2-ethyl-2-oxazoline, and poly(2-ethyl-2-oxazoline)-polyethyleneimine. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(methacrylic acid), poly(ethylene glycol), polyvinylpyrrolidone, with the proviso that the multi-phase system does not include:

an aqueous two-phase system wherein the phase components in the two phases are a combination of poly(ethylene glycol)-polyvinylpyrrolidone. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(methacrylic acid), poly(ethylene glycol), and polyvinylpyrrolidone), respectively. In some embodiments, the multi-phase system is a two-phase system and the phase components in the two phases are a combination of phase components selected from the group consisting of poly(methacrylic acid)-poly(ethylene glycol) and poly(methacrylic acid)-polyvinylpyrrolidone. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(methacrylic acid), Ficoll, and Triton. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(methacrylic acid), Ficoll, and Triton, respectively. In some embodiments, the multi-phase system is a two-phase system and the phase components in the two phases are a combination of phase components selected from the group consisting of poly(methacrylic acid)-Triton, poly(methacrylic acid)-Ficoll, and Ficoll-Triton. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(methacrylic acid), polyacrylamide, and Zonyl. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(methacrylic acid), polyacrylamide, and Zonyl, respectively. In some embodiments, the multi-phase system is a two-phase system and the phase components in the two phases are a combination of phase components selected from the group consisting of poly(methacrylic acid)-polyacrylamide, poly(methacrylic acid)-Zonyl, and polyacrylamide-Zonyl. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof; each of the two or more phases has a different density and the phases, taken together, represent a density gradient; and the phases are phase-separated from each other, wherein the phase components are selected from the groups consisting of poly(methacrylic acid), polyacrylamide, and N,N-dimethyldodecylamine N-oxide. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(methacrylic acid), polyacrylamide, and N,N-dimethyldodecylamine N-oxide, respectively. In some embodiments, the multi-phase system is a two-phase system and the phase components in the two phases are a combination of phase components selected from the group consisting of poly(methacrylic acid)-polyacrylamide, poly(methacrylic acid)-N,N-dimethyldodecylamine N-oxide, and polyacrylamide-N,N-dimethyldodecylamine N-oxidel. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(methacrylic acid), polyethyleneimine, and carboxy-polyacrylamide. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(methacrylic acid), polyethyleneimine, and carboxy-polyacrylamide, respectively. In some embodiments, the multi-phase system is a two-phase system and the phase components in the two phases are a combination of phase components selected from the group consisting of poly(methacrylic acid)-polyethyleneimine, poly(methacrylic acid)-carboxy-polyacrylamide, and polyethyleneimine-carboxy-polyacrylamide. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(acrylic acid), poly(ethylene glycol), polyacrylamide, with the proviso that the multi-phase system does not include:

an aqueous two-phase system wherein the phase components in the two phases are a combination of poly(acrylic acid)-poly(ethylene glycol).

In some embodiments, the multi-phase system is a three-phase system and the phase components in the three phases are poly(acrylic acid), poly(ethylene glycol), and polyacrylamide, respectively. In some embodiments, the multi-phase system is a two-phase system and the phase components in the two phases are a combination of phase components selected from the group consisting of poly(acrylic acid)-polyacrylamide and poly(ethylene glycol)-polyacrylamide. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(vinyl alcohol), poly(2-ethyl-2-oxazoline), and dextran sulfate. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(vinyl alcohol), poly(2-ethyl-2-oxazoline), and dextran sulfate, respectively. In some embodiments, the multi-phase system is a two-phase system and the phase components in the two phases are a combination of phase components selected from the group consisting of poly(vinyl alcohol)-poly(2-ethyl-2-oxazoline), poly(vinyl alcohol)-dextran sulfate, and poly(2-ethyl-2-oxazoline)-dextran sulfate. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(vinyl alcohol), poly(2-ethyl-2-oxazoline), and chondroitin sulfate A. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(vinyl alcohol), poly(2-ethyl-2-oxazoline), and chondroitin sulfate A, respectively. In some embodiments, the multi-phase system is a two-phase system and the phase components in the two phases are a combination of phase components selected from the group consisting of poly(vinyl alcohol)-poly(2-ethyl-2-oxazoline), poly(vinyl alcohol)-chondroitin sulfate A, and poly(2-ethyl-2-oxazoline)-chondroitin sulfate A. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(vinyl alcohol), poly(ethylene glycol), and dextran sulfate, with the proviso that the multi-phase system does not include:

an aqueous two-phase system wherein the phase components in the two phases are a combination selected from the group consisting of poly(vinyl alcohol)-poly(ethylene glycol) and poly(ethylene glycol)-dextran sulfate. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(vinyl alcohol), poly(ethylene glycol), and dextran sulfate, respectively. In some embodiments, the multi-phase system is a two-phase system and the phase components in the two phases are a combination of poly(vinyl alcohol)-dextran sulfate. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(2-ethyl-2-oxazoline), dextran, and Triton, with the proviso that the multi-phase system does not include:

an aqueous two-phase system wherein the phase components in the two phases are a combination of dextran-Triton. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(2-ethyl-2-oxazoline), dextran, and Triton, respectively. In some embodiments, the multi-phase system is a two-phase system and the phase components in the two phases are a combination of phase components selected from the group consisting of poly(2-ethyl-2-oxazoline)-dextran and poly(2-ethyl-2-oxazoline)-Triton. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(2-ethyl-2-oxazoline), Ficoll, and Brij. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(2-ethyl-2-oxazoline), Ficoll, and Brij, respectively. In some embodiments, the multi-phase system is a two-phase system and the phase components in the two phases are a combination of phase components selected from the group consisting of poly(2-ethyl-2-oxazoline)-Ficoll, poly(2-ethyl-2-oxazoline)-Brij, and Ficoll-Brij. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of poly(2-ethyl-2-oxazoline), Ficoll, and Triton. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are poly(2-ethyl-2-oxazoline), Ficoll, and Triton, respectively. In some embodiments, the multi-phase system is a two-phase system and the phase components in the two phases are a combination of phase components selected from the group consisting of poly(2-ethyl-2-oxazoline)-Ficoll, poly(2-ethyl-2-oxazoline)-Triton, and Ficoll-Triton. In some specific embodiments, each phase of the MPS is aqueous phase.

In yet another aspect, a multi-phase system comprising three phases is described, wherein each phase comprises a phase component, wherein the phase component is selected from the group consisting of a polymer, a surfactant, and a combination thereof;

each of the phases has a different density and the phases, taken together, represent a density gradient;

the phases are phase-separated from each other; and the phase components in the three phases are poly(ethylene glycol) or a co- or ter-polymer thereof, polyvinylpyrrolidone or a co- or ter-polymer thereof, and dextran, respectively. In some embodiments, the MPS comprises a mixture of aqueous and organic phases. In some embodiments, the MPS comprises all aqueous phases. In some embodiments, the MPS comprises all organic phases.

In some embodiments, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of dextran, Ficoll, and Triton, with the proviso that the multi-phase system does not include:

an aqueous two-phase system wherein the phase components in the two phases are a combination selected from the group consisting of dextran-Ficoll and dextran-Triton.

In some embodiments, the multi-phase system is a three-phase system and the phase components in the three phases are dextran, Ficoll, and Triton, respectively. In some embodiments, the multi-phase system is a two-phase system and the phase components in the two phases are a combination of Ficoll-Triton. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of dextran, polyvinylpyrrolidone, and poly(2-acrylamido-2-methyl-1-propanesulfonic acid), with the proviso that the multi-phase system does not include:

an aqueous two-phase system wherein the phase components in the two phases are a combination of dextran-polyvinylpyrrolidone. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are dextran, polyvinylpyrrolidone, and poly(2-acrylamido-2-methyl-1-propanesulfonic acid), respectively. In some embodiments, the multi-phase system is a two-phase system and the phase components in the two phases are a combination of phase components selected from the group consisting of poly(2-acrylamido-2-methyl-1-propanesulfonic acid-dextran and poly(2-acrylamido-2-methyl-1-propanesulfonic acid-polyvinylpyrrolidone. In some specific embodiments, each phase of the MPS is aqueous phase.

In yet another aspect, a multi-phase system comprising two or more phases is described, wherein each phase comprises a phase component, wherein the phase component is selected from the group consisting of a polymer, a surfactant, and a combination thereof;

each of the two or more phases has a different density and the phases, taken together, represent a density gradient; and the phases are phase-separated from each other, wherein the phase components are selected from the groups consisting of dextran, hydroxyethyl cellulose, and Triton, with the proviso that the multi-phase system does not include:

an aqueous two-phase system wherein the phase components in the two phases are a combination of phase components selected from the group consisting of dextran-Triton and hydroxyethyl cellulose-Triton. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are dextran, hydroxyethyl cellulose, and Triton, respectively. In some embodiments, the multi-phase system is a two-phase system and the phase components in the two phases are a combination of hydroxyethyl cellulose-dextran. In some specific embodiments, each phase of the MPS is aqueous phase.

In yet another aspect, a multi-phase system comprising two or more phases is described, wherein
each phase comprises a phase component, wherein the phase component is selected from the group consisting of a polymer, a surfactant, and a combination thereof;
each of the two or more phases has a different density and the phases, taken together, represent a density gradient; and
the phases are phase-separated from each other, wherein the phase components are selected from the groups consisting of Ficoll, hydroxyethyl cellulose, and Triton, with the proviso that the multi-phase system does not include:
an aqueous two-phase system wherein the phase components in the two phases are a combination of hydroxyethyl cellulose-Triton. In some embodiments, the MPS comprises a mixture of aqueous and organic phases. In some embodiments, the MPS comprises all aqueous phases. In some embodiments, the MPS comprises all organic phases.

In some embodiments, the multi-phase system is a three-phase system and the phase components in the three phases are Ficoll, hydroxyethyl cellulose, and Triton, respectively. In some embodiments, the multi-phase system is a two-phase system and the phase components in the two phases are a combination of phase components selected from the group consisting of hydroxyethyl cellulose-Ficoll and Ficoll-Triton. In some specific embodiments, each phase of the MPS is aqueous phase.

In yet another aspect, a two-phase system comprising a first and second phases is described, wherein
the first phase comprises poly(diallyldimethyl ammonium chloride);
the second phase comprises a phase component selected from the group consisting of poly(methacrylic acid), poly(acrylic acid), poly(vinyl alcohol), poly(2-ethyl-2-oxazoline), and poly(ethylene glycol);
each of the two or more phases has a different density and the phases, taken together, represent a density gradient; and
the phases are phase-separated from each other.

In yet another aspect, a two-phase system comprising a first and second phases is described, wherein
the first phase comprises chondroitin sulfate A;
the second phase comprises a phase component selected from the group consisting of poly(methacrylic acid), poly(vinyl alcohol), and poly(2-ethyl-2-oxazoline);
each of the two or more phases has a different density and the phases, taken together, represent a density gradient, and
the phases are phase-separated from each other.

In yet another aspect, a two-phase system comprising a first and second phases is described, wherein
the first phase comprises poly(propylene glycol);
the second phase comprises a phase component selected from the group consisting of poly(methacrylic acid) and polyacrylamide;
each of the two or more phases has a different density and the phases, taken together, represent a density gradient, and
the phases are phase-separated from each other.

In yet another aspect, a two-phase system comprising a first and second phases is described, wherein
the first phase comprises poly(styrene sulfonic acid);
the second phase comprises a phase component selected from the group consisting of poly(2-ethyl-2-oxazoline) and dextran sulfate;
each of the two or more phases has a different density and the phases, taken together, represent a density gradient, and
the phases are phase-separated from each other.

In yet another aspect, a two-phase system comprising a first and second phases is described, wherein
the first phase comprises polyallylamine;
the second phase comprises a phase component selected from the group consisting of Tween, Triton, dextran sulfate, and Brij;
each of the two or more phases has a different density and the phases, taken together, represent a density gradient, and
the phases are phase-separated from each other.

In yet another aspect, a two-phase system comprising a first and second phases is described, wherein
each of the first and second phases comprises a phase component;
the phase components in the two phases are a combination of phase components selected from the group consisting of diethylaminoethyl-dextran-poly(acrylic acid), carboxy-polyacrylamide-poly(vinyl alcohol), methyl cellulose-Ficoll, Zonyl-dextran, Triton X-100-poly(acrylic acid), and sodium dodecyl sulfate-poly(acrylic acid),
each of the two or more phases has a different density and the phases, taken together, represent a density gradient, and
the phases are phase-separated from each other.

In yet another aspect, a two-phase system comprising a first and second phases is described, wherein
the first phase comprises alginic acid;
the second phase comprises a phase component selected from the group consisting of poly(acrylic acid), and poly(propylene glycol);
each of the two or more phases has a different density and the phases, taken together, represent a density gradient, and
the phases are phase-separated from each other.

In yet another aspect, a two-phase system comprising a first and second phases is described, wherein
the first phase comprises (hydroxypropyl)methyl cellulose;
the second phase comprises a phase component selected from the group consisting of poly(diallyldimethyl ammonium chloride), and poly(propylene glycol);
each of the two or more phases has a different density and the phases, taken together, represent a density gradient, and
the phases are phase-separated from each other.

In yet another aspect, a two-phase system comprising a first and second phases, wherein
the first phase comprises nonylphenol polyoxyethylene;
the second phase comprises a phase component selected from the group consisting of poly(methacrylic acid), and dextran;
each of the two or more phases has a different density and the phases, taken together, represent a density gradient, and
the phases are phase-separated from each other.

In yet another aspect, a two-phase system comprising a first and second phases is described, wherein the first phase comprises sodium cholate;

the second phase comprises a phase component selected from the group consisting of poly(methacrylic acid), and dextran sulfate;

each of the two or more phases has a different density and the phases, taken together, represent a density gradient, and the phases are phase-separated from each other.

In some embodiments, the MPS is organic. Each phase of the organic MPS comprises an organic solvent and a phase component as defined herein. The organic multi-phase system comprising at least a first and second non-aqueous phases, wherein the first phase is non-aqueous and comprise a first organic solvent and a first phase component;

the second phase is non-aqueous and comprises a second organic solvent and a second phase component;

the first and second phases are in contact and phase-separated from each other;

the phase component is selected from the group consisting of a polymer, a surfactant, and a combination thereof; and each of the first and second phases has a different density and the phases, taken together, represent a density gradient. Non-limiting examples of the first and second solvents include liquid polymer, dichloromethane, THF, ethanol, supercritical $CO_2$, fuel, and lubricant. The first and the second solvents can be the same or different. In some specific embodiments, the first and second solvents are each dichloromethane. In some embodiments, the organic MPS comprises phase components selected from the group consisting of poly(bisphenol A carbonate), polydimethylsiloxane, polystyrene, poly(4-vinylpyridine), poly(2-ethyl-2-oxazoline), polycaprolactone. In some embodiments, the multi-phase system is a six-phase system and the phase components in the six phases are poly(bisphenol A carbonate), polydimethylsiloxane, polystyrene, poly(4-vinylpyridine), poly(2-ethyl-2-oxazoline), polycaprolactone, respectively. In some embodiments, the multi-phase system is a five-phase system and the phase components in the five phases are a combination of phase components selected from the group consisting of poly(bisphenol A carbonate)-polydimethylsiloxane-polystyrene-poly(4-vinylpyridine)-poly(2-ethyl-2-oxazoline), poly(bisphenol A carbonate)-polydimethylsiloxane-polystyrene-polycaprolactone, poly(bisphenol A carbonate)-polydimethylsiloxane-polystyrene-poly(2-ethyl-2-oxazoline)-poly caprolactone, poly(bisphenol A carbonate)-polydimethylsiloxane-poly(4-vinylpyridine)-poly(2-ethyl-2-oxazoline)-polycaprolactone, poly(bisphenol A carbonate)-polystyrene-poly(4-vinylpyridine)-poly(2-ethyl-2-oxazoline)-polycaprolactone, and polydimethylsiloxane-polystyrene-poly(4-vinylpyridine)-poly(2-ethyl-2-oxazoline)-polycaprolactone. In some embodiments, the multi-phase system is a four-phase system and the phase components in the four phases are a combination of phase components selected from the group consisting of poly(bisphenol A carbonate)-polydimethylsiloxane-polystyrene-poly(4-vinylpyridine), poly(bisphenol A carbonate)-polydimethylsiloxane-polystyrene-poly(2-ethyl-2-oxazoline), poly(bisphenol A carbonate)-polydimethylsiloxane-polystyrene-polycaprolactone, poly(bisphenol A carbonate)-polydimethylsiloxane-poly(4-vinylpyridine)-poly(2-ethyl-2-oxazoline), poly(bisphenol A carbonate)-polydimethylsiloxane-poly(4-vinylpyridine)polycaprolactone, poly(bisphenol A carbonate)-polydimethylsiloxane-poly(2-ethyl-2-oxazoline)-polycaprolactone, poly(bisphenol A carbonate)-polystyrene-poly(4-vinylpyridine)-poly(2-ethyl-2-oxazoline), poly(bisphenol A carbonate)-polystyrene-poly(4-vinylpyridine)-polycaprolactone, poly(bisphenol A carbonate)-polystyrene-poly(2-ethyl-2-oxazoline)-polycaprolactone, poly(bisphenol A carbonate)-poly(4-vinylpyridine)-poly(2-ethyl-2-oxazoline)-polycaprolactone, polydimethylsiloxane-polystyrene-poly(4-vinylpyridine)-poly(2-ethyl-2-oxazoline), polydimethylsiloxane-polystyrene-poly(4-vinylpyridine)-polycaprolactone, polydimethylsiloxane-polystyrene-poly(2-ethyl-2-oxazoline)-polycaprolactone, polydimethylsiloxane-poly(4-vinylpyridine)-poly(2-ethyl-2-oxazoline)-polycaprolactone, and polystyrene-poly(4-vinylpyridine)-poly(2-ethyl-2-oxazoline)-polycaprolactone. In some embodiments, the multi-phase system is a three-phase system and the phase components in the three phases are a combination of phase components selected from the group consisting of poly(bisphenol A carbonate)-polydimethylsiloxane-polystyrene, poly(bisphenol A carbonate)-polydimethylsiloxane-poly(4-vinylpyridine), poly(bisphenol A carbonate)-polydimethylsiloxane-poly(2-ethyl-2-oxazoline, poly(bisphenol A carbonate)-polydimethylsiloxane-polycaprolactone, poly(bisphenol A carbonate)-polystyrene-poly(4-vinylpyridine), poly(bisphenol A carbonate)-polystyrene-poly(2-ethyl-2-oxazoline), poly(bisphenol A carbonate)-polystyrene-polycaprolactone, poly(bisphenol A carbonate)-poly(4-vinylpyridine)-poly(2-ethyl-2-oxazoline), poly(bisphenol A carbonate)-poly(4-vinylpyridine)-polycaprolactone, poly(bisphenol A carbonate)-poly(2-ethyl-2-oxazoline)-polycaprolactone, polydimethylsiloxane-polystyrene-poly(4-vinylpyridine), polydimethylsiloxane-polystyrene-poly(2-ethyl-2-oxazoline), polydimethylsiloxane-polystyrene-polycaprolactone, polydimethylsiloxane-poly(4-vinylpyridine)-poly(2-ethyl-2-oxazoline), polydimethylsiloxane-poly(4-vinylpyridine)-polycaprolactone, polydimethylsiloxane-poly(2-ethyl-2-oxazoline)-polycaprolactone, polystyrene-poly(4-vinylpyridine)-poly(2-ethyl-2-oxazoline), polystyrene-poly(4-vinylpyridine)-polycaprolactone, polystyrene-poly(2-ethyl-2-oxazoline)-polycaprolactone, and poly(4-vinylpyridine)-poly(2-ethyl-2-oxazoline)-polycaprolactone. In some embodiments, the multi-phase system is a two-phase system and the phase components in the two phases are a combination of phase components selected from the group consisting of poly(bisphenol A carbonate)-polydimethylsiloxane, poly(bisphenol A carbonate)-polystyrene, poly(bisphenol A carbonate)-poly(4-vinylpyridine), poly(bisphenol A carbonate)-poly(2-ethyl-2-oxazoline), poly(bisphenol A carbonate)-polycaprolactone, polydimethylsiloxane-polystyrene,
polydimethylsiloxane-poly(4-vinylpyridine),
polydimethylsiloxane-poly(2-ethyl-2-oxazoline),
polydimethylsiloxane-polycaprolactone,
polystyrene-poly(4-vinylpyridine),
polystyrene-poly(2-ethyl-2-oxazoline),
polystyrene-polycaprolactone,
poly(4-vinylpyridine)-poly(2-ethyl-2-oxazoline),
poly(4-vinylpyridine)-polycaprolactone, and
poly(2-ethyl-2-oxazoline)-polycaprolactone.

In some embodiments, the organic multi-phase system is a two-phase system, wherein the first phase comprises poly(bisphenol A carbonate), the second phase comprises a phase component selected from the group consisting of polysulfone, polyvinylpyrrolidone, poly(methyl methacrylate-co-methacrylic acid), poly(methyl methacrylate), Tween, poly(tetrahydrofuran), poly(propylene glycol), poly(ethylene glycol), and poly(vinyl acetate). In some embodiments, the organic multi-phase system is a two-phase system, wherein the first phase comprises polysulfone, the second phase comprises a phase component selected from the group consisting of polydimethylsiloxane, polystyrene, poly(4-vinylpyridine), polyvinylpyrrolidone, poly(2-ethyl-2-oxazoline), polyethyleneimine, poly(methyl methacrylate-co-methacrylic acid), poly(methyl methacrylate), poly(tetrahydrofuran), poly(propylene glycol), poly(ethylene glycol), poly(vinyl acetate), and polycaprolactone. In some embodiments, the organic multi-phase system is a two-phase system, wherein the first phase comprises polydimethylsiloxane, the second phase comprises a phase component selected from the group consisting of polyvinylpyrrolidone, polyethyleneimine, poly(methyl methacrylate-co-methacrylic acid), poly(methyl methacrylate), Tween, poly(tetrahydrofuran), poly(ethylene glycol), and poly(vinyl acetate).

In some embodiments, the organic multi-phase system is a two-phase system, wherein the first phase comprises polystyrene, the second phase comprises a phase component selected from the group consisting of polyvinylpyrrolidone, polyethyleneimine, poly(methyl methacrylate-co-methacrylic acid), poly(methyl methacrylate), poly(tetrahydrofuran), Tween, poly(ethylene glycol), and poly(vinyl acetate). In some embodiments, the organic multi-phase system is a two-phase system, wherein the first phase comprises poly(4-vinylpyridine), the second phase comprises a phase component selected from the group consisting of polyethyleneimine, poly(methyl methacrylate-co-methacrylic acid), poly(methyl methacrylate), poly(tetrahydrofuran), Tween, poly(propylene glycol), poly(ethylene glycol), and poly(vinyl acetate).

In some embodiments, the organic multi-phase system is a two-phase system, wherein the first phase comprises polyvinylpyrrolidone, the second phase comprises a phase component selected from the group consisting of poly(tetrahydrofuran), poly(propylene glycol), poly(ethylene glycol), and poly(vinyl acetate). In some embodiments, the organic multi-phase system is a two-phase system, wherein the first phase comprises poly(2-ethyl-2-oxazoline), the second phase comprises a phase component selected from the group consisting of poly(tetrahydrofuran), poly(propylene glycol), poly(ethylene glycol), and poly(vinyl acetate). In some embodiments, the organic multi-phase system is a two-phase system, wherein the first phase comprises polyethyleneimine, the second phase comprises a phase component selected from the group consisting of poly(ethylene glycol), polycaprolactone, and poly(vinyl acetate). In some embodiments, the organic multi-phase system is a two-phase system, wherein the first phase comprises polycaprolactone, the second phase comprises a phase component selected from the group consisting of poly(methyl methacrylate-co-methacrylic acid) and poly(methyl methacrylate).

In some embodiments, the MPS comprises two or more liquid polymer phases (solvent free phases; see Experimental Section for the acronym of the polymers). In some embodiments, the liquid polymer MPS is a two phase liquid polymer MPS selected from the group consisting of: PPG-PEG; PPG-PL; PPG-PDMS; PPG-PBD; PEG-PL; PEG-PDMS; PEG-PEVE; PEG-PBD; PL-PDMS; PL-PBD; PDMS-PEVE; PDMS-PBD; and PEVE-PBD.

In some embodiments, the liquid polymer MPS is a three phase liquid polymer MPS selected from the group consisting of: PPG-PEG-PL; PPG-PDMS-PBD; PPG-PEG-PBD; PEG-PEVE-PBD; PEG-PEVE-PDMS; PPG-PEG-PDMS; PEG-PL-PDMS; PEG-PL-PBD; PL-PDMS-PBD; and PDMS-PEVE-PBD.

In some embodiments, the liquid polymer MPS is a four phase liquid polymer MPS selected from the group consisting of: PPG-PEG-PL-PDMS; PPG-PEG-PL-PBD; PPG-PEG-PDMS-PBD; PPG-PL-PDMS-PBD; and PEG-PL-PDMS-PBD.

In some embodiments, the liquid polymer MPS is a five phase liquid polymer MPS having the composition of PPG-PEG-PL-PDMS-PBD.

In some embodiments, the MPS has is a two-phase system wherein the combination of reagents of the phases is selected from the group consisting of PVPNO-PA, PVPNO-PMAA, PVPNO-PAA, PVPNO-PVA, PVPNO-PEOZ, PVPNO-PEG, PVPNO-HEC, PVPNO-Dextran, PVPNO-Ficoll, PVPNO-PEI, PVPNO-Tween, and PVPNO-PVP (see Experimental Section for the acronym of the polymers).

In some embodiments, the MPS has is a three-phase system wherein the combination of reagents of the phases is selected from the group consisting of PEOZ-PEG-PVPNO, PEOZ-PEI-PVPNO, PEOZ-PA-PVPNO, PEOZ-PMAA-PVPNO, PEG-PEI-PVPNO, PEG-PMAA-PVPNO, PEG-PA-PVPNO, PEI-PA-PVPNO, PEI-PMAA-PVPNO, PA-PMAA-PVPNO, PEOZ-PEG-PVPNO, PEOZ-TWEEN-PVPNO, PEOZ-PA-PVPNO, PEOZ-PMAA-PVPNO, PEG-TWEEN-PVPNO, TWEEN-PA-PVPNO, TWEEN-PMAA-PVPNO, PA-PMAA-PVPNO, PEG-PA-PVPNO, and PEG-PMAA-PVPNO (see Experimental Section for the acronym of the polymers).

In some embodiments, the MPS has is a four-phase system wherein the combination of reagents of the phases is selected from the group consisting of PEOZ-PEG-PEI-PVPNO, PEOZ-PEG-PA-PVPNO, PEOZ-PEI-PA-PVPNO, PEOZ-PEI-PMAA-PVPNO, PEOZ-PA-PMAA-PVPNO, PEG-PEI-PA-PVPNO, PEG-PEI-PMAA-PVPNO, PEG-PA-PMAA-PVPNO, PEI-PA-PMAA-PVPNO, PEOZ-PEG-PMAA-PVPNO, PEOZ-PEG-PA-PVPNO, PEOZ-PEG-TWEEN-PVPNO, PEOZ-TWEEN-PA-PVPNO, PEOZ-TWEEN-PMAA-PVPNO, PEOZ-PA-PMAA-PVPNO, PEG-TWEEN-PA-PVPNO, PEG-TWEEN-PMAA-PVPNO, PEG-PA-PMAA-PVPNO, and TWEEN-PA-PMAA-PVPNO (see Experimental Section for the acronym of the polymers).

In some embodiments, the MPS has is a five-phase system wherein the combination of reagents of the phases is selected from the group consisting of PEG-PEI-PA-PMAA-PVPNO, PEOZ-PEI-PA-PMAA-PVPNO, PEOZ-PEG-PA-PMAA-PVPNO, PEOZ-PEG-PEI-PMAA-PVPNO, PEOZ-PEG-PEI-PA-PVPNO, PEOZ-PEG-PEI-PA-PMAA, PEG-TWEEN-PA-PMAA-PVPNO, PEOZ-TWEEN-PA-PMAA-PVPNO, PEOZ-PEG-TWEEN-PMAA-PVPNO, PEOZ- PEG-TWEEN-PA-PVPNO, and PEOZ-PEG-TWEEN-PA-PMAA (see Experimental Section for the acronym of the polymers).

In some embodiments, the MPS has is a six-phase system wherein the combination of reagents of the phases is selected from the group consisting of PEOZ-PEG-PEI-PA-PMAA-PVPNO and PEOZ-PEG-TWEEN-PA-PMAA-PVPNO (see Experimental Section for the acronym of the polymers).

In some embodiments, the MPS system has the composition selected form the compositions disclosed in Tables S2-S6.

Experimental Section

Chemicals

Allura Red, alginic acid sodium salt, Brij 35, 3-[(3-cholamidopropyl) dimethylammonio]-1-propanesulfonate (CHAPS), chondroitin sulfate A, dextran sulfate sodium salt, ethyl orange, Ficoll, (hydroxypropyl)methyl cellulose, poly (2-acrylamido-2-methyl-1-propanesulfonic acid), poly(2-ethyl-2-oxazoline), polyacrylamide, poly(diallyldimethylammonium chloride), poly(ethylene glycol), polyethyleneimine, poly(methacrylic acid sodium salt), poly (propylene glycol), polyvinylpyrrolidone, sodium cholate, Tween 20, Pluronic F68 and Zonyl were purchased from Sigma-Aldrich. Poly(acrylic acid), poly(allylamine hydrochloride), poly(styrenesulfonic acid sodium salt), poly(2-vinylpyridine-N-oxide), and poly(vinyl alcohol) were obtained from Polysciences. Dextran was purchased from Spectrum Chemical. Diethylaminoethyl-dextran hydrochloride was purchased from MP Biomedicals. Carboxy-modified polyacrylamide, hydroxyethyl cellulose, methyl cellulose were purchased from Scientific Polymer Products. DOWFAX 2A1 was purchased from Dow Chemicals. N,N-dimethyldodecylamine N-oxide was purchased from Fluka. N-octyl-β-D-glucopyranoside was purchased from Alfa Aesar. Sodium dodecyl sulfate was purchased from J. T. Baker. Triton X-100 was purchased from Calbiochem. All chemicals were used without further purification.

Experimental Designs

Binary mixtures of twenty-three polymers and eleven surfactants were investigated. Applicants then systematically examined potential three-, four-, five-, and six-solution mixtures based on the results of the binary immiscibility screen to identify systems that exhibited segregation into multiple phases. For example, poly(propylene glycol)-poly (methacrylic acid), poly(propylene glycol)-polyacrylamide, and poly(methacrylic acid)-polyacrylamide ATPS were combined to produce a poly(propylene glycol)-polyacrylamide-poly(methacrylic acid) three-phase MPS.

Stock Solutions

Applicants prepared stock solutions of polymers in Milli-Q water at high concentrations, between 1-40% (w/v) without adding salts or titrating the pH. Applicants characterized the density, refractive index, and osmolality of each stock solution using oscillating U-tube densitometry (Anton Paar DM35N), refractometry (Bausch & Lomb Abbe Refractometer), and freezing point depression osmometry (Advanced Instruments Model 3000 MicroOsmometer). The results of these characterizations are given in Table S1. The densities for stock solutions of polyacrylamide and poly(2-acrylamido-2-methyl-1-propanesulfonic acid) were determined by measuring the densities of three lower concentrations and determining the linear fit to the resulting line.

TABLE S1

Properties of the polymer stock solutions: average molecular weight (Da), concentration (% wt/vol), density (g/cm$^3$), osmolality (mOsm/kg), and refractive index; "n.d." stands for "not determined", and an asterisk (*) refers to densities that were calculated, rather than measured.

| | Polymer | avg. MW (Da) | % (wt/vol) | density (g/cm$^3$) | osmolality (mOsm/kg) | refractive index |
|---|---|---|---|---|---|---|
| 1 | poly(methacrylic acid) | 5,000 | 40 | 1.279 | n.d. | 1.4250 |
| 2 | poly(acrylic acid) | 450,000 | 10 | 1.035 | 28 | 1.3445 |
| 3 | poly(vinyl alcohol) | 3,000 | 10 | 1.022 | 84 | 1.3635 |
| 4 | poly(2-ethyl-2-oxazoline) | 200,000 | 35 | 1.059 | n.d. | 1.3865 |
| 5 | poly(ethylene glycol) | 20,000 | 40 | 1.069 | n.d. | 1.3860 |
| 6 | dextran | 500,000 | 30 | 1.101 | 286 | 1.3700 |
| 7 | Ficoll | 400,000 | 40 | 1.130 | 224 | 1.3860 |
| 8 | polyacrylamide | 10,000 | 40 | 1.149 * | n.d. | 1.4130 |
| 9 | poly(diallyldimethylammonium chloride) | 400,000 | 20 | 1.044 | 1241 | 1.3730 |
| 10 | dextran sulfate | 500,000 | 20 | 1.103 | 539 | 1.3540 |
| 11 | Chondroitin sulfate A | 25,000 | 10 | 1.044 | 325 | 1.3460 |
| 12 | polyethyleneimine | 25,000 | 30 | 1.037 | 745 | 1.3890 |
| 13 | polyvinylpyrrolidone | 55,000 | 20 | 1.038 | 782 | 1.3635 |
| 14 | poly(propylene glycol) | 425 | 40 | 1.029 | n.d. | 1.3860 |
| 15 | poly(2-acrylamido-2-methyl-1-propanesulfonic acid) | 2,000,000 | 15 | 1.042 * | 353 | 1.3520 |
| 16 | poly(styrenesulfonic acid) | 75,000 | 30 | 1.100 | n.d. | 1.3975 |
| 17 | diethylaminoethyl-dextran | 500,000 | 10 | 1.028 | 185 | 1.3460 |
| 18 | polyallylamine | 60,000 | 20 | 1.052 | 826 | 1.3710 |
| 19 | alginic acid | 240,000 | 2 | 1.010 | 50 | 1.3345 |
| 20 | (hydroxypropyl)methyl cellulose | 10,000 | 2 | 1.003 | 7 | 1.3345 |
| 21 | carboxy-polyacrylamide | 200,000 | 6 | 1.018 | 93 | 1.3410 |
| 22 | hydroxyethyl cellulose | 90,000 | 2 | 1.004 | 24 | 1.3340 |
| 23 | methyl cellulose | 86,000 | 1 | 1.001 | −6 | 1.3325 |

Example 1. Preparation of Multi-Phase Systems

Biphasic Separation

To perform the initial two-phase polymer immiscibility screens, Applicants added equal volumes (150 μL) of each polymer solution into a microcentrifuge tube, vortexed the tube for 30 seconds to thoroughly mix the solutions, and accelerated segregation into phases by centrifugation at 2,000×g for 10 minutes. In some instances, Applicants observed an acute volumetric rearrangement of a single layer of the aqueous two-phase system (ATPS). This is a well-understood phenomenon that results when the initial concentrations of the system are near the node of the tie-line of the phase diagram that characterizes the set of mixtures for a polymer/polymer system. For such ATPS, Applicants modified either the volume ratio or diluted the polymer stock solution in order to verify that phase separation occurred. From the investigation of 34 unique water-soluble polymers and surfactants, Applicants identified numerous unreported ATPS and confirmed those that have been previously described by others (Table S2).

Results and Discussion

Applicants generated a series of miscibility profiles for each reagent by assigning a 34-component vector describing the results from all two-component mixtures that include the reagent. The vector has values '0' for mixtures that resulted in homogeneous solutions (miscible, shown in light gray square), '1' for mixtures that resulted in a precipitate or a gel (incompatible, shown in black square), and '2' for mixtures that resulted in phase separation (immiscible, shown in dark gray square).

Applicants can compare the miscibility profiles of N reagents, and clusters of reagents, by analyzing the magnitudes of each vector and the distances between vectors in N-dimensional space: a small distance between vectors indicates similar miscibility profiles. Applicants ordered the reagents in our AMS matrix according to this vector analysis (FIG. 1).

Using this approach to ordering, Applicants identified several patterns based on similarities in miscibility in two-component mixtures: neutral, branched polysaccharides (numbers 3 and 4), acrylic acids (4 and 5), cationic species (10, 12, and 13), hydrophobic species incorporating ethylene oxide units (14-18), and anionic species (21, 22, 24, 26-29) are clustered by patterns of miscibility using this analysis.

Applicants observed phase separation in formerly characterized two-phase systems, but Applicants also identified numerous previously unreported ATPS. Examples of these new systems include polyvinylpyrrolidone-poly(methacrylic acid), poly(styrenesulfonic acid)-alginic acid, and poly(vinyl alcohol)-carboxy-polyacrylamide. The complete two-phase ATPS results are shown in Table S2, while the lists of three-, four-, five-, and six-phase MPS are shown in Table S4, Table S5, and Table S6, respectively.

Figure 2B:
Figure 2C:
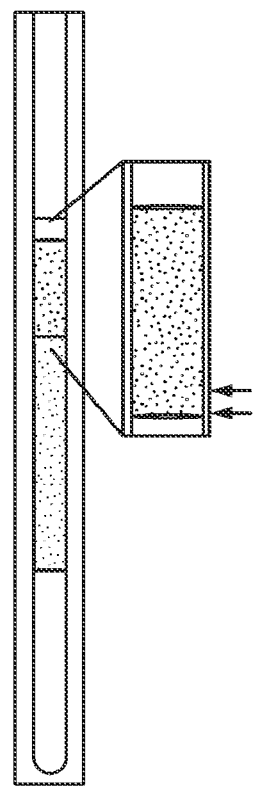

Images of multiphase polymer systems are shown in FIGS. 2(A)-2(C). FIG. 2(A) shows a three-phase system comprising poly(propylene glycol)-polyacrylamide-poly (methacrylic acid). FIG. 2(B) shows a four-phase system comprising poly(vinyl alcohol)-poly(2-ethyl-2-oxazoline)-poly(ethylene glycol)-polyacrylamide. FIG. 2(C) shows a five-phase system comprising poly(vinyl alcohol)-poly(2-ethyl-2-oxazoline)-poly(ethylene glycol)-dextran-Ficoll. Allura Red, a dye, was added to highlight the interfaces of each polymer system; the color balance and contrast of the inset image were modified to further differentiate the second and third layers of the five-phase polymer system, which are marked by arrows. The most complex AMPS from this survey were two systems composed of five layers: (i) polyethyleneimine-poly(2-ethyl-2-oxazoline)-poly(ethylene glycol)-polyacrylamide-poly(methacrylic acid) and (ii) poly (vinyl alcohol)-poly(2-ethyl-2-oxazoline)-poly(ethylene glycol)-dextran-Ficoll (FIG. 2C).

TABLE S2

List of new and previously reported aqueous MPS found by this study.

| Count | Polymers | | NEW (1) OLD (0) |
|---|---|---|---|
| 1 | poly(2-ethyl-2-oxazoline) | poly(methacrylic acid) | 1 |
| 2 | poly(2-ethyl-2-oxazoline) | poly(vinyl alcohol) | 1 |
| 3 | poly(ethylene glycol) | poly(methacrylic acid) | 1 |
| 4 | poly(ethylene glycol) | poly(acrylic acid) | 0 |
| 5 | poly(ethylene glycol) | poly(vinyl alcohol) | 0 |
| 6 | poly(ethylene glycol) | poly(2-ethyl-2-oxazoline) | 1 |
| 7 | dextran | poly(vinyl alcohol) | 0 |
| 8 | dextran | poly(2-ethyl-2-oxazoline) | 1 |
| 9 | dextran | poly(ethylene glycol) | 0 |
| 10 | Ficoll | poly(methacrylic acid) | 1 |
| 11 | Ficoll | poly(vinyl alcohol) | 1 |
| 12 | Ficoll | poly(2-ethyl-2-oxazoline) | 1 |
| 13 | Ficoll | poly(ethylene glycol) | 0 |
| 14 | Ficoll | dextran | 0 |
| 15 | polyacrylamide | poly(methacrylic acid) | 1 |
| 16 | polyacrylamide | poly(acrylic acid) | 1 |
| 17 | polyacrylamide | poly(vinyl alcohol) | 0 |
| 18 | polyacrylamide | poly(2-ethyl-2-oxazoline) | 1 |
| 19 | polyacrylamide | poly(ethylene glycol) | 1 |
| 20 | poly(diallyldimethyl ammonium chloride | poly(methacrylic acid) | 1 |
| 21 | poly(diallyldimethyl ammonium chloride | poly(acrylic acid) | 1 |
| 22 | poly(diallyldimethyl ammonium chloride | poly(vinyl alcohol) | 1 |
| 23 | poly(diallyldimethyl ammonium chloride | poly(2-ethyl-2-oxazoline) | 1 |
| 24 | poly(diallyldimethyl ammonium chloride | poly(ethylene glycol) | 1 |
| 25 | dextran sulfate | poly(vinyl alcohol) | 1 |
| 26 | dextran sulfate | poly(2-ethyl-2-oxazoline) | 1 |
| 27 | dextran sulfate | poly(ethylene glycol) | 0 |
| 28 | chondroitin sulfate A | poly(methacrylic acid) | 1 |
| 29 | chondroitin sulfate A | poly(vinyl alcohol) | 1 |
| 30 | chondroitin sulfate A | poly(2-ethyl-2-oxazoline) | 1 |
| 31 | polyethyleneimine | poly(methacrylic acid) | 1 |
| 32 | polyethyleneimine | poly(2-ethyl-2-oxazoline) | 1 |
| 33 | polyethyleneimine | poly(ethylene glycol) | 1 |

TABLE S2-continued

List of new and previously reported aqueous MPS found by this study.

| Count | Polymers | | NEW (1) OLD (0) |
|---|---|---|---|
| 34 | polyethyleneimine | Ficoll | 1 |
| 35 | polyethyleneimine | polyacrylamide | 1 |
| 36 | polyvinylpyrrolidone | poly(methacrylic acid) | 1 |
| 37 | polyvinylpyrrolidone | poly(ethylene glycol) | 0 |
| 38 | polyvinylpyrrolidone | dextran | 0 |
| 39 | poly(propylene glycol) | poly(methacrylic acid) | 1 |
| 40 | poly(propylene glycol) | dextran | 0 |
| 41 | poly(propylene glycol) | polyacrylamide | 1 |
| 42 | poly(2-acrylamido-2-methyl-1-propanesulfonic acid) | dextran | 1 |
| 43 | poly(2-acrylamido-2-methyl-1-propanesulfonic acid) | polyvinylpyrrolidone | 1 |
| 44 | poly(styrene sulfonic acid) | poly(2-ethyl-2-oxazoline) | 1 |
| 45 | poly(styrene sulfonic acid) | dextran sulfate | 1 |
| 46 | diethylaminoethyl-dextran | poly(acrylic acid) | 1 |
| 47 | polyallylamine | dextran sulfate | 1 |
| 48 | alginic acid | poly(acrylic acid) | 1 |
| 49 | alginic acid | poly(propylene glycol) | 1 |
| 50 | (hydroxypropyl)methyl cellulose | poly(diallyldimethyl ammonium chloride | 1 |
| 51 | (hydroxypropyl)methyl cellulose | poly(propylene glycol) | 1 |
| 52 | carboxy-polyacrylamide | poly(methacrylic acid) | 1 |
| 53 | carboxy-polyacrylamide | poly(vinyl alcohol) | 1 |
| 54 | carboxy-polyacrylamide | polyethyleneimine | 1 |
| 55 | hydroxyethyl cellulose | dextran | 1 |
| 56 | hydroxyethyl cellulose | Ficoll | 1 |
| 57 | methyl cellulose | Ficoll | 1 |
| 58 | Zonyl | poly(methacrylic acid) | 1 |
| 59 | Zonyl | dextran | 1 |
| 60 | Zonyl | polyacrylamide | 1 |
| 61 | Brij 35 | poly(2-ethyl-2-oxazoline) | 1 |
| 62 | Brij 35 | Ficoll | 1 |
| 63 | Brij 35 | polyallylamine | 1 |
| 64 | Tween 20 | poly(methacrylic acid) | 1 |
| 65 | Tween 20 | poly(vinyl alcohol) | 1 |
| 66 | Tween 20 | poly(2-ethyl-2-oxazoline) | 1 |
| 67 | Tween 20 | poly(ethylene glycol) | 0 |
| 68 | Tween 20 | dextran | 0 |
| 69 | Tween 20 | Ficoll | 1 |
| 70 | Tween 20 | polyacrylamide | 1 |
| 71 | Tween 20 | polyallylamine | 1 |
| 72 | Tween 20 | hydroxyethyl cellulose | 1 |
| 73 | Triton X-100 | poly(methacrylic acid) | 1 |
| 74 | Triton X-100 | poly(acrylic acid) | 1 |
| 75 | Triton X-100 | poly(2-ethyl-2-oxazoline) | 1 |
| 76 | Triton X-100 | dextran | 0 |
| 77 | Triton X-100 | Ficoll | 1 |
| 78 | Triton X-100 | polyacrylamide | 1 |
| 79 | Triton X-100 | polyallylamine | 1 |
| 80 | Triton X-100 | hydroxyethyl cellulose | 0 |
| 81 | nonylphenol polyoxyethylene (20) | poly(methacrylic acid) | 1 |
| 82 | nonylphenol polyoxyethylene (20) | dextran | 1 |
| 83 | 1-O-Octyl-B-D-glucopyranoside | poly(methacrylic acid) | 1 |
| 84 | 1-O-Octyl-B-D-glucopyranoside | poly(2-ethyl-2-oxazoline) | 1 |
| 85 | 1-O-Octyl-B-D-glucopyranoside | poly(ethylene glycol) | 0 |
| 86 | 1-O-Octyl-B-D-glucopyranoside | polyethyleneimine | 1 |
| 87 | Pluronic F68 | poly(methacrylic acid) | 1 |
| 88 | Pluronic F68 | poly(vinyl alcohol) | 1 |
| 89 | Pluronic F68 | poly(2-ethyl-2-oxazoline) | 1 |
| 90 | Pluronic F68 | dextran | 1 |
| 91 | Pluronic F68 | Ficoll | 1 |
| 92 | Pluronic F68 | polyacrylamide | 1 |
| 93 | Pluronic F68 | polyethyleneimine | 1 |
| 94 | sodium dodecyl sulfate | poly(acrylic acid) | 1 |
| 95 | sodium cholate | poly(methacrylic acid) | 1 |
| 96 | sodium cholate | dextran sulfate | 1 |
| 97 | N,N-dimethyldodecylamine N-oxide | poly(methacrylic acid) | 1 |
| 98 | N,N-dimethyldodecylamine N-oxide | polyacrylamide | 1 |
| 99 | CHAPS | poly(methacrylic acid) | 1 |
| 100 | CHAPS | poly(2-ethyl-2-oxazoline) | 1 |
| 101 | CHAPS | poly(ethylene glycol) | 1 |
| 102 | CHAPS | dextran | 1 |
| 103 | CHAPS | Ficoll | 1 |
| 104 | CHAPS | polyacrylamide | 1 |
| 105 | CHAPS | polyethyleneimine | 1 |
| 106 | CHAPS | Pluronic F68 | 1 |
| 107 | PVPNO | PA | 1 |
| 108 | PVPNO | PMAA | 1 |

TABLE S2-continued

List of new and previously reported aqueous MPS found by this study.

| Count | Polymers | | NEW (1) OLD (0) |
|---|---|---|---|
| 111 | PVPNO | PEOZ | 1 |
| 112 | PVPNO | PEG | 1 |
| 116 | PVPNO | PEI | 1 |
| 117 | PVPNO | Tween | 1 |

Multiphase Separation

Applicants used an identical approach to generate and optimize aqueous multiphase polymer systems (AMPS) by combining three, four, or five polymer solutions into a single microcentrifuge tube, vortexing to mix, and accelerating layer segregation by centrifugation. Applicants report the four-phase and five-phase MPS found in this study in Tables S4 and S5, respectively.

As shown in Table S4 and S5, preliminary results suggest that there are several systems which did not result in phase separation, yet are involved in a verified four- or five-phase system. However, if a combination of multiple polymer aqueous phases results in a phase-separated aqueous polymer system, any sub-combination of the multiple polymer aqueous phases will also result in a phase-separated aqueous polymer system. Accordingly, the systems that Applicants were unable to produce as shown in Table S4 and S5 are in fact producible using routine optimization.

TABLE S3

List of identified three-phase systems: "0" refers to a MPS that Applicant did not produce; "1" refers to a MPS produced.

| Count | Polymers and Surfactants as phase components | | | |
|---|---|---|---|---|
| 1 | poly(methacrylic acid) | poly(2-ethyl-2-oxazoline) | poly(ethylene glycol) | 1 |
| 2 | poly(methacrylic acid) | poly(2-ethyl-2-oxazoline) | Ficoll | 1 |
| 3 | poly(methacrylic acid) | poly(2-ethyl-2-oxazoline) | polyacrylamide | 1 |
| 4 | poly(methacrylic acid) | poly(2-ethyl-2-oxazoline) | poly(diallyldimethyl ammonium chloride | 0 |
| 5 | poly(methacrylic acid) | poly(2-ethyl-2-oxazoline) | chondroitin sulfate A | 1 |
| 6 | poly(methacrylic acid) | poly(2-ethyl-2-oxazoline) | polyethyleneimine | 1 |
| 7 | poly(methacrylic acid) | poly(2-ethyl-2-oxazoline) | Tween 20 | 1 |
| 8 | poly(methacrylic acid) | poly(2-ethyl-2-oxazoline) | Triton X-100 | 0 |
| 9 | poly(methacrylic acid) | poly(2-ethyl-2-oxazoline) | 1-O-Octyl-B-D-glucopyranoside | 1 |
| 10 | poly(methacrylic acid) | poly(2-ethyl-2-oxazoline) | Pluronic F68 | 1 |
| 11 | poly(methacrylic acid) | poly(2-ethyl-2-oxazoline) | CHAPS | 1 |
| 12 | poly(methacrylic acid) | poly(ethylene glycol) | Ficoll | 1 |
| 13 | poly(methacrylic acid) | poly(ethylene glycol) | polyacrylamide | 1 |
| 14 | poly(methacrylic acid) | poly(ethylene glycol) | poly(diallyldimethyl ammonium chloride | 0 |
| 15 | poly(methacrylic acid) | poly(ethylene glycol) | polyethyleneimine | 1 |
| 16 | poly(methacrylic acid) | poly(ethylene glycol) | polyvinylpyrrolidone | 1 |
| 17 | poly(methacrylic acid) | poly(ethylene glycol) | Tween 20 | 1 |
| 18 | poly(methacrylic acid) | poly(ethylene glycol) | 1-O-Octyl-B-D-glucopyranoside | 1 |
| 19 | poly(methacrylic acid) | poly(ethylene glycol) | CHAPS | 1 |
| 20 | poly(methacrylic acid) | Ficoll | polyethyleneimine | 1 |
| 21 | poly(methacrylic acid) | Ficoll | Tween 20 | 1 |
| 22 | poly(methacrylic acid) | Ficoll | Triton X-100 | 1 |
| 23 | poly(methacrylic acid) | Ficoll | Pluronic F68 | 1 |
| 24 | poly(methacrylic acid) | Ficoll | CHAPS | 1 |
| 25 | poly(methacrylic acid) | polyacrylamide | polyethyleneimine | 1 |
| 26 | poly(methacrylic acid) | polyacrylamide | poly(propylene glycol) | 1 |
| 27 | poly(methacrylic acid) | polyacrylamide | Zonyl | 1 |
| 28 | poly(methacrylic acid) | polyacrylamide | Tween 20 | 1 |
| 29 | poly(methacrylic acid) | polyacrylamide | Triton X-100 | 1 |
| 30 | poly(methacrylic acid) | polyacrylamide | Pluronic F68 | 1 |
| 31 | poly(methacrylic acid) | polyacrylamide | N,N-dimethyldodecylamine N-oxide | 1 |
| 32 | poly(methacrylic acid) | polyacrylamide | CHAPS | 1 |
| 33 | poly(methacrylic acid) | polyethyleneimine | carboxy-polyacrylamide | 1 |
| 34 | poly(methacrylic acid) | polyethyleneimine | 1-O-Octyl-B-D-glucopyranoside | 1 |
| 35 | poly(methacrylic acid) | polyethyleneimine | Pluronic F68 | 1 |
| 36 | poly(methacrylic acid) | polyethyleneimine | CHAPS | 1 |
| 37 | poly(methacrylic acid) | Pluronic F68 | CHAPS | 1 |
| 38 | poly(acrylic acid) | poly(ethylene glycol) | polyacrylamide | 1 |

TABLE S3-continued

List of identified three-phase systems: "0" refers to a MPS that Applicant did not produce; "1" refers to a MPS produced.

| Count | Polymers and Surfactants as phase components | | | |
|---|---|---|---|---|
| 39 | poly(acrylic acid) | poly(ethylene glycol) | poly(diallyldimethyl ammonium chloride) | 0 |
| 40 | poly(acrylic acid) | polyacrylamide | Triton X-100 | 0 |
| 41 | poly(vinyl alcohol) | poly(2-ethyl-2-oxazoline) | poly(ethylene glycol) | 1 |
| 42 | poly(vinyl alcohol) | poly(2-ethyl-2-oxazoline) | dextran | 1 |
| 43 | poly(vinyl alcohol) | poly(2-ethyl-2-oxazoline) | Ficoll | 1 |
| 44 | poly(vinyl alcohol) | poly(2-ethyl-2-oxazoline) | polyacrylamide | 1 |
| 45 | poly(vinyl alcohol) | poly(2-ethyl-2-oxazoline) | poly(diallyldimethyl ammonium chloride) | 0 |
| 46 | poly(vinyl alcohol) | poly(2-ethyl-2-oxazoline) | dextran sulfate | 1 |
| 47 | poly(vinyl alcohol) | poly(2-ethyl-2-oxazoline) | chondroitin sulfate A | 1 |
| 48 | poly(vinyl alcohol) | poly(2-ethyl-2-oxazoline) | Tween 20 | 1 |
| 49 | poly(vinyl alcohol) | poly(2-ethyl-2-oxazoline) | Pluronic F68 | 1 |
| 50 | poly(vinyl alcohol) | poly(ethylene glycol) | dextran | 1 |
| 51 | poly(vinyl alcohol) | poly(ethylene glycol) | Ficoll | 1 |
| 52 | poly(vinyl alcohol) | poly(ethylene glycol) | polyacrylamide | 1 |
| 53 | poly(vinyl alcohol) | poly(ethylene glycol) | poly(diallyldimethyl ammonium chloride) | 0 |
| 54 | poly(vinyl alcohol) | poly(ethylene glycol) | dextran sulfate | 1 |
| 55 | poly(vinyl alcohol) | poly(ethylene glycol) | Tween 20 | 1 |
| 56 | poly(vinyl alcohol) | dextran | Ficoll | 1 |
| 57 | poly(vinyl alcohol) | dextran | Tween 20 | 1 |
| 58 | poly(vinyl alcohol) | dextran | Pluronic F68 | 1 |
| 59 | poly(vinyl alcohol) | Ficoll | Tween 20 | 1 |
| 60 | poly(vinyl alcohol) | Ficoll | Pluronic F68 | 1 |
| 61 | poly(vinyl alcohol) | polyacrylamide | Tween 20 | 1 |
| 62 | poly(vinyl alcohol) | polyacrylamide | Pluronic F68 | 1 |
| 63 | poly(2-ethyl-2-oxazoline) | poly(ethylene glycol) | dextran | 1 |
| 64 | poly(2-ethyl-2-oxazoline) | poly(ethylene glycol) | Ficoll | 1 |
| 65 | poly(2-ethyl-2-oxazoline) | poly(ethylene glycol) | polyacrylamide | 1 |
| 66 | poly(2-ethyl-2-oxazoline) | poly(ethylene glycol) | poly(diallyldimethyl ammonium chloride) | 0 |
| 67 | poly(2-ethyl-2-oxazoline) | poly(ethylene glycol) | dextran sulfate | 0 |
| 68 | poly(2-ethyl-2-oxazoline) | poly(ethylene glycol) | polyethyleneimine | 1 |
| 69 | poly(2-ethyl-2-oxazoline) | poly(ethylene glycol) | Tween 20 | 1 |
| 70 | poly(2-ethyl-2-oxazoline) | poly(ethylene glycol) | 1-O-Octyl-B-D-glucopyranoside | 1 |
| 71 | poly(2-ethyl-2-oxazoline) | poly(ethylene glycol) | CHAPS | 1 |
| 72 | poly(2-ethyl-2-oxazoline) | dextran | Ficoll | 1 |
| 73 | poly(2-ethyl-2-oxazoline) | dextran | Tween 20 | 1 |
| 74 | poly(2-ethyl-2-oxazoline) | dextran | Triton X-100 | 1 |
| 75 | poly(2-ethyl-2-oxazoline) | dextran | Pluronic F68 | 1 |
| 76 | poly(2-ethyl-2-oxazoline) | dextran | CHAPS | 1 |
| 77 | poly(2-ethyl-2-oxazoline) | Ficoll | polyethyleneimine | 1 |
| 78 | poly(2-ethyl-2-oxazoline) | Ficoll | Brij 35 | 1 |
| 79 | poly(2-ethyl-2-oxazoline) | Ficoll | Tween 20 | 1 |
| 80 | poly(2-ethyl-2-oxazoline) | Ficoll | Triton X-100 | 1 |
| 81 | poly(2-ethyl-2-oxazoline) | Ficoll | Pluronic F68 | 1 |
| 82 | poly(2-ethyl-2-oxazoline) | Ficoll | CHAPS | 1 |
| 83 | poly(2-ethyl-2-oxazoline) | polyacrylamide | polyethyleneimine | 1 |
| 84 | poly(2-ethyl-2-oxazoline) | polyacrylamide | Tween 20 | 1 |
| 85 | poly(2-ethyl-2-oxazoline) | polyacrylamide | Triton X-100 | 1 |
| 86 | poly(2-ethyl-2-oxazoline) | polyacrylamide | Pluronic F68 | 1 |
| 87 | poly(2-ethyl-2-oxazoline) | polyacrylamide | CHAPS | 1 |
| 88 | poly(2-ethyl-2-oxazoline) | dextran sulfate | poly(styrene sulfonic acid) | 0 |
| 89 | poly(2-ethyl-2-oxazoline) | polyethyleneimine | 1-O-Octyl-B-D-glucopyranoside | 1 |
| 90 | poly(2-ethyl-2-oxazoline) | polyethyleneimine | Pluronic F68 | 1 |
| 91 | poly(2-ethyl-2-oxazoline) | polyethyleneimine | CHAPS | 1 |
| 92 | poly(2-ethyl-2-oxazoline) | Pluronic F68 | CHAPS | 1 |
| 93 | poly(ethylene glycol) | dextran | Ficoll | 1 |
| 94 | poly(ethylene glycol) | dextran | polyvinylpyrrolidone | 1 |
| 95 | poly(ethylene glycol) | dextran | Tween 20 | 1 |
| 96 | poly(ethylene glycol) | dextran | CHAPS | 1 |
| 97 | poly(ethylene glycol) | Ficoll | polyethyleneimine | 1 |
| 98 | poly(ethylene glycol) | Ficoll | Tween 20 | 1 |
| 99 | poly(ethylene glycol) | Ficoll | CHAPS | 1 |
| 100 | poly(ethylene glycol) | polyacrylamide | polyethyleneimine | 1 |
| 101 | poly(ethylene glycol) | polyacrylamide | Tween 20 | 1 |
| 102 | poly(ethylene glycol) | polyacrylamide | CHAPS | 1 |
| 103 | poly(ethylene glycol) | polyethyleneimine | 1-O-Octyl-B-D-glucopyranoside | 1 |
| 104 | poly(ethylene glycol) | polyethyleneimine | CHAPS | 1 |
| 105 | dextran | Ficoll | hydroxyethyl cellulose | 1 |
| 106 | dextran | Ficoll | Tween 20 | 1 |
| 107 | dextran | Ficoll | Triton X-100 | 1 |
| 108 | dextran | Ficoll | Pluronic F68 | 1 |
| 109 | dextran | Ficoll | CHAPS | 1 |
| 110 | dextran | polyvinylpyrrolidone | poly(2-acrylamido-2-methyl-1-propanesulfonic acid) | 1 |
| 111 | dextran | hydroxyethyl cellulose | Tween 20 | 1 |
| 112 | dextran | hydroxyethyl cellulose | Triton X-100 | 1 |
| 113 | dextran | Pluronic F68 | CHAPS | 1 |

TABLE S3-continued

List of identified three-phase systems: "0" refers to a MPS that Applicant did not produce; "1" refers to a MPS produced.

| Count | Polymers and Surfactants as phase components | | | |
|---|---|---|---|---|
| 114 | Ficoll | polyethyleneimine | Pluronic F68 | 1 |
| 115 | Ficoll | polyethyleneimine | CHAPS | 1 |
| 116 | Ficoll | hydroxyethyl cellulose | Tween 20 | 1 |
| 117 | Ficoll | hydroxyethyl cellulose | Triton X-100 | 1 |
| 118 | Ficoll | Pluronic F68 | CHAPS | 1 |
| 119 | polyacrylamide | polyethyleneimine | Pluronic F68 | 1 |
| 120 | polyacrylamide | polyethyleneimine | CHAPS | 1 |
| 121 | polyacrylamide | Pluronic F68 | CHAPS | 1 |
| 122 | polyethyleneimine | Pluronic F68 | CHAPS | 1 |
| 123 | PEOZ | PEG | PVPNO | 0 |
| 124 | PEOZ | PEI | PVPNO | 0 |
| 125 | PEOZ | PA | PVPNO | 0 |
| 126 | PEOZ | PMAA | PVPNO | 0 |
| 127 | PEG | PEI | PVPNO | 0 |
| 128 | PEG | PMAA | PVPNO | 0 |
| 129 | PEG | PA | PVPNO | 0 |
| 130 | PEI | PA | PVPNO | 0 |
| 131 | PEI | PMAA | PVPNO | 0 |
| 132 | PA | PMAA | PVPNO | 0 |
| 133 | PEOZ | PEG | PVPNO | 0 |
| 134 | PEOZ | TWEEN | PVPNO | 0 |
| 135 | PEOZ | PA | PVPNO | 0 |
| 136 | PEOZ | PMAA | PVPNO | 0 |
| 137 | PEG | TWEEN | PVPNO | 0 |
| 138 | TWEEN | PA | PVPNO | 0 |
| 139 | TWEEN | PMAA | PVPNO | 0 |
| 140 | PA | PMAA | PVPNO | 0 |
| 141 | PEG | PA | PVPNO | 0 |
| 142 | PEG | PMAA | PVPNO | 0 |

TABLE S4

List of identified four-phase systems: "0" refers to a MPS that Applicant did not produce; "1" refers to a MPS produced.

| Count | Phase components | | | | CONFIRMED? 0 - No, 1 - Yes |
|---|---|---|---|---|---|
| 1 | poly(methacrylic acid) | poly(2-ethyl-2-oxazoline) | poly(ethylene glycol) | Ficoll | 1 |
| 2 | poly(methacrylic acid) | poly(2-ethyl-2-oxazoline) | poly(ethylene glycol) | polyacrylamide | 1 |
| 3 | poly(methacrylic acid) | poly(2-ethyl-2-oxazoline) | poly(ethylene glycol) | poly(diallyldimethyl ammonium chloride | 0 |
| 4 | poly(methacrylic acid) | poly(2-ethyl-2-oxazoline) | poly(ethylene glycol) | polyethyleneimine | 1 |
| 5 | poly(methacrylic acid) | poly(2-ethyl-2-oxazoline) | poly(ethylene glycol) | Tween 20 | 1 |
| 6 | poly(methacrylic acid) | poly(2-ethyl-2-oxazoline) | poly(ethylene glycol) | 1-O-Octyl-B-D-glucopyranoside | 0 |
| 7 | poly(methacrylic acid) | poly(2-ethyl-2-oxazoline) | poly(ethylene glycol) | CHAPS | 1 |
| 8 | poly(methacrylic acid) | poly(2-ethyl-2-oxazoline) | Ficoll | polyethyleneimine | 1 |
| 9 | poly(methacrylic acid) | poly(2-ethyl-2-oxazoline) | Ficoll | Tween 20 | 1 |
| 10 | poly(methacrylic acid) | poly(2-ethyl-2-oxazoline) | Ficoll | Triton X-100 | 0 |
| 11 | poly(methacrylic acid) | poly(2-ethyl-2-oxazoline) | Ficoll | Pluronic F68 | 1 |
| 12 | poly(methacrylic acid) | poly(2-ethyl-2-oxazoline) | Ficoll | CHAPS | 1 |
| 13 | poly(methacrylic acid) | poly(2-ethyl-2-oxazoline) | polyacrylamide | polyethyleneimine | 1 |
| 14 | poly(methacrylic acid) | poly(2-ethyl-2-oxazoline) | polyacrylamide | Tween 20 | 1 |
| 15 | poly(methacrylic acid) | poly(2-ethyl-2-oxazoline) | polyacrylamide | Triton X-100 | 1 |
| 16 | poly(methacrylic acid) | poly(2-ethyl-2-oxazoline) | polyacrylamide | Pluronic F68 | 1 |
| 17 | poly(methacrylic acid) | poly(2-ethyl-2-oxazoline) | polyacrylamide | CHAPS | 1 |
| 18 | poly(methacrylic acid) | poly(2-ethyl-2-oxazoline) | polyethyleneimine | 1-O-Octyl-B-D-glucopyranoside | 0 1 |
| 19 | poly(methacrylic acid) | poly(2-ethyl-2-oxazoline) | polyethyleneimine | Pluronic F68 | 0 |
| 20 | poly(methacrylic acid) | poly(2-ethyl-2-oxazoline) | polyethyleneimine | CHAPS | 1 |
| 21 | poly(methacrylic acid) | poly(2-ethyl-2-oxazoline) | Pluronic F68 | CHAPS | 1 |
| 22 | poly(methacrylic acid) | poly(ethylene glycol) | Ficoll | polyethyleneimine | 1 |
| 23 | poly(methacrylic acid) | poly(ethylene glycol) | Ficoll | Tween 20 | 1 |
| 24 | poly(methacrylic acid) | poly(ethylene glycol) | Ficoll | CHAPS | 1 |
| 25 | poly(methacrylic acid) | poly(ethylene glycol) | polyacrylamide | polyethyleneimine | 1 |
| 26 | poly(methacrylic acid) | poly(ethylene glycol) | polyacrylamide | Tween 20 | 1 |
| 27 | poly(methacrylic acid) | poly(ethylene glycol) | polyacrylamide | CHAPS | 1 |
| 28 | poly(methacrylic acid) | poly(ethylene glycol) | polyethyleneimine | 1-O-Octyl-B-D-glucopyranoside | 0 1 |
| 29 | poly(methacrylic acid) | poly(ethylene glycol) | polyethyleneimine | CHAPS | 1 |

TABLE S4-continued

List of identified four-phase systems: "0" refers to a MPS that Applicant did not produce; "1" refers to a MPS produced.

| Count | Phase components | | | | CONFIRMED? 0 - No, 1 - Yes |
|---|---|---|---|---|---|
| 30 | poly(methacrylic acid) | Ficoll | polyethyleneimine | Pluronic F68 | 1 |
| 31 | poly(methacrylic acid) | Ficoll | polyethyleneimine | CHAPS | 1 |
| 32 | poly(methacrylic acid) | Ficoll | Pluronic F68 | CHAPS | 1 |
| 33 | poly(methacrylic acid) | polyacrylamide | polyethyleneimine | Pluronic F68 | 1 |
| 34 | poly(methacrylic acid) | polyacrylamide | polyethyleneimine | CHAPS | 1 |
| 35 | poly(methacrylic acid) | polyacrylamide | Pluronic F68 | CHAPS | 1 |
| 36 | poly(methacrylic acid) | polyethyleneimine | Pluronic F68 | CHAPS | 1 |
| 37 | poly(vinyl alcohol) | poly(2-ethyl-2-oxazoline) | poly(ethylene glycol) | dextran | 1 |
| 38 | poly(vinyl alcohol) | poly(2-ethyl-2-oxazoline) | poly(ethylene glycol) | Ficoll | 1 |
| 39 | poly(vinyl alcohol) | poly(2-ethyl-2-oxazoline) | poly(ethylene glycol) | polyacrylamide | 1 |
| 40 | poly(vinyl alcohol) | poly(2-ethyl-2-oxazoline) | poly(ethylene glycol) | poly(diallyldimethyl ammonium chloride | 0 |
| 41 | poly(vinyl alcohol) | poly(2-ethyl-2-oxazoline) | poly(ethylene glycol) | dextran sulfate | 1 |
| 42 | poly(vinyl alcohol) | poly(2-ethyl-2-oxazoline) | poly(ethylene glycol) | Tween 20 | 0 |
| 43 | poly(vinyl alcohol) | poly(2-ethyl-2-oxazoline) | dextran | Ficoll | 1 |
| 44 | poly(vinyl alcohol) | poly(2-ethyl-2-oxazoline) | dextran | Tween 20 | 0 |
| 45 | poly(vinyl alcohol) | poly(2-ethyl-2-oxazoline) | dextran | Pluronic F68 | 1 |
| 46 | poly(vinyl alcohol) | poly(2-ethyl-2-oxazoline) | Ficoll | Tween 20 | 1 |
| 47 | poly(vinyl alcohol) | poly(2-ethyl-2-oxazoline) | Ficoll | Pluronic F68 | 1 |
| 48 | poly(vinyl alcohol) | poly(2-ethyl-2-oxazoline) | polyacrylamide | Tween 20 | 1 |
| 49 | poly(vinyl alcohol) | poly(2-ethyl-2-oxazoline) | polyacrylamide | Pluronic F68 | 1 |
| 50 | poly(vinyl alcohol) | poly(ethylene glycol) | dextran | Ficoll | 1 |
| 51 | poly(vinyl alcohol) | poly(ethylene glycol) | dextran | Tween 20 | 1 |
| 52 | poly(vinyl alcohol) | poly(ethylene glycol) | Ficoll | Tween 20 | 1 |
| 53 | poly(vinyl alcohol) | poly(ethylene glycol) | polyacrylamide | Tween 20 | 1 |
| 54 | poly(vinyl alcohol) | dextran | Ficoll | Tween 20 | 1 |
| 55 | poly(vinyl alcohol) | dextran | Ficoll | Pluronic F68 | 1 |
| 56 | poly(2-ethyl-2-oxazoline) | poly(ethylene glycol) | dextran | Ficoll | 1 |
| 57 | poly(2-ethyl-2-oxazoline) | poly(ethylene glycol) | dextran | Tween 20 | 1 |
| 58 | poly(2-ethyl-2-oxazoline) | poly(ethylene glycol) | dextran | CHAPS | 1 |
| 59 | poly(2-ethyl-2-oxazoline) | poly(ethylene glycol) | Ficoll | polyethyleneimine | 0 |
| 60 | poly(2-ethyl-2-oxazoline) | poly(ethylene glycol) | Ficoll | Tween 20 | 1 |
| 61 | poly(2-ethyl-2-oxazoline) | poly(ethylene glycol) | Ficoll | CHAPS | 1 |
| 62 | poly(2-ethyl-2-oxazoline) | poly(ethylene glycol) | polyacrylamide | polyethyleneimine | 1 |
| 63 | poly(2-ethyl-2-oxazoline) | poly(ethylene glycol) | polyacrylamide | Tween 20 | 1 |
| 64 | poly(2-ethyl-2-oxazoline) | poly(ethylene glycol) | polyacrylamide | CHAPS | 1 |
| 65 | poly(2-ethyl-2-oxazoline) | poly(ethylene glycol) | polyethyleneimine | 1-O-Octyl-B-D-glucopyranoside | 1 |
| 66 | poly(2-ethyl-2-oxazoline) | poly(ethylene glycol) | polyethyleneimine | CHAPS | 1 |
| 67 | poly(2-ethyl-2-oxazoline) | dextran | Ficoll | Tween 20 | 1 |
| 68 | poly(2-ethyl-2-oxazoline) | dextran | Ficoll | Triton X-100 | 0 |
| 69 | poly(2-ethyl-2-oxazoline) | dextran | Ficoll | Pluronic F68 | 1 |
| 70 | poly(2-ethyl-2-oxazoline) | dextran | Ficoll | CHAPS | 0 |
| 71 | poly(2-ethyl-2-oxazoline) | dextran | Pluronic F68 | CHAPS | 1 |
| 72 | poly(2-ethyl-2-oxazoline) | Ficoll | polyethyleneimine | Pluronic F68 | 1 |
| 73 | poly(2-ethyl-2-oxazoline) | Ficoll | polyethyleneimine | CHAPS | 1 |
| 74 | poly(2-ethyl-2-oxazoline) | Ficoll | Pluronic F68 | CHAPS | 0 |
| 75 | poly(2-ethyl-2-oxazoline) | polyacrylamide | polyethyleneimine | Pluronic F68 | 1 |
| 76 | poly(2-ethyl-2-oxazoline) | polyacrylamide | polyethyleneimine | CHAPS | 1 |
| 77 | poly(2-ethyl-2-oxazoline) | polyacrylamide | Pluronic F68 | CHAPS | 0 |
| 78 | poly(2-ethyl-2-oxazoline) | polyethyleneimine | Pluronic F68 | CHAPS | 1 |
| 79 | poly(ethylene glycol) | dextran | Ficoll | Tween 20 | 1 |
| 80 | poly(ethylene glycol) | dextran | Ficoll | CHAPS | 1 |
| 81 | poly(ethylene glycol) | Ficoll | polyethyleneimine | CHAPS | 1 |
| 82 | poly(ethylene glycol) | polyacrylamide | polyethyleneimine | CHAPS | 1 |
| 83 | dextran | Ficoll | hydroxyethyl cellulose | Tween 20 | 1 |
| 84 | dextran | Ficoll | hydroxyethyl cellulose | Triton X-100 | 1 |
| 85 | dextran | Ficoll | Pluronic F68 | CHAPS | 1 |
| 86 | Ficoll | polyethyleneimine | Pluronic F68 | CHAPS | 1 |
| 87 | polyacrylamide | polyethyleneimine | Pluronic F68 | CHAPS | 1 |
| 88 | PEOZ | PEG | PEI | PVPNO | 0 |
| 89 | PEOZ | PEG | PA | PVPNO | 0 |
| 90 | PEOZ | PEI | PA | PVPNO | 0 |
| 91 | PEOZ | PEI | PMAA | PVPNO | 0 |
| 92 | PEOZ | PA | PMAA | PVPNO | 0 |
| 93 | PEG | PEI | PA | PVPNO | 0 |
| 94 | PEG | PEI | PMAA | PVPNO | 0 |
| 95 | PEG | PA | PMAA | PVPNO | 0 |
| 96 | PEI | PA | PMAA | PVPNO | 0 |
| 97 | PEOZ | PEG | PMAA | PVPNO | 0 |
| 98 | PEOZ | PEG | PA | PVPNO | 0 |
| 99 | PEOZ | PEG | TWEEN | PVPNO | 0 |
| 100 | PEOZ | TWEEN | PA | PVPNO | 0 |

TABLE S4-continued

List of identified four-phase systems: "0" refers to a MPS that Applicant did not produce; "1" refers to a MPS produced.

| Count | Phase components | | | | CONFIRMED? 0 - No, 1 - Yes |
|---|---|---|---|---|---|
| 101 | PEOZ | TWEEN | PMAA | PVPNO | 0 |
| 102 | PEOZ | PA | PMAA | PVPNO | 0 |
| 103 | PEG | TWEEN | PA | PVPNO | 0 |
| 104 | PEG | TWEEN | PMAA | PVPNO | 0 |
| 105 | PEG | PA | PMAA | PVPNO | 0 |
| 106 | TWEEN | PA | PMAA | PVPNO | 0 |

TABLE S5

List of identified five-phase aqueous systems: "0" refers to a MPS that Applicant did not produce; "1" refers to a MPS produced.

| Count | Polymers | | | | | CONFIRMED? 0 - No, 1 - Yes |
|---|---|---|---|---|---|---|
| 1 | polyvinyl alcohol | poly(2-ethyl-2-oxazoline) | poly(ethylene glycol) | dextran | Ficoll | 1 |
| 2 | poly(methacrylic acid) | poly(2-ethyl-2-oxazoline) | poly(ethylene glycol) | Ficoll | polyethyleneimine | 1 |
| 3 | poly(methacrylic acid) | poly(2-ethyl-2-oxazoline) | poly(ethylene glycol) | polyacrylamide | polyethyleneimine | 1 |
| 4 | polyvinyl alcohol | poly(2-ethyl-2-oxazoline) | poly(ethylene glycol) | dextran | Tween 20 | 1 |
| 5 | poly(methacrylic acid) | poly(2-ethyl-2-oxazoline) | poly(ethylene glycol) | Ficoll | Tween 20 | 1 |
| 6 | polyvinyl alcohol | poly(2-ethyl-2-oxazoline) | poly(ethylene glycol) | Ficoll | Tween 20 | 1 |
| 7 | polyvinyl alcohol | poly(2-ethyl-2-oxazoline) | dextran | Ficoll | Tween 20 | 1 |
| 8 | polyvinyl alcohol | poly(ethylene glycol) | dextran | Ficoll | Tween 20 | 1 |
| 9 | poly(2-ethyl-2-oxazoline) | poly(ethylene glycol) | dextran | Ficoll | Tween 20 | 1 |
| 10 | poly(methacrylic acid) | poly(2-ethyl-2-oxazoline) | poly(ethylene glycol) | polyacrylamide | Tween 20 | 1 |
| 11 | polyvinyl alcohol | poly(2-ethyl-2-oxazoline) | poly(ethylene glycol) | polyacrylamide | Tween 20 | 1 |
| 12 | poly(methacrylic acid) | poly(2-ethyl-2-oxazoline) | poly(ethylene glycol) | polyethyleneimine | 1-O-Octyl-B-D-glucopyranoside | 0 |
| 13 | polyvinyl alcohol | poly(2-ethyl-2-oxazoline) | dextran | Ficoll | Pluronic F68 | 1 |
| 14 | poly(methacrylic acid) | poly(2-ethyl-2-oxazoline) | Ficoll | polyethyleneimine | Pluronic F68 | 1 |
| 15 | poly(methacrylic acid) | poly(2-ethyl-2-oxazoline) | polyacrylamide | polyethyleneimine | Pluronic F68 | 0 |
| 16 | poly(methacrylic acid) | poly(2-ethyl-2-oxazoline) | poly(ethylene glycol) | Ficoll | CHAPS | 1 |
| 17 | poly(2-ethyl-2-oxazoline) | poly(ethylene glycol) | dextran | Ficoll | CHAPS | 1 |
| 18 | poly(methacrylic acid) | poly(2-ethyl-2-oxazoline) | poly(ethylene glycol) | polyacrylamide | CHAPS | 1 |
| 19 | poly(methacrylic acid) | poly(2-ethyl-2-oxazoline) | poly(ethylene glycol) | polyethyleneimine | CHAPS | 1 |
| 20 | poly(methacrylic acid) | poly(2-ethyl-2-oxazoline) | Ficoll | polyethyleneimine | CHAPS | 1 |
| 21 | poly(methacrylic acid) | poly(ethylene glycol) | Ficoll | polyethyleneimine | CHAPS | 1 |
| 22 | poly(2-ethyl-2-oxazoline) | poly(ethylene glycol) | Ficoll | polyethyleneimine | CHAPS | 1 |
| 23 | poly(methacrylic acid) | poly(2-ethyl-2-oxazoline) | polyacrylamide | polyethyleneimine | CHAPS | 1 |
| 24 | poly(methacrylic acid) | poly(ethylene glycol) | polyacrylamide | polyethyleneimine | CHAPS | 1 |
| 25 | poly(2-ethyl-2-oxazoline) | poly(ethylene glycol) | polyacrylamide | polyethyleneimine | CHAPS | 1 |
| 26 | poly(methacrylic acid) | poly(2-ethyl-2-oxazoline) | Ficoll | Pluronic F68 | CHAPS | 1 |
| 27 | poly(2-ethyl-2-oxazoline) | dextran | Ficoll | Pluronic F68 | CHAPS | 1 |

TABLE S5-continued

List of identified five-phase aqueous systems: "0" refers to a MPS that Applicant did not produce; "1" refers to a MPS produced.

| Count | Polymers | | | | | CONFIRMED? 0 - No, 1 - Yes |
|---|---|---|---|---|---|---|
| 28 | poly(methacrylic acid) | poly(2-ethyl-2-oxazoline) | polyacrylamide | Pluronic F68 | CHAPS | 1 |
| 29 | poly(methacrylic acid) | poly(2-ethyl-2-oxazoline) | polyethyleneimine | Pluronic F68 | CHAPS | 1 |
| 30 | poly(methacrylic acid) | Ficoll | polyethyleneimine | Pluronic F68 | CHAPS | 1 |
| 31 | poly(2-ethyl-2-oxazoline) | Ficoll | polyethyleneimine | Pluronic F68 | CHAPS | 1 |
| 32 | poly(methacrylic acid) | polyacrylamide | polyethyleneimine | Pluronic F68 | CHAPS | 1 |
| 33 | poly(2-ethyl-2-oxazoline) | polyacrylamide | polyethyleneimine | Pluronic F68 | CHAPS | 1 |
| 34 | PEG | PEI | PA | PMAA | PVPNO | 0 |
| 35 | PEOZ | PEI | PA | PMAA | PVPNO | 0 |
| 36 | PEOZ | PEG | PA | PMAA | PVPNO | 0 |
| 37 | PEOZ | PEG | PEI | PMAA | PVPNO | 0 |
| 38 | PEOZ | PEG | PEI | PA | PVPNO | 0 |
| 39 | PEOZ | PEG | PEI | PA | PMAA | 0 |
| 40 | PEG | TWEEN | PA | PMAA | PVPNO | 0 |
| 41 | PEOZ | TWEEN | PA | PMAA | PVPNO | 0 |
| 42 | PEOZ | PEG | TWEEN | PMAA | PVPNO | 0 |
| 43 | PEOZ | PEG | TWEEN | PA | PVPNO | 0 |
| 44 | PEOZ | PEG | TWEEN | PA | PMAA | 0 |

TABLE S6

List of six-phase aqueous MPS: "0" refers to a MPS that Applicant did not produce; "1" refers to a MPS produced.

| Count | Phase components | | | | | | |
|---|---|---|---|---|---|---|---|
| 1 | poly(vinyl alcohol)' | poly(2-ethyl-2-oxazoline)' | poly(ethylene glycol)' | dextran' | Ficoll' | Tween 20' | 1 |
| 2 | PMAA | PEOZ | PEG | Ficoll | PEI | CHAPS | 0 |
| 3 | PMAA | PEOZ | PEG | PA | PEI | CHAPS | 1 |
| 4 | PMAA | PEOZ | PEI | Ficoll | CHAPS | P68 | 0 |
| 5 | PMAA | PEOZ | PA | PEI | P68 | CHAPS | 1 |

Poly(2-vinylpyridine-N-oxide) Multiphase Systems

Abbreviations for polymer used in this study:
poly(2-vinylpyridine-N-oxide)-PVPNO
poly(methacrylic acid)-PMAA
poly(acrylic acid)-PAA
polyacrylamide-PA
poly(vinyl alcohol)-PVA
poly(2-ethyl-2-oxazoline)-PEOZ
poly(ethylene glycol)-PEG
hydroxyethylcelluolose-HEC
polyethyleneimine-PEI
polyvinylpyrrolidone-PVP Indicators for phase-separation results:
−miscible
+immiscible
x incompatible The phase separation results obtained are shown below:
PVPNO-PA (+)
PVPNO-PMAA (+)
PVPNO-PAA (x)
PVPNO-PVA (−)
PVPNO-PEOZ (+)
PVPNO-PEG (+)
PVPNO-HEC (−)
PVPNO-Dextran (−)
PVPNO-Ficoll (−)
PVPNO-PEI (+)
PVPNO-Tween (+)
PVPNO-PVP (−)

Two 6-Phase systems are contemplated:
PEOZ-PEG-PEI-PA-PMAA-PVPNO; and
PEOZ-PEG-TWEEN-PA-PMAA-PVPNO.

The following three-phase systems are contemplated: PEOZ-PEG-PVPNO, PEOZ-PEI-PVPNO, PEOZ-PA-PVPNO, PEOZ-PMAA-PVPNO, PEG-PEI-PVPNO, PEG-PMAA-PVPNO, PEG-PA-PVPNO, PEI-PA-PVPNO, PEI-PMAA-PVPNO, PA-PMAA-PVPNO, PEOZ-PEG-PVPNO, PEOZ-TWEEN-PVPNO, PEOZ-PA-PVPNO, PEOZ-PMAA-PVPNO, PEG-TWEEN-PVPNO, TWEEN-PA-PVPNO, TWEEN-PMAA-PVPNO, PA-PMAA-PVPNO, PEG-PA-PVPNO, and PEG-PMAA-PVPNO.

The following four-phase systems are contemplated: PEOZ-PEG-PEI-PVPNO, PEOZ-PEG-PA-PVPNO, PEOZ-PEI-PA-PVPNO, PEOZ-PEI-PMAA-PVPNO, PEOZ-PMAA-PVPNO, PEG-PEI-PA-PVPNO, PEG-PEI-PMAA-PVPNO, PEG-PA-PMAA-PVPNO, PEI-PA-PMAA-PVPNO, PEOZ-PEG-PMAA-PVPNO, PEOZ-PEG-PA- PVPNO, PEOZ-PEG-TWEEN-PVPNO, PEOZ-TWEEN-PA-PVPNO, PEOZ-TWEEN-PMAA-PVPNO, PEOZ-PA-PMAA-PVPNO, PEG-TWEEN-PA-PVPNO, PEG-TWEEN-PMAA-PVPNO, PEG-PA-PMAA-PVPNO, and TWEEN-PA-PMAA-PVPNO (see Experimental Section for the acronym of the polymers).

The following five-phase systems are contemplated: PEG-PEI-PA-PMAA-PVPNO, PEOZ-PEI-PA-PMAA-PVPNO, PEOZ-PEG-PA-PMAA-PVPNO, PEOZ-PEG-PEI-PMAA-PVPNO, PEOZ-PEG-PEI-PA-PVPNO, PEOZ-PEG-PEI-PA-PMAA, PEG-TWEEN-PA-PMAA-PVPNO, PEOZ-TWEEN-PA-PMAA-PVPNO, PEOZ-PEG-TWEEN-PMAA-PVPNO, PEOZ-PEG-TWEEN-PA-PVPNO, and PEOZ-PEG-TWEEN-PA-PMAA (see Experimental Section for the acronym of the polymers).

Multiphase Systems of Liquid Polymers

The following liquid polymers were used for preparing solvent-free MPS comprising liquid polymer phases.
(1) poly(propylene glycol)-PPG; INSOLUBLE in water.
(2) poly(ethylene glycol)-PEG; molecular weight <1000 Da (above this molecular weight, it is a solid); SOLUBLE in water.
(3) Pluronic L121-PL, a PEG-PPG block co-polymer is a liquid; INSOLUBLE in water
(4) polydimethylsiloxane-PDMS; INSOLUBLE in water.
(5) poly(ethyl vinyl ether)-PEVE; INSOLUBLE in water
(6) polybutadiene-PBD; INSOLUBLE in water The following 2 phases liquid polymer MPSs were prepared:
PPG-PEG;
PPG-PL;
PPG-PDMS;
PPG-PBD;
PEG-PL;
PEG-PDMS;
PEG-PEVE;
PEG-PBD;
PL-PDMS;
PL-PBD;
PDMS-PEVE;
PDMS-PBD; and
PEVE-PBD.

The following 3 phases liquid polymer MPSs were studied: (0=predicted; 1=confirmed by preparation)
PPG-PEG-PL (1);
PPG-PDMS-PBD (1);
PPG-PEG-PBD (1);
PEG-PEVE-PBD (1);
PEG-PEVE-PDMS (1);
PPG-PEG-PDMS (1);
PEG-PL-PDMS (0);
PEG-PL-PBD (1);
PL-PDMS-PBD (1); and
PDMS-PEVE-PBD (1).

The following 4 phases liquid polymer MPSs were studied: (0=predicted; 1=confirmed by preparation)
PPG-PEG-PL-PDMS (0);
PPG-PEG-PL-PBD (0);
PPG-PEG-PDMS-PBD (1);
PPG-PL-PDMS-PBD (0); and
PEG-PL-PDMS-PBD (1).

The following 4 phases liquid polymer MPS was predicted:
PPG-PEG-PL-PDMS-PBD (0).

Example 2. Preparation of a Model MPS Separations System

Applicants used immiscible aqueous polymer solutions of polyvinyl alcohol (PVA), PEG, and dextran to form three discontinuous density barriers with designed densities for partitioning different analytes with different densities.

Applicants have previously reported on the utilization of an eggbeater as a portable centrifuge for point-of-care diagnostics (soft centrifuge). Briefly, a length of heat-sealed polyethylene tubing that contains the sample is taped to a blade of an eggbeater paddle. Manual cranking of the eggbeater can comfortably achieve relative centrifugal forces (RCF) ranging from 240-350×g.

Applicants prepared the triphasic aqueous density barriers by first mixing each polymer and then pipetting the mixture into the tubing. The three polymer phases spontaneously formed after five minutes of centrifugation using the eggbeater. Applicants then removed the tubing from the blade, introduced 5-10 µL of sample to the top layer (by the displacement of a thin wire), and reapplied the tubing to the paddle.

Figure 3A:
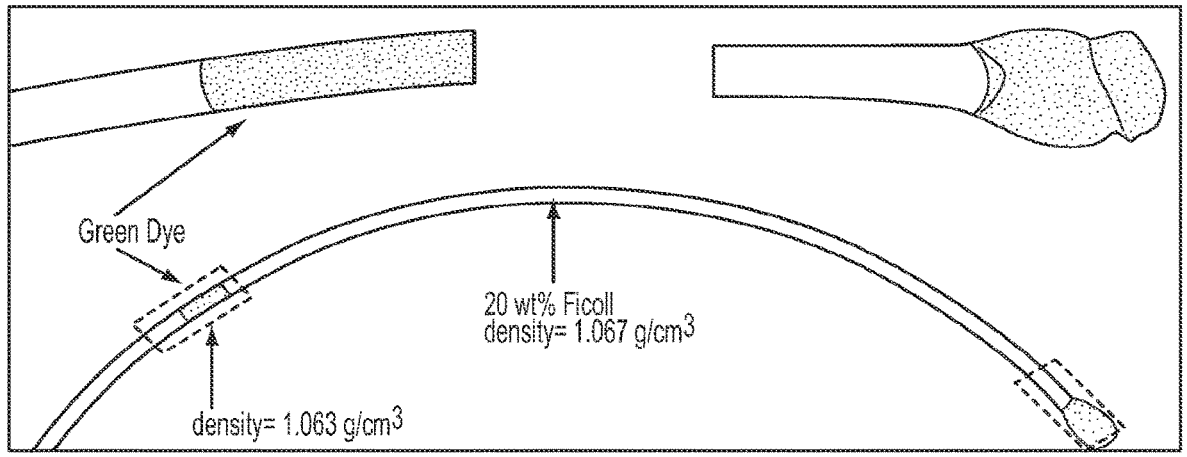
FIG. 3A-3B shows images of a single barrier separating density standards beads based on small differences in density.
Figure 3B:
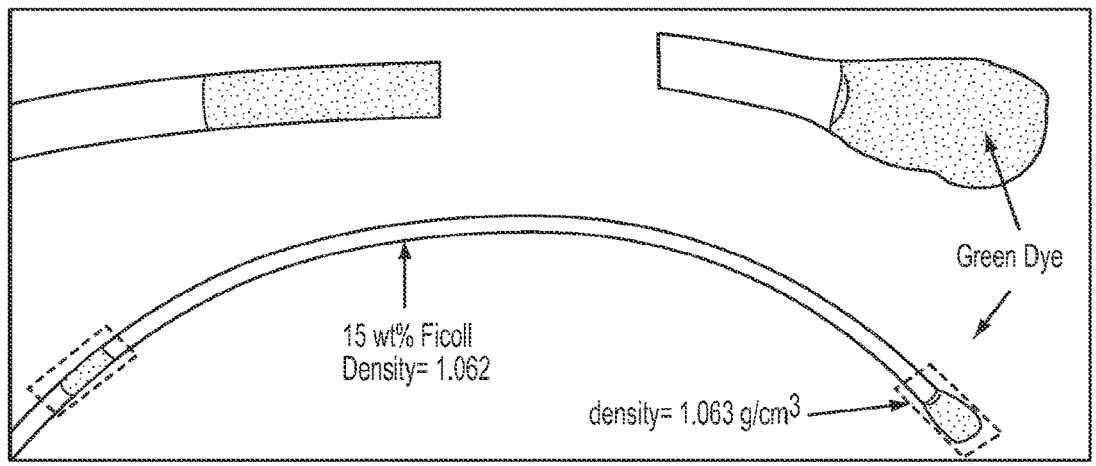

Applicants used individual solutions of polymers to demonstrate the sensitive ($\Delta\rho \geq 0.001$ g/cm$^3$) and rapid separation of microsphere standards across the density barrier. For example, the density of a 15 wt % solution of poly(styrene sulfonic acid) (PSSA) 500 k is 1.062 g/cm$^3$ and a green-dyed microsphere standard with a density of 1.063 g/cm$^3$ pellets in less than five minutes (FIG. 3(A)). Conversely, this same standard will stack on top of a 40 wt % solution of PEG 20 k ($\rho$=1.067 g/cm$^3$; FIG. 3(B)).

Example 3. AMPS Comprising Surfactants

Properties of the surfactants used are shown in Table S7.

TABLE S7

Properties of the surfactants Applicants have used in this study.

| | Surfactant | Mw (g/mol) | Concentration | Density g/cm$^3$ |
|---|---|---|---|---|
| | Non-Ionic | | | |
| A | Zonyl | N/A | 50% (v/v) | 1.037 |
| B | Brij 35 | ~1,198 | 30% (v/v) | 1.025 |
| C | Tween 20 | ~1,228 | 45% (v/v) | 1.067 |
| D | Triton X-100 | ~625 | 20% (v/v) | 1.017 |
| E | Nonylphenol polyoxyethylene (20) | ~13,420 | 40% (v/v) | 1.035 |
| F | 1-O-Octyl-β-D-glucopyranoside | 292.37 | 100 mg/ml | 1.011 |
| G | Pluronic F68 | ~8,400 | 340 mg/ml | 1.049 |
| | Ionic (negative) | | | |
| H | sodium dodecylsulfate | 288.38 | 350 mg/ml | 0.998 |
| I | DOWFAX 2A1 | N/A | 67% (v/v) | 1.096 |
| J | sodium cholate | 408.57 | 430 mg/ml | 0.997 |

TABLE S7-continued

Properties of the surfactants Applicants have used in this study.

| Surfactant | | Mw (g/mol) | Concentration | Density g/cm$^3$ |
|---|---|---|---|---|
| Zwitterionic | | | | |
| K | N,N-dimethyldodecylamine N-oxide | 229.4 | 24% (v/v) | 1.123 |
| L | CHAPS | 614.88 | 250 mg/ml | 1.042 |

Phase Separation

Applicants added equal volumes of polymer and surfactant solutions (200 μL) into an Eppendorf tube (plastic test tube), thoroughly mixed the contents through vortexing for at least 30 seconds, and centrifuge the tube at 2,000×g for at least 10 minutes.

Coloring of Multiphase Systems

Applicants added the components of a multiphase system in equal volumes along with 10 uL of a 10 mg/ml solution of a desired dye such as allura red or ethyl orange into an Eppendorf tube and thoroughly mixed the contents through vortexing for at least 30 seconds. Thereafter, Applicants transferred this homogenous solution into a sealed capillary glass tube with a syringe, and centrifuged this capillary tube at 6,000×g for 30 minutes. Lists of 2-, 3-, and 4-phase systems prepared with polymers and surfactants are found in Tables S2, S3 and S4, respectively.

Example 4. MPS in Patterned Paper

FIG. 10 (A) illustrates a phase-separated poly(ethylene glycol)/poly(methacrylic acid) (PEG/PMAA) two-phase system (left) and phase-separated PEG/PMAA/Allura Red system (right), wherein Allura Red selectively stained the top phase. As shown in FIG. 10 (B), Applicants separated the top and bottom phases and spotted them onto a wax-printed paper. The paper was folded such that the phases came into contact. Even after close contact, Applicants did not observe the intermixing of the phases, as demonstrated by the fact that the Allura Dye remained in the hydrophilic region 1.

In another experiment, selective diffusion of Allura Red in PEG/PMAA two-phase system on paper is shown (FIG. 11). As shown in FIG. 11(A)(i), 20 mg/ml Allura Red solution was loaded on the hydrophilic regions on wax-printed paper and dried. As shown in FIG. 11(A)(ii), the top and bottom phases of a PEG/PMAA two-phase system were spotted onto another wax-printed paper, the paper was folded and sandwiched the dried Allura Red-spotted paper in between the top of bottom phases through folding. The solution in the top and bottom phases and the Allura Red were allowed to be in contact and in equilibrium for about 5 minutes and then the paper was unfolded. As shown in FIG. 11B, the dissolved dye predominantly accumulated in the top phases.

Example 5. MPS in Organic Solvent

Applicants have discovered that certain polymers and surfactant will phase-separate in organic solution. A summary of polymers and surfactants used in organic MPS is listed in Table S12. Tables S12 shows the properties of the polymers stock solutions in dichloromethane: weight average molecular weights of the polymers (kDa), concentrations (% w/v), densities (g/cm$^3$), and refractive indices.

TABLE S12

List of polymers, their acronym and surfactants used in organic MPS.

| | polymer | acronym | avg. Mw (kDa) | % w/v | density (g/cm$^3$) | refractive index |
|---|---|---|---|---|---|---|
| 1 | poly(bisphenol A carbonate) | PBPA | 64 | 30 | | 1.484 |
| 2 | Polysulfone | PSulf | 67 | 15 | | 1.455 |
| 3 | Polydimethylsiloxane 200 ® | PDMS | 1.3 | 50 | | 1.409 |
| 4 | Polystyrene | PS | 50 | 30 | | 1.480 |
| 5 | poly(4-vinylpyridine) | PVPy | 50 | 30 | 1.298 | 1.492 |
| 6 | Polyvinylpyrrolidone | PVP | 55 | 35 | | 1.482 |
| 7 | poly(2-ethyl-2-oxazoline) | PEOZ | 50 | 30 | 1.284 | 1.474 |
| 8 | Polyethyleneimine | PEI | 25 | 30 | | 1.461 |
| 9 | Poly(methylmethacrylate-co-methacrylic acid) (1:0.016) | PMAA-PMMA copolymer | 34 | 30 | | 1.447 |
| 10 | poly(methyl methacrylate) | PMMA | 35 | 30 | 1.299 | 1.461 |
| 11 | polyoxyethylene (20) sorbitan monolaurate | Tween | 1.2 | 50 | 1.240 | 1.450 |
| 12 | poly(tetrahydrofuran) | PTHF | 2.9 | 30 | | 1.442 |
| 13 | poly(propylene glycol) | PPG | 4 | 35 | | 1.439 |
| 14 | poly(ethylene glycol) | PEG$_{20k}$ | 20 | 40 | | 1.454 |
| 15 | polyvinyl acetate) | PVA | 100 | 30 | | 1.436 |
| 16 | Polycaprolactone | PCL | 80* | 25 | | 1.447 |
| 17 | poly(ethylene glycol) | PEG$_{100k}$ | 100 | 20 | | |
| 18 | poly(ethylene glycol) monomethyl ether | PEG$_{2k}$ | 2 | 40 | | |
| 19 | Triethylene glycol monomethyl ether | TEG | 0.16 | 40 | | |
| 20 | Poly(methacrylic acid) | PMAA | 34 | 30 | | 1.447 |

*Number average molecular weight.

A six-phase organic MPS was produced in this study. The MPS was produced using dichloromethane as the solvent and the phase component composition of the six phases are PBPA-PDMS-PS-PVPy-PEOZ-PCL.

Figure 5:
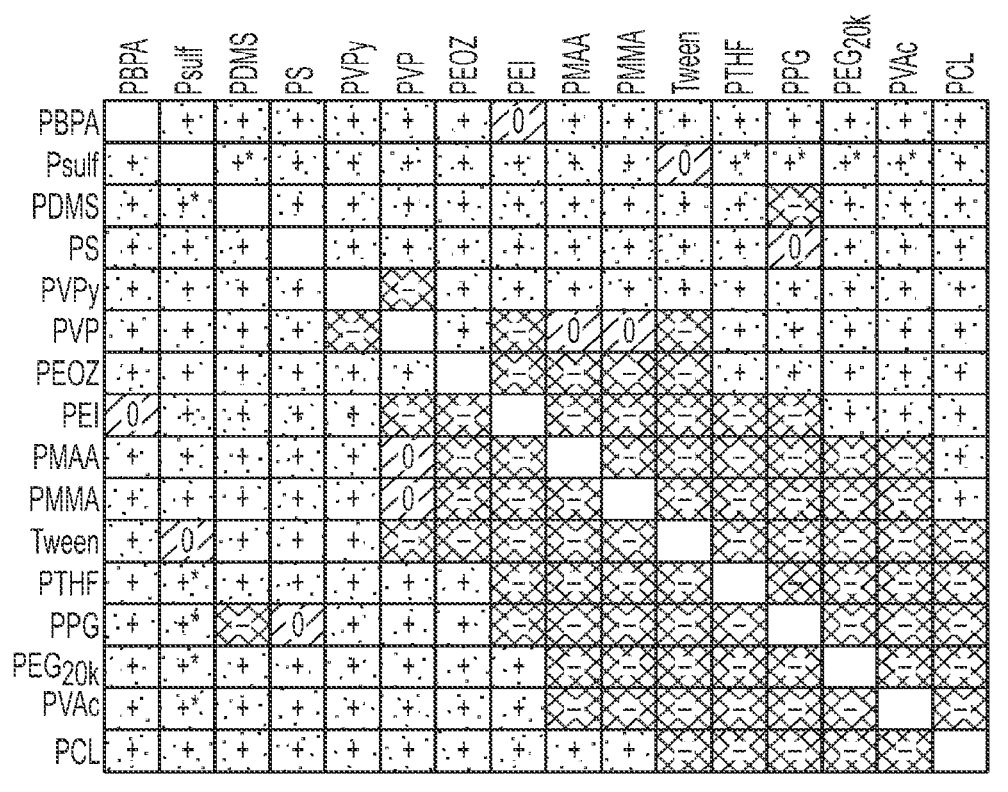

Also, various two-phase organic MPS were investigated and the result is summarized in FIG. 5. As shown in FIG. 5, dichloromethane-polymer-polymer ternary mixtures were categorized as either biphasic (+), homogeneous (−), or incompatible (0). 76 mixtures (63%) formed two phases, 39 mixtures are homogeneous (33%), and 5 mixtures (4%) are incompatible. Asterisks indicated mixtures that were formed at half the concentration of the stock polymers.

Example 6. MPS Comprising Aqueous and Non-Aqueous Phases

Figures 12A, 12B:
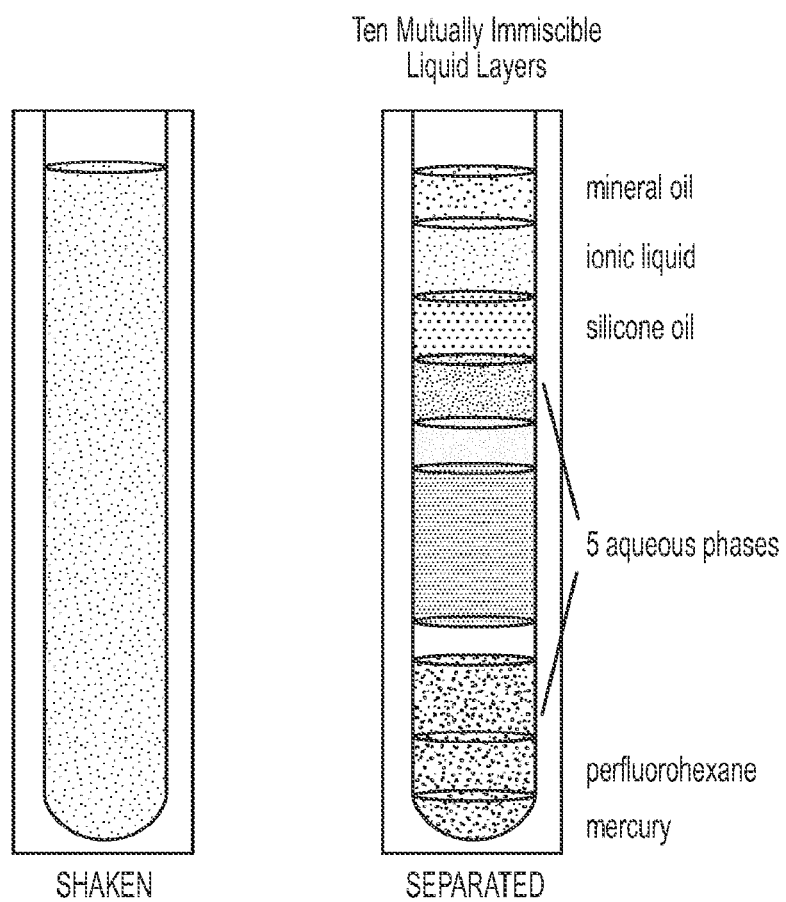
FIG. 12A shows a shaken mixture of mineral oil, ionic liquid, silicone oil, perfluorohexane, mercury, and five aqueous phase component stock solution.
FIG. 12B shows a 10-phase MPS including, from top to bottom, a mineral oil phase, a ionic liquid phase, a silicone oil phase, 5 aqueous phases, a perfluorohexane phase, and a mercury phase.

A 10-phase MPS is shown in FIG. 12. The MPS was constructed by mixing mineral oil, ionic liquid, silicone oil, perfluorohexane, mercury, and five aqueous phase component stock solutions (FIG. 12A). After the mixture was shaken thoroughly, it was allowed to phase separate to form the 10-phase MPS as shown in FIG. 12B. From the top to bottom, the 10-phase MPS has the following phases: a mineral oil phase, a ionic liquid phase, a silicone oil phase, 5 aqueous phases, a perfluorohexane phase, and a mercury phase. The 10 phases are arranged according to density.

Density Calculation for Beads

Polymers and Beads. Applicants purchased the following polymers: poly(ethylene glycol) (Sigma-Aldrich; MW=20,000 Da), Ficoll (Alfa Aesar; MW=400,000 Da), and dextran (Spectrum Chemical; 250,000 Da). Applicants used each polymer without further purification, and prepared stock aqueous solutions at a concentration of 30% (wt/vol) without adding salt or titrating the pH. Applicants purchased a series of glass density standard floats (i.e., "beads") from American Density Materials, the densities of which spanned 1.0400 g/cm$^3$ to 1.1000 g/cm$^3$. The vendor certified that the density of each bead was calibrated to ±0.0002 g/cm$^3$ at 23° C., and the average diameter of each bead was approximately 5 mm. Applicants purchased polystyrene beads of uncharacterized density from McMaster-Carr. The average diameter of these beads was ⅛" (3.175 mm).

Phase Separation and Analysis.

To prepare aqueous two-phase polymer systems (ATPS), Applicants added equivalent volumes of polymer solutions (either at stock concentrations or a dilution) into a container (e.g., Eppendorf tube or plastic cuvette), thoroughly mixed the solutions by vortex for 30 seconds, and accelerated phase separation by centrifugation at 2000 g for 2-10 minutes. Phase separation would occur in the absence of centrifugation (i.e., under a standard gravitational field of 1g) over a period of time that depended on the viscosity of the solutions and the difference in density between each phase, anywhere from minutes to hours. Applicants removed an aliquot of each phase (ca. 800 μL) in order to analyze the density of each layer by oscillating U-tube densitometry (Anton Paar DM35N). Applicants measured the interfacial tension between the top and bottom phases by the spinning drop method using a tensiometer.

Separation of Beads Based on Density.

Using the density step produced by a dextran-Ficoll ATPS, Applicants demonstrated in the manuscript that each two-phase system could separate objects based on density into three positions: (i) floating at the surface of the top phase, (ii) at the interface between phases, and (iii) settled at the bottom of the container. This type of separation can occur independently of the densities of each aqueous phase, the magnitude of the density step, and the polymers employed to generate the ATPS. In FIG. 8, Applicants demonstrate the separation of three beads using the density step produced by a poly(ethylene glycol)-Ficoll ATPS (Δρ=0.0802 g/cm$^3$; $\rho_t$=1.0320 g/cm$^3$; $\rho_b$=1.1122 g/cm$^3$).

Using the Interface to Calculate Densities.

Figure 9:
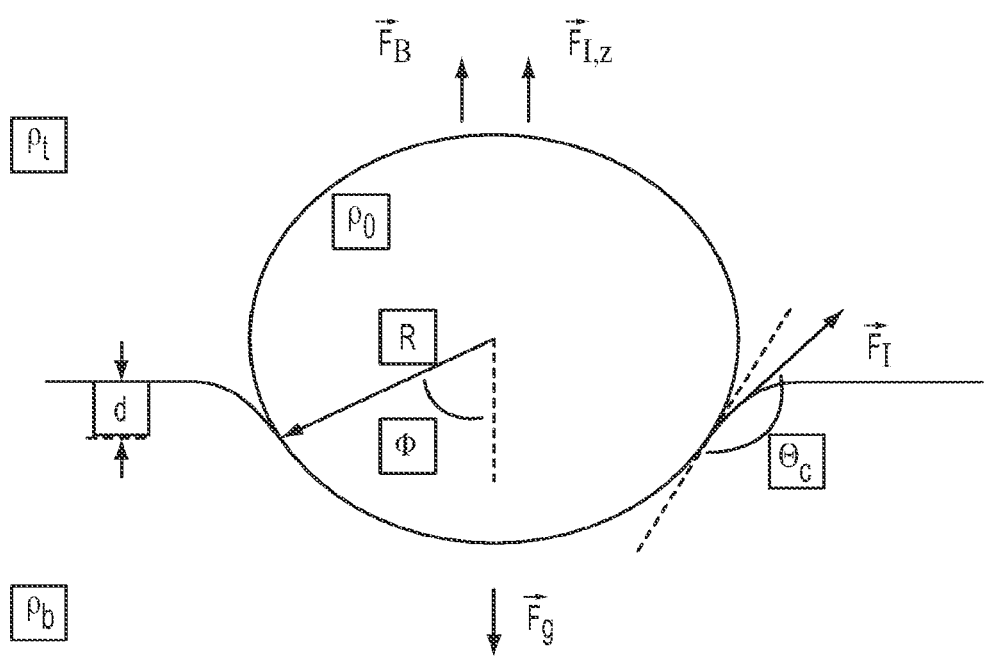
FIG. 9 shows a schematic of the forces acting on a sphere at an interface.

It was observed that the absolute position of a bead captured at the interface between layers of an ATPS depended on the density of the bead, the densities of each layer, and the contact angle between the bead and the interface. See equation (1). Eq. 1 can be expressed as a function of densities and several geometric parameters (i.e., angles and distances), as depicted in FIG. 9.

Applicants are given a sphere with a radius R (m) and density $\rho_0$ (g/cm$^3$) sitting at equilibrium at an interface between two liquids. The top liquid has a density $\rho_t$ (g/cm$^3$), the bottom liquid has a density $\rho_b$ (g/cm$^3$). The level between the liquids at equilibrium is at a height of C (m) in the z direction, $$C = -R \cos \alpha \qquad (2)$$

where α is the inclination angle (deg) measured from the negative z axis up towards the origin. Similarly defined, the angle ϕ (deg) indicates where the sphere is incident with the interface. Let $\theta_c$ (deg) define the contact angle between the surface of the sphere and the interface; hence, $\theta_c + \phi - \pi$ (deg) is the inclination angle of the liquid/liquid interfacial tension ($\gamma_{br}$; N/m) in the z direction.

Applicants can simplify the calculations by shifting to the relative bouyant densities; Applicants define $\rho_R = \rho_b - \rho_t$ and $\rho_S = \rho_0 - \rho_t$.

The Gravitational Force, $F_g$ $$F_g = -\frac{4}{3}\pi R^3 \rho_S g \qquad (3)$$

The Buoyant Force, $F_B$, Derived from the Hydrostatic Pressure Integral.

The hydrostatic pressure is only a function of the depth of the bead into the bottom layer, in this case:

$$P(\theta) = \rho_R g (C - R \cos \theta) \hat{z} \qquad (4)$$

Where C is defined from above to give us F (α)=Q $$F_B = \oint P \cdot \hat{n} dS \qquad (5)$$

$$F_B = 2\pi \rho_R g \int_{\pi-\phi}^{\pi} (C - R \cos \theta) R^2 \sin \theta \cos \theta \, d\theta \qquad (6)$$

$$F_B = 2\pi \rho_R g \int_{\pi-\phi}^{\pi} C R^2 \sin \theta \cos \theta \, d\theta - 2\pi \rho_R g \int_{\pi-\phi}^{\pi} R \cos \theta R^2 \sin \theta \cos \theta \, d\theta \qquad (7)$$

$$F_B = \pi \rho_R g C R^2 \int_{\pi-\phi}^{\pi} 2 \sin \theta \cos \theta \, d\theta + 2\pi R^3 \rho_R g \int_{\pi-\phi}^{\pi} \cos^2 \theta \, d\theta \qquad (8)$$

Note that 2 sin θ cos θ=sin(2θ) and let θ'=2θ.

$$F_B = \frac{1}{2}\pi \rho_R g C R^2 \int_{2\pi-2\phi}^{2\pi} \sin\theta' \, d\theta' + 2\pi R^3 \rho_R g \left(\frac{\cos^3 \theta}{3}\right)\bigg|_{\pi}^{\pi-\phi} \qquad (9)$$

$$F_B = \frac{1}{2}\pi \rho_R g C R(-\cos(2\pi) + \cos(2\pi - 2\phi)) + \frac{2}{3}\pi R^3 \rho_R (\cos^3(\pi-\phi) - \cos^3 \pi) \qquad (10)$$

$$F_B = \frac{1}{2}\pi \rho_R g C R^2 (-2\sin^2 \phi) + \frac{2}{3}\pi \rho_R g R^3 (-\cos^3 \phi + 1) \qquad (11)$$

$$F_B = -\pi \rho_R g C R^2 (\sin^2 \phi) + \frac{2}{3}\pi \rho_R g R^3 (1 - \cos^3 \phi) \qquad (12)$$

If the distance between the equilibrium level and the wetted surface is d (m), $$C + d = R \cos \phi \Rightarrow C = R \cos \phi - d \qquad (13)$$

$$F_B = -\pi\rho_R gR^3(\cos\phi - \cos^3\phi) + \quad (14)$$
$$\pi\rho_R gdR^2\sin^2\phi + \frac{2}{3}\pi\rho_R gR^3 - \frac{2}{3}\pi\rho_R gR^3\cos^3\phi$$

$$F_B = -\pi\rho_R gR^3\cos\phi + \pi\rho_R gR^3\cos^3\phi + \quad (15)$$
$$\pi\rho_R gdR^2\sin^2\phi + \frac{2}{3}\pi\rho_R gR^3 - \frac{2}{3}\pi\rho_R gR^3\cos^3\phi$$

$$F_B = -\pi\rho_R gR^3\cos\phi + \pi\rho_R gdR^2\sin^2\phi + \frac{2}{3}\pi\rho_R gR^3 + \frac{1}{3}\pi\rho_R gR^3\cos^3\phi \quad (16)$$

The Interfacial Tension, $F_I$.

Exploiting the rotational symmetry, Applicants just need the z component of the interfacial tension, $\gamma_{bt}$, times the line over which it is applied:

$$F_I = L \times \gamma_{bt}^z \quad (17)$$

$$F_I = 2\pi R\gamma_{bt} \sin\phi \cos(\theta_c + \phi - \pi) \quad (18)$$

Equation for Density of an Object.

Applicants can now substitute eq. 3, eq. 16, and eq. 18 into eq. 1, and set their sum to zero:

$$0 = -\frac{4}{3}\pi\rho_S gR^3 - \pi\rho_R gR^3\cos\phi + \pi\rho_R gdR^2\sin^2\phi + \quad (19)$$
$$\frac{2}{3}\pi\rho_R gR^3 + \frac{1}{3}\pi\rho_R gR^3\cos^3\phi + 2\pi R\gamma_{bt}\sin\phi\cos(\theta_c + \phi - \pi)$$

$$0 = -\rho_S - \frac{3}{4}\rho_R\cos\phi + \frac{3}{4}\rho_R\frac{d}{R}\sin^2\phi\frac{1}{2}\rho_R + \quad (20)$$
$$\frac{1}{4}\rho_R\cos^3\phi + \frac{3\gamma_{bt}}{2gR^2}\sin\phi\cos(\theta_c + \phi - \pi)$$

Applicants then substitute the original densities for $\rho_R$ and $\rho_S$:

$$0 = -(\rho_1 - \rho_3) - \frac{3}{4}(\rho_2 - \rho_3)\cos\phi + \frac{3}{4}(\rho_2 - \rho_3)\frac{d}{R}\sin^2\phi + \quad (21)$$
$$\frac{1}{2}(\rho_2 - \rho_3) + \frac{1}{4}(\rho_2 - \rho_3)\cos^3\phi + \frac{3\gamma_{bt}}{2gR^2}\sin\phi\cos(\theta_c + \phi - \pi)$$

Applicants can now solve for the unknown density, $\rho_0$, of the bead:

$$\rho_0 = \frac{(\rho_b + \rho_t)}{2} + \frac{(\rho_b - \rho_t)}{4}\left[\cos^3\phi - 3\cos\phi + 3\frac{d}{R}\sin^2\phi\right] + \quad (22)$$
$$\frac{3\gamma_{bt}}{2gR^2}\sin\phi\cos(\theta_c + \phi - \pi)$$

Geometric Measurements.

Applicants use a camera to acquire images of the beads captured at the interface. Applicants import the images into Adobe Illustrator in order to (i) outline the border of the bead, (ii) determine the position of the center of the bead, and (iii) identify the point of intersection between the bead and the interface. Using these guides, Applicants measure R, d, $\phi$, and $\theta_c$ using ImageJ or othe similar image editing/analysis software such as MATLAB, Gimp, etc. ImageJ measures angle absolutely, but all distances are measured in pixels. Applicants use the standardized width of the cuvette (10 mm) to calibrate z and R measurements.

A PEG-Ficoll ATPS with a large density step ($\Delta\rho=0.0802$ g/cm$^3$) was prepared to analyze several density standard beads over a range of densities using a single interface using equation (2) (Table S12). Geometric measurements routinely calculated the density of a bead to an accuracy better than 1% over densities that spanned 1.0400 g/cm$^3$ to 1.1000 g/cm$^3$ using this density step. This method was used to determine the unknown density of a polystyrene bead. Using the geometric measurements of the bead at the interface, the density of the polystyrene bead was calculated to be 1.0466 g/cm$^3$, which was in excellent agreement to its density as measured by magnetic levitation (1.0456 g/cm$^3$). Since the interfacial tension, $\gamma_{bt}$, is very small (on the order of μN/m, typically) for ATPS, the buoyancy correction term dominates equation 2. Therefore, smaller density steps should provide more accurate density measurements. Using the density step generated by the dextran-Ficoll ATPS ($\Delta\rho=0.0023$ g/cm$^3$), the density of a glass bead captured at the interface was measured to a very high precision, 0.06% or 0.0006 g/cm$^3$.

TABLE S12

Comparison of densities measured using ATPS. For a set of beads, Applicants compare the known densities to those measured geometrically using the density step between layers and the position of the beads at the ATPS interface.

| Material | Density Step (g/cm$^3$) | Known Density[†] (g/cm$^3$) | Measured Density[‡] (g/cm$^3$) | Density Difference (g/cm$^3$) | Density Difference (%) |
|---|---|---|---|---|---|
| | 0.080 | | | | |
| glass | | 1.0400 ± 0.0002 | 1.0367 | −0.0033 | −0.32 |
| polystyrene | | 1.0456 ± 0.0009 | 1.0466 | 0.0010 | 0.10 |
| glass | | 1.0500 ± 0.0002 | 1.0489 | −0.0011 | −0.10 |
| glass | | 1.0600 ± 0.0002 | 1.0464 | −0.0136 | −1.28 |
| glass | | 1.0700 ± 0.0002 | 1.0616 | −0.0084 | −0.79 |
| glass | | 1.0800 ± 0.0002 | 1.0689 | −0.0122 | −1.02 |
| glass | | 1.0900 ± 0.0002 | 1.0812 | −0.0088 | −0.81 |
| glass | | 1.1000 ± 0.0002 | 1.0924 | −0.0076 | −0.68 |
| | 0.002 | | | | |
| glass | | 1.0790 ± 0.0002 | 1.0796 | 0.0006 | 0.06 |

[†]Each glass bead's density and density tolerances is certified by vendor. The density of polystyrene beads is calcualted. The standard deviation was calculated from seven measurements.
[‡]The average density and standard deviation for each bead were calculated from seven measurements.

Example 6. An Aqueous MPS Deposited on Paper

Figures 10A, 10B:
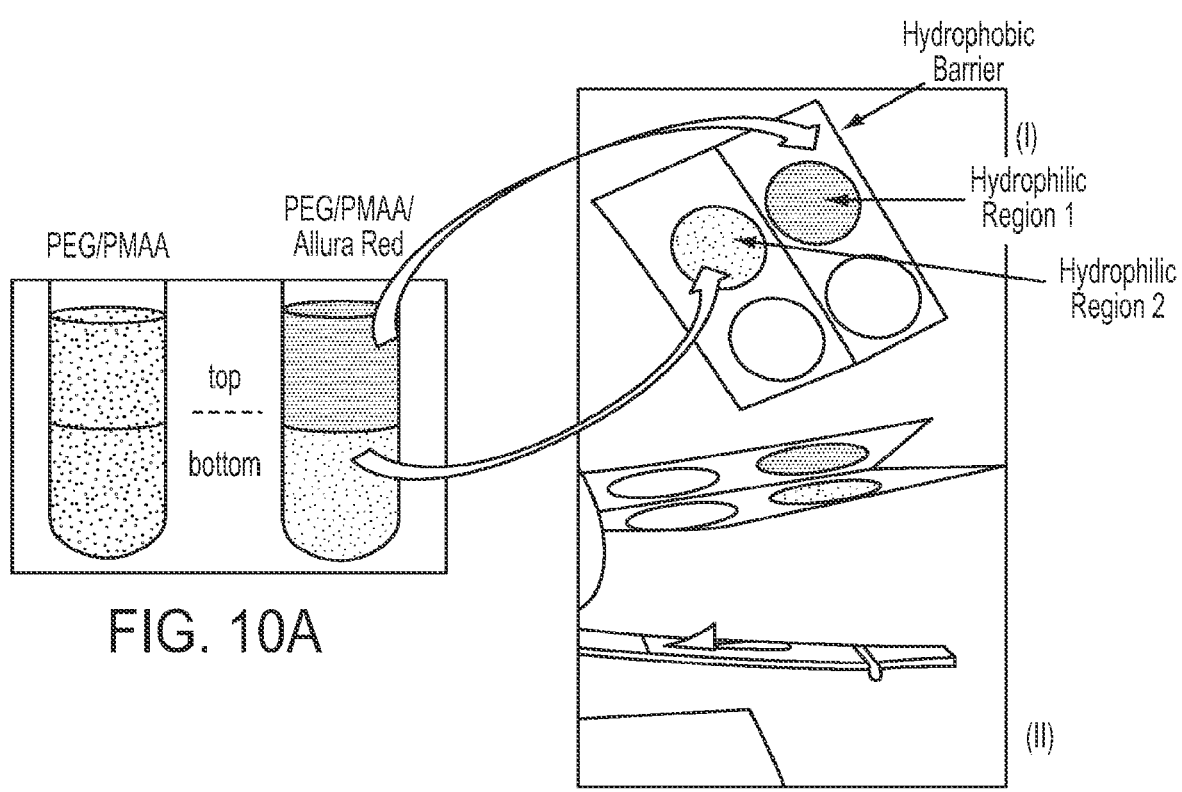
FIG. 10 A illustrates a two-phase MPS deposited on patterned-paper.

As shown by FIG. 10A, a two-phase aqueous MPS using poly(ethylene glycol) (PEG) and poly(methacrylic acid) (PMAA) as the phase component in each phase is shown to form in a tube (FIG. 10A). Also shown in FIG. 10A, Allura Red, a chemical able to selectively accumulate in the PEG phase, is included to help the visualization of the phase separation. In FIG. 10B, a patterned paper is shown where hydrophic regions, e.g., hydrophilic regions 1 and 2 (light-gray circle), are surrounded by hydrophobic barrier (black regions). The top phase containing PEG and Allura Red is loaded onto hydrophilic region 1 and the bottom phase is loaded onto hydrophilic region 2 (FIG. 10B(i)). As shown in FIG. 10B, the patterned paper is then folded along the line shown so that hydrophilic regions 1 and 2 are allowed to be in contact and the two phases are in equilibrium (FIG. 10B(ii)). The two phases remain in phase separation as demonstrated by the fact that the Allura Red dye, shown by the dark gray color, remains in the hydrophilic region 1 only.

Example 7. Shifting the Density Range of a MPS Using $D_2O$

Figure 13:
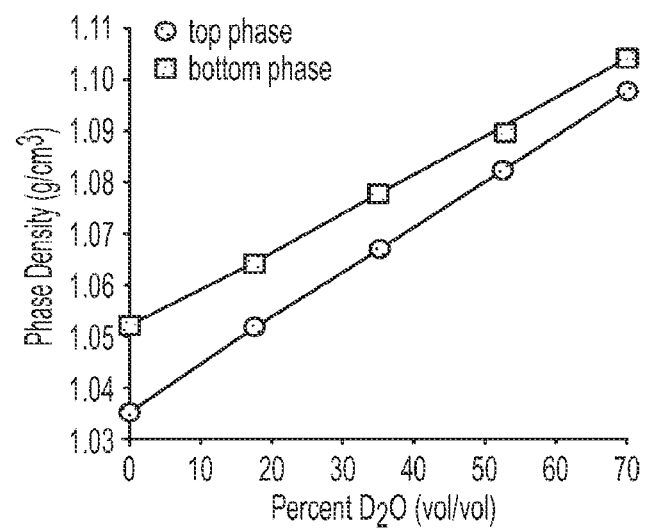
FIG. 13 shows a MPS's density range change with the addition of isotopic water.

Applicants prepared stock solutions of 20% (wt/vol) poly(2-ethyl-2-oxazoline) and 30% (wt/vol) poly(ethylene glycol) in aqueous solutions whose water content ranged from 100% $H_2O$ to 70% $D_2O$/30% $H_2O$. Applicants generated a series of two-phase AMS from mixtures of these solutions and measured the densities of each phase using densitometry (FIG. 13).

The relationship between the concentration of $D_2O$ added to the mixture of polymer solutions and the density of each phase is linear ($R^2>0.998$), but the slopes of the linear fit to each set of data are not parallel: the slopes, m (in units of $g/cm^3$/% $D_2O$), for the top and bottom phases are 8.9E-4 and 7.4E-4, respectively.

These results do not provide evidence that $D_2O$ partitions between the phases of the AMS; rather, these results are consistent with the observation that the concentrations of solutes differ between phases of aqueous two-phase systems. Since a greater concentration of solutes is related to a greater occupied solution mass fraction, the phase with less total water will incorporate less total $D_2O$ at equivalent concentrations. The density of this phase will thus increase at lower rate compared to the density of a phase with a lower concentration of solutes (i.e., more water).

Applicants used $^1H$-NMR to quantify the concentration of water in each phase: the concentrations of water in the top and bottom phases were 38.5 M (69% by volume) and 31.8 M (57% by volume), respectively. The ratio of the concentrations of water in each phase (1.2) is equivalent to the ratio of the slopes that we observe for the phase density as a function of $D_2O$ concentration.

Example 8. Shifting the Density Range of a MPS Using Salts

Applicants also examined the use of adding water-soluble salts into AMS as a method to increase the densities of the phases of an AMS independently of the magnitude of the step in density between phases.

Figure 14:
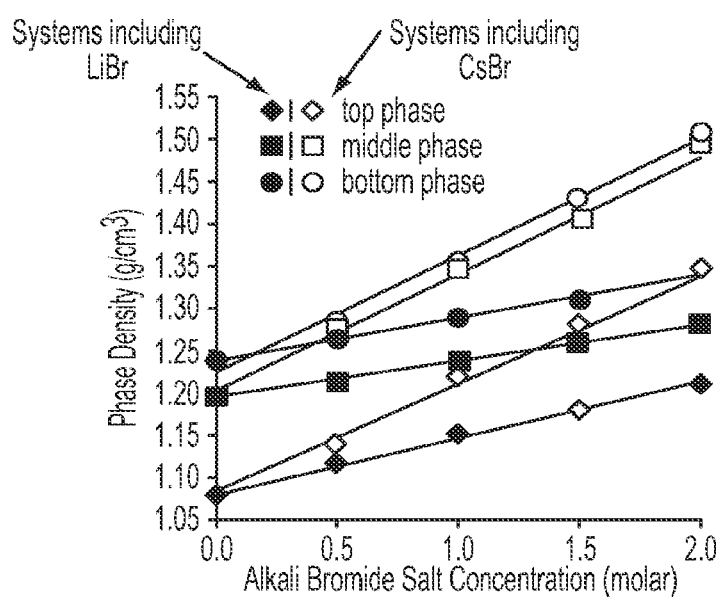
FIG. 14 shows a MPS's density range change with the addition of salt.

Applicants prepared a series of three-phase AMS from mixtures of 30% (wt/vol) poly(ethylene glycol), 40% (wt/vol) Ficoll, and 40% (wt/vol) poly(methacrylic acid) that also included alkali bromide salts, one of lithium bromide through cesium bromide, at concentrations from 0 M to 2 M. Although these salts are soluble in water at concentrations greater than 5 M, the presence of polymers in solution lowered the solubility of the salts. After phase separation, we removed samples from each phase and measured their densities using densitometry. FIG. 14 illustrates the effects on phase density after LiBr and CsBr salts were added to the MPSs. In FIG. 14, the data points are 0 M salt concentration corresponds to a MPS without any salt added. The densities of the phases increased with the increasing salt concentrations.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

The invention claimed is:

1. A method of analyzing or separating a sample comprising:
    providing a phase-separated system comprising at least two phases, wherein
    a) the at least two phases each comprises a phase component selected from the group consisting of a polymer, a surfactant and combinations thereof, wherein at least one phase comprises a polymer;
        each said phase has an upper and a lower phase boundary; and
        each of the two or more phases has a different density and the phases, taken together, represent a density gradient; and
    b) introducing a sample comprising one or more analytes of interest to the phase-separated system without disrupting the phase boundaries of the phase-separated solution; and
    c) allowing each of the analytes to migrate to a location in the phase-separated system that is characteristic of its density, wherein during migration the sample contacts one or more of the two or more phases sequentially;
    wherein the phase-separated system is supported along a filament or on a sheet.

2. The method of claim 1, wherein greater than 80% of the analyte is located at one or more of the phase boundaries.

3. The method of claim 1, wherein greater than 90% of the analyte is located at one or more of the phase boundaries.

4. The method of claim 1, wherein the sample comprises a plurality of analytes and each analyte migrates to a different location in the phase-separated system.

5. The method of claim 1, wherein after migration, the analyte resides at a boundary location.

6. The method of claim 1, wherein the boundary location is at an interface between a phase with a density greater than the density of the analyte and a phase with a density that is less than the density of the analyte.

7. The method of claim 1, wherein after migration, the analyte resides within a phase of the phase-separated system whose density matches the density of the analyte.

8. The method of claim 1, wherein the phase-separated system is centrifuged to accelerate migration of the analyte.

9. The method of claim 1, wherein the analyte migrates under gravitational forces.

10. The method of claim 1, wherein the analyte migrates under buoyancy forces.

11. The method of claim 1, wherein the phase-separated system is provided as dispersion or emulsion in another carrier phase.

12. The method of claim 1, wherein the analyte of interest has a size of more than 200 nm.

13. The method of claim 1, wherein after analyte migration the phases and the analyte are in thermodynamic equilibrium.

14. The method of claim 1, wherein the phase separated system comprises three or more phases.

15. The method of claim 1, wherein the two or more phases comprise a common solvent which is an aqueous solvent.

16. The method of claim 1, wherein the two or more phases comprise a common solvent which is an organic solvent.

17. The method of claim 1, wherein the two or more phases comprise a common solvent which is a non-aqueous solvent selected from the groups consisting of liquid polymer, non-polar organic solvent, polar aprotic or protic solvent, supercritical fluid, fuel, oils, and fluorinated solvents, and combinations thereof.

18. The method of claim 17, wherein the common solvent comprises dichloromethane.

19. The method of claim 1, wherein the phase separated system comprises three or more phases including the two or more phases comprising a common solvent which is water and additional phase separated phases selected from the group consisting of organic solutions.

20. The method of claim 15, wherein the aqueous solvent is selected from the group consisting of water, sea water, isotopes of water, buffered water, irrigation water, mine effluent, colloidal solutions, emulsions, and a combination thereof.

21. The method of claim 1, wherein the analyte is selected from the group consisting of solid particles, an aggregate of particles, a liquid or gel immiscible in the solvent, a liquid crystal, and crystalline materials.

22. The method of claim 1, wherein the analyte is selected from the group consisting of gem, bead, metal, glass, rock, mineral, crystal, plastic, bone, rubber, paper, fabric, coal, polymer particles, and gases.

23. The method of claim 1, wherein the polymer is selected from the group consisting of homopolymers, random copolymers, block copolymers, graft copolymers, terpolymers, dendrimers, star polymers and combinations thereof.

24. The method of claim 23, wherein the polymer is linear, branched and/or cross-linked.

25. The method of claim 1, wherein the polymer is selected from the group consisting of dextran, dextran sulfate, chondroitin sulfate A, polysucrose, diethylaminoethyl-dextran, poly(2-vinylpyridine-N-oxide), polysucrose, poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propanesulfonic acid), poly(diallyldimethyl ammonium chloride), poly(styrene sulfonic acid), polyallylamine, alginic acid, poly(bisphenol A carbonate), polydimethylsiloxane, polystyrene, poly(4-vinylpyridine), polycaprolactone, polysulfone, poly(methyl methacrylate-co-methacrylic acid), poly(methyl methacrylate), poly(tetrahydrofuran), poly(propylene glycol), and poly(vinyl acetate) and copolymers or terpolymers thereof.

26. The method of claim 1, wherein the surfactant is selected from the group consisting of polysorbate, 3-[(3-cholamidopropyl)dimethylammonio]-1-propanesulfonate, polyoxyethylene-polyoxypropylene, 1-O-octyl-β-D-glucopyranoside, nonylphenol polyoxyethylene, 4-(1,1,3,3-Tetramethylbutyl)phenyl-polyethylene glycol, 2-(Perfluoroalkyl)ethyl methacrylate, N,N-dimethyldodecylamine N-oxide, polyethylene glycol dodecyl ether, sodium dodecyl sulfate, sodium cholate, benzylalkonium chloride and dodecyltrimethylammonium chloride.

27. The method of claim 1, wherein one or more phases further comprise an additive selected from the group consisting of a co-solvent, an acid, a base, a miscible polymer, vitamin, drug, antibiotic, small molecule, dye, and fluorophore.

28. The method of claim 1, wherein the sample is selected from the group consisting of a forensics study sample, a sample indicative of animal health, a sample indicative of human identity used for border control, homeland security, or intelligence, a sample from food processing, a sample indicative of product quality, a sample indicative of environmental safety, a sample containing different crystal polymorphs, and a combination thereof.

29. The method of claim 1, further comprising collecting the analyte from the boundary location.

* * * * *